(12) United States Patent
Frey et al.

(10) Patent No.: US 6,460,997 B1
(45) Date of Patent: Oct. 8, 2002

(54) APPARATUS AND METHOD FOR OBJECTIVE MEASUREMENTS OF OPTICAL SYSTEMS USING WAVEFRONT ANALYSIS

(75) Inventors: Rudolph W. Frey, Winter Park; James H. Burkhalter, Orlando; Neil Zepkin, Casselberry; Edward Poppeliers; John Alfred Campin, both of Orlando, all of FL (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/566,409

(22) Filed: May 8, 2000

(51) Int. Cl.[7] .................................................. A61B 3/10
(52) U.S. Cl. ......................................................... 351/211
(58) Field of Search ................................. 351/205, 206, 351/211, 212, 215, 219, 221, 246, 247; 356/124; 606/4, 5

(56) References Cited

U.S. PATENT DOCUMENTS

| | | | |
|---|---|---|---|
| 4,420,228 A | * 12/1983 | Humphery | ................... 351/212 |
| 5,825,476 A | 10/1998 | Abitol et al. | |
| 5,994,687 A | 11/1999 | Chanteloup et al. | |
| 6,043,885 A | 3/2000 | Mazuet et al. | |
| 6,050,687 A | 4/2000 | Bille et al. | |
| 6,057,913 A | 5/2000 | Brown et al. | |
| 6,086,204 A | 7/2000 | Magnante | |
| 6,155,684 A | 12/2000 | Bille et al. | |

OTHER PUBLICATIONS

Bille, et al., "Imaging of the Retina by Scanning Laser Tomography," *New Methods in Microscopy and Low Light Imaging*, vol. 1161, 1989, pp. 417–425.

Cubalchini, "Modal Wave–front Estimation from Phase Derivative Measurements," *J. Opt. Soc. Am.*, vol. 69, 1979, pp. 972–977.

(List continued on next page.)

Primary Examiner—George Manuel
(74) Attorney, Agent, or Firm—Jeffrey S. Schira

(57) ABSTRACT

An apparatus for determining aberrations of an eye includes a patient head rest allowing for positioning adjustment. The patient head rest is operable with an optical table having a base. The base includes a probe beam generating apparatus, probe beam directing optics which itself comprises a beam splitter; a mirror; and a lens. The probe beam directing optics is capable of directing a probe beam toward an eye of a patient positioned on the patient head rest. Video image components are provided and comprise a light source, a mirror; and a video camera. The video image components are capable of generating an image of an eye of a patient positioned on the patient head rest. Eye fixation components generate a target that the eye of a patient positioned on the patient head rest can view. The eye fixation components comprise a fixation target, a light source, a lens, and a mirror. Wavefront directing and analyzing components measure a wavefront emanating from the eye of a patient positioned on the patient head rest and determine aberrations of the eye that range from at least about + or − 1 diopters to at least about + or − 6 diopters. The wavefront directing and analyzing components include a lens; a mirror, a microlens array, a camera, and a data processor.

6 Claims, 28 Drawing Sheets

OTHER PUBLICATIONS

"Modal Wave–front Estimation from Phase Derivative Measurements," Referenced in Bille, U.S. Pat. No. 5,062,702 IDS, 1990.

Freischlad, et al., "Modal Estimation of a Wave Front from Difference Measurements Using the Discrete Fourier Transform," *J. Opt. Soc. Am.*, vol. 3, No. 11, Nov. 1986, pp. 1852–1861.

Klyce, et al., "Imaging, Reconstruction, and Display of Corneal Topography," *New Methods in Microscopy and Low Light Imaging*, vol. 1161, 1989, pp. 409–416.

Baker, "Optical Surface Testing of the Cornea," *New Methods in Microscopy and Low Light Imaging*, vol. 1161, 1989, pp. 427–437.

Southwell, "Wave–front Estimation from Wave–front Slope Measurements," *J. Opt. Soc. Am.*, vol. 70, No. 8, Aug. 1980, pp. 998–1005.

Liang, Junzhong, *A New Method to Precisely Measure the Wave Aberrations of the Human Eye with a Hartmann–Shack Wavefront Sensor*, Inaugural Dissertation, Dec. 1991, pp. 1–115, Heidelberg, Germany.

\* cited by examiner

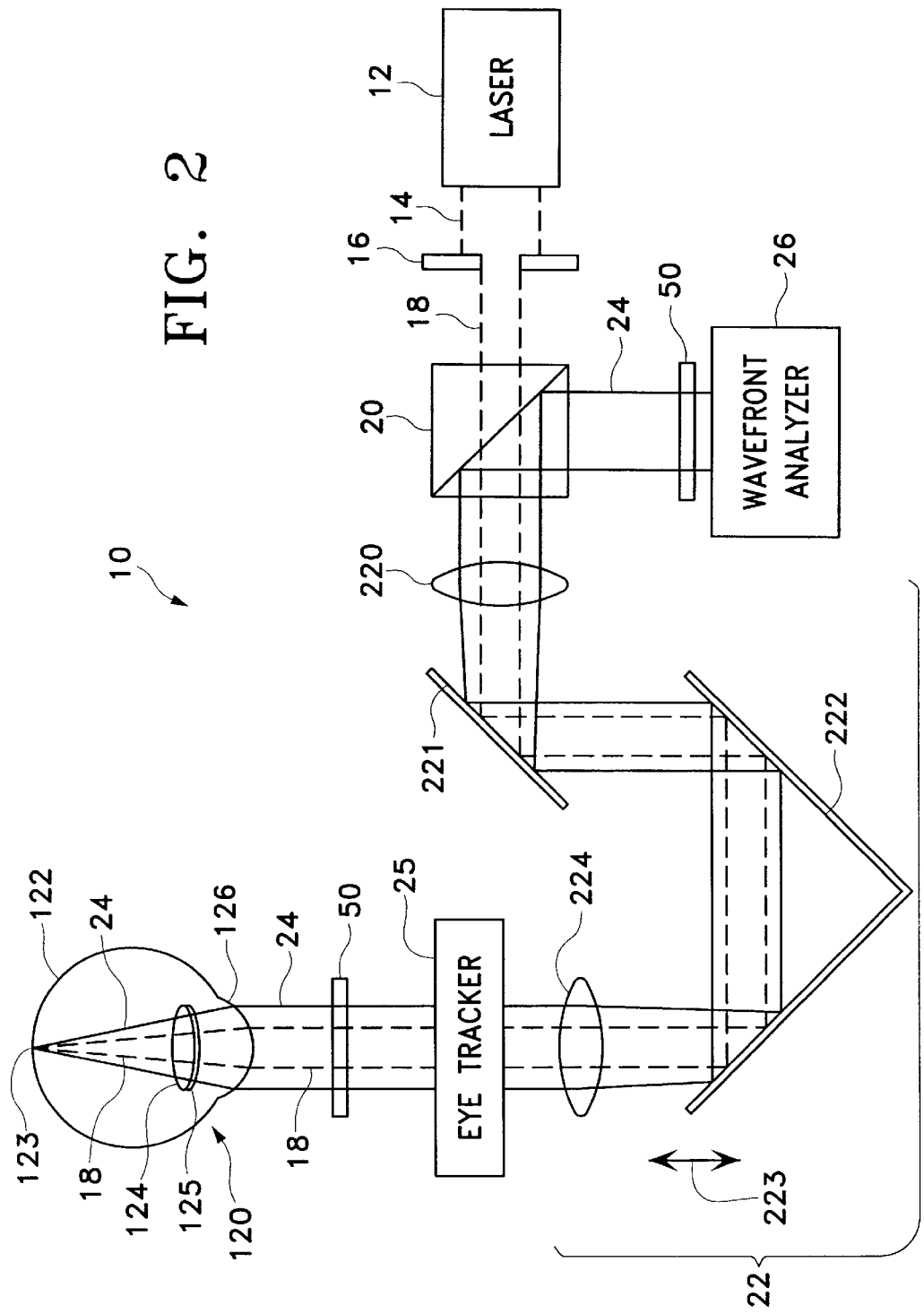

FIG. 25
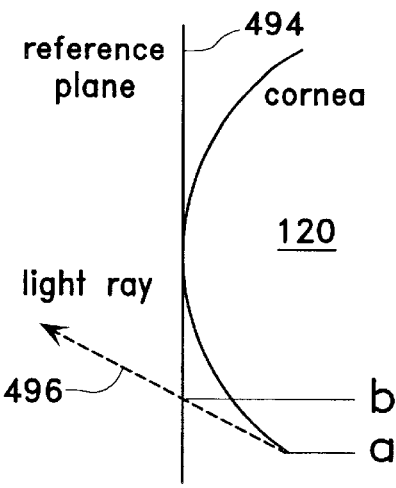
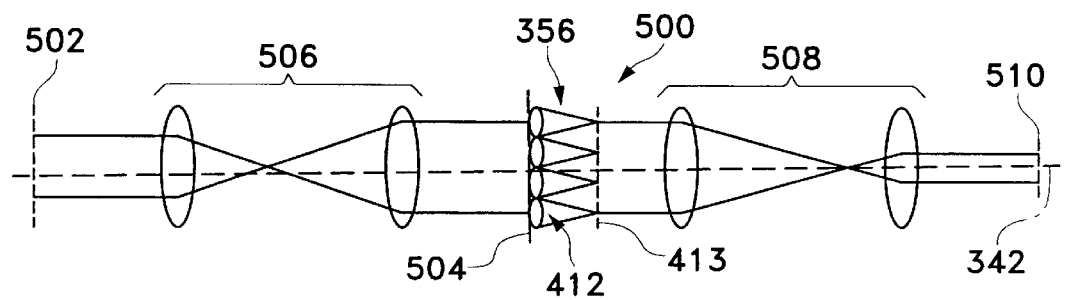
FIG. 26A
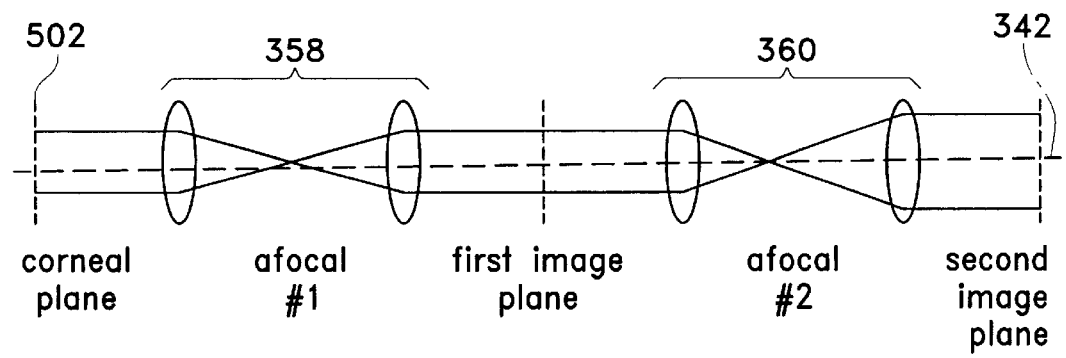
FIG. 26B

APPARATUS AND METHOD FOR OBJECTIVE MEASUREMENTS OF OPTICAL SYSTEMS USING WAVEFRONT ANALYSIS

FIELD OF THE INVENTION

The invention relates generally to optical aberration measurement and analysis, and more particularly to an objective measurement of optical systems, such as systems of a human eye.

BACKGROUND OF THE INVENTION

Optical systems having a real image focus can receive collimated light and focus it at a point. Such optical systems can be found in nature, e.g., human and animal eyes, or can be man-made, e.g., laboratory systems, guidance systems, and the like. In either case, aberrations in the optical system can affect the system's performance. By way of example, the human eye will be used to explain this problem.

A perfect or ideal eye diffusely reflects an impinging light beam from its retina through optics of the eye which includes a lens and a cornea. For such an ideal eye in a relaxed state, i.e., not accommodating to provide near-field focus, reflected light exits the eye as a sequence of plane waves. However, an eye typically has aberrations that cause deformation or distortion of reflected light waves exiting the eye. An aberrated eye diffusely reflects an impinging light beam from its retina through its lens and cornea as a sequence of distorted wavefronts.

There are a number of technologies that attempt to provide the patient with improved visual acuity. Typically, treatment is determined by placing spherical and/or cylindrical lenses of known refractive power at the spectacle plane (approximately 1.0–1.5 centimeters anterior to cornea) and literally asking the patient which lens or lens combination provides the clearest vision. This is an imprecise measurement of true distortions in the reflected wavefront because 1) a single spherocylindrical compensation is applied across the entire wavefront, 2) vision is tested at discrete intervals (i.e., diopter units) of refractive values, and 3) subjective determination by the patient is employed. Thus, conventional methodology for determining refractive errors in the eye is substantially less accurate than the techniques now available for measuring the ocular aberrations.

One method of measuring ocular refractive errors is disclosed in U.S. Pat. No. 5,258,791 to Penney et al. for "Spatially Resolved Objective Autorefractometer," which teaches the use of an autorefractometer to measure the refraction of the eye at numerous discrete locations across the corneal surface. The autorefractometer is designed to deliver a narrow beam of optical radiation to the surface of the eye, and to determine where that beam strikes the retina using a retinal imaging system. Both the angle of the beam's propagation direction with respect to the optical axis of the system and the approximate location at which the beam strikes the corneal surface of the eye are independently adjustable. However, a small uncertainty or error in the location of the beam's point of incidence on the cornea exists due to the curved corneal surface. For each point of incidence across the corneal surface, the refraction of the eye corresponding to that surface point can be determined by adjusting the angle at which the beam strikes the cornea until the beam refracted on to the iris strikes the fovea centralis. Adjustment of the beam angle of propagation can be accomplished either manually by the patient or automatically by the autorefractometer, if a feedback loop involving a retinal imaging component is incorporated.

Penney '791 further teaches the use of the autorefractometer measurements in determining the appropriate corneal surface reshaping to provide emmetropia, a condition of a normal eye when parallel beams or rays of light are focused exactly on the retina and vision is perfect. This is accomplished by first obtaining an accurate measurement of corneal surface topography using a separate commercially available device. A mathematical analysis is then performed using an initial corneal topography at each surface reference point, the measured refraction at each surface point, and Snell's law of refraction, to determine a desired change in surface contour at each reference point.

A major limitation to the approach described by Penney '791 is that a separate measurement of corneal topography is desired to perform the Snell's Law analysis of needed refraction change. This adds significantly to the time and cost of a complete and desirable diagnostic evaluation. Further, the accuracy of the refraction change analysis will be dependent upon the accuracy of the topographic measurement and the accuracy of the autorefractometer measurement. In addition, any error in the spatial orientation of a topography map with respect to a refraction map will degrade the accuracy of the measured profile. Yet another limitation to known approaches such as described in Penney '791, by way of example, is that test points on the corneal surface are examined sequentially. Eye motion during the examination, either voluntary or involuntary, could introduce substantial errors in the refraction measurement. Penney '791 teaches detection of such eye movement by deliberately including measurement points outside the pupil, i.e., in the corneal region overlying the iris, where the return from the retina will obviously be zero at specific intervals in the examination sequence. However, this approach may still allow substantial undetected eye movement error between such iris reference points.

By way of example, one method and system known in the art, are disclosed by Junzhong Liang et al. in "Objective Measurement Of Wave Aberrations Of The Human Eye With The Use Of A Hartmann-Shack Wave-Front Sensor," published in the Journal of the Optical Society of America, Volume 11, No. 7, July 1994, pages 1949–1957. Liang et al. teach the use of a Hartmann-Shack wavefront sensor to measure ocular aberrations by measuring the wavefront emerging from the eye by the retinal reflection of a focused laser light spot on the retina's fovea. The actual wavefront is reconstructed using wavefront-estimation with Zernike polynomials.

The imprecise measurement technique of placing lenses of known refractive power anterior to the cornea and asking a patient which lens or lens combination provides the clearest vision has been improved with the use of autorefractometers, as described in Penny '79, or with the use of wavefront sensors as described by Liang et al. Spatially resolved refraction data, in combination with measured existing surface contour of the anterior surface of the eye, enable a calculation of a detailed spatially resolved new contour. However, it would be an improvement in this art if such vision measurements could be made without the need for this contour data, and further without the need for feedback from the patient regarding an appropriate lens. Liang et al. discloses the use of a Hartmann-Shack wavefront sensor to measure ocular aberrations by measuring the wavefront emerging from the eye by retinal reflection of a focused laser light spot on the retina's fovea. A parallel beam of laser light passes through beam splitters and a lens pair which brings the beam to a focus point on the retina by the optics of the eye. Possible myopia or hyperopia of the tested eye is determined by movement of a lens within the lens pair. The focused light on the fovea is then assumed to be diffusely reflected and acts as a point source located on the retina. The reflected light passes through the eye and forms a distorted wavefront in front of the eye that results from the ocular aberrations. The aberrated wavefront is then directed to the wavefront sensor.

A point source of radiation on the retina would be ideal for such measurements. However, when the perfect eye receives a collimated beam of light, the best possible image on the retina is a diffraction limited spot. As illustrated by way of example, with Penny et al. and Liang et al., discussed above, and typical for those of skill in the art, parallel or collimated beams are used with the optics of the eye being measured to achieve this diffraction limited spot for such objective measurements. To do so, a setup for each patient includes a lens or lens combination and adjustments thereto for accommodating that patient's specific visual acuity. Providing a lens combination, as well as setting up for their use becomes cumbersome, time consuming, and at an additional expense. Eliminating the need for such optics is desirable and eliminates a variable within optical measurement systems that typically include many variables. Further, there is a need for providing optical characteristics of an eye without requiring feedback from the patient. By way of example, the patient may be a wild or domestic animal, living or dead.

The Hartmann-Shack wavefront sensor disclosed by Liang et al. includes two identical layers of cylindrical lenses with the layers arranged so that lenses in each layer are perpendicular to one another, as further disclosed in U.S. Pat. No. 5,062,702 to Bille. In this way, the two layers operate as a two-dimensional array of spherical lenslets that divide the incoming light wave into sub-apertures. The light through each sub-aperture is brought to focus in the focal plane of the lens array where a charge coupled device (CCD) image module resides.

The system of Liang et al. is calibrated by impinging an ideal plane wave of light on the lenslet array so that a reference or calibrating pattern of focus spots is imaged on the CCD. Since the ideal wavefront is planar, each spot related to the ideal wavefront is located on the optical axis of the corresponding lenslet. When a distorted wavefront passes through the lenslet array, the image spots on the CCD are shifted with respect to a reference pattern generated by the ideal wavefront. Each shift is proportional a local slope, i.e., partial derivatives of the distorted wavefront, which partial derivatives are used to reconstruct the distorted wavefront, by means of modal wavefront estimation using Zernike polynomials.

However, the system disclosed by Liang et al. is effective only for eyes having fairly good vision. Eyes that exhibit considerable myopia (nearsightedness) would cause the focus spots to overlap on the CCD, thereby making local slope determination practically impossible for eyes having this condition. Similarly, eyes that exhibit considerable hyperopia (farsightedness) deflect the focus spots such that they do not impinge on the CCD thereby again making local slope determination practically impossible for eyes having this condition.

SUMMARY OF THE INVENTION

In general, an embodiment of the present invention provides a method and system for objectively measuring aberrations of optical systems by wavefront analysis. Another embodiment further provides for the objective measurement of ocular aberrations having a dynamic range that can cope with large amounts of such aberrations so as to be useful in practical applications. Still another embodiment of the present invention provides a method and system for objectively measuring ocular aberrations using a wavefront analyzer of simple and inexpensive design.

One embodiment of the present invention provides an apparatus and method for making objective and detailed measurements of aberrations present in human eyes.

Aberrations measured by the apparatus include "higher order" phenomena, such as spherical aberration and coma, in addition to the traditional myopia/hyperopia and astigmatism.

In accordance with an embodiment of the present invention, an energy source generates a beam of radiation. Optics, disposed in the path of the beam, direct the beam through a focusing optical system that has a rear portion which provides a diffuse reflector. The beam is diffusely reflected back from the rear portion as a wavefront of radiation that passes through the focusing optical system to impinge on the optics. The optics project the wavefront to a wavefront analyzer in direct correspondence with the wavefront as it emerges from the focusing optical system. A wavefront analyzer is disposed in the path of the wavefront projected from the optics and calculates distortions of the wavefront as an estimate of ocular aberrations of the focusing optical system. The wavefront analyzer includes a wavefront sensor coupled to a processor that analyzes the sensor data to reconstruct the wavefront to include the distortions thereof.

One embodiment of the present invention, herein described by way of example, utilizes wavefront sensing to measure the aberrations of the eye. When one considers the perfect or ideal eye as earlier described, a perfectly collimated light beam (i.e., a bundle of parallel light rays) incident on the perfect, ideal emmetropic eye, focuses to a diffraction-limited small spot on the retina. This perfect focusing is true for all light rays passing through the entrance pupil, regardless of position. From the wavefront perspective, the collimated light represents a series of perfect plane waves striking the eye. Due to the reversible nature of light ray propagation, the light emanates from an illuminated spot created on the retina as wavefronts exiting the ideal eye as a series of perfect plane waves. The apparatus of the present invention achieves this ray reversal effect using a probe beam optical path for projecting a small diameter, eye-safe laser beam into the eye and onto the fovea. The light scattered from the irradiated retina serves as a secondary source for a re-emitted wavefront. The probe laser beam strikes the retina at an appropriate foveal location to illuminate a sufficiently small spot. A fixation optical path is provided which includes a reference target aligned to an optical axis. This allows a patient to fixate on a target. A video path provides a video image of the eye plane, centered on the optical axis. A video image of the eye allows a clinical operator to assist in orienting the eye for the wavefront measurement.

Embodiments of the present invention, herein described, provide a refraction measurement system that easily accommodates the measurement of vision characteristics of the eye, even in the presence of finite refractive errors. The time for a patient to be in a fixed position during examination is reduced, while at the same time providing a useful source of light on the retina of the eye to be measured regardless of the characteristics of the eye of that patient or other patients to be examined. Desirably, measurements are made without requiring patient or operator feedback. One method aspect of the invention for measuring optical characteristics of an optical system, such as the eye, includes focusing an optical beam onto an anterior surface of the eye for providing a finite source of secondary radiation on the retina of the eye, which secondary radiation is emitted from the retina as a reflected wavefront of radiation that passes through the eye. The reflected wavefront is directed onto a wavefront analyzer for measuring distortions associated with the reflected wavefront.

In one embodiment, the radiation is optical radiation and the wavefront sensor is implemented using a plate and a planar array of light-sensitive cells. The plate is generally opaque but that has an array of light transmissive apertures that selectively let impinging light therethrough. The plate is disposed in the path of the wavefront so that portions of the wavefront pass through the light transmissive apertures. The planar array of cells is arranged parallel to and spaced apart from the plate by a selected distance. Each portion of the wavefront passing through one of the light transmissive apertures illuminates a geometric shape covering a unique plurality of cells.

As herein described, by way of example, the wavefront optical path of the present invention relays the re-emitted wavefront from the corneal plane to an entrance face of a Hartman-Shack wavefront sensor. The wavefront incident on the sensor is received by a sensitive charged-coupled device (CCD) camera and an optical plate containing an array of lenslets. The lenslet array is parallel to the CCD detector face with a distance therebetween approximately equal to the focal length of each lens in the lenslet array. The lenslet array divides the incoming wavefront into a matching array of "wavelets," each of which focuses to a small spot on the CCD detector plane. The constellation of wavelet spots in the CCD is used to reconstruct the shape of the incident wavefront. Collimated light striking the lenslet at normal (perpendicular) incidence would focus to the spot on the CCD face where this optical axis intersects. The optics of the apparatus provides such collimated light to the wavefront sensor using a calibration optical path. Collimated light CCD images are routinely obtained as part of a daily calibration process and used for reference in analyzing experimental data.

However, in the case of a reflected aberrated wave front, light focuses to a spot displaced from the collimated reference point by a distance Dx. The distance from the lenslet face to the CCD surface, Dz, is precisely known. Therefore, dividing the measured displacement, Dx, by the known propagation distance, Dz, the slope of the wavefront at the location of this lens element is determined. The same calculation is applied in the y direction within the plane, and the entire process applied to every lenslet element irradiated by the wavefront. A mathematical algorithm is then applied to reconstruct the wavefront shape consistent with the calculated Dx/Dz and Dy/Dz slope data. Regardless of which wavefront sensor is used, the distance between the planar array of cells and the opaque plate, or the array of lenslets, can be varied to adjust the slope measurement gain of the wavefront sensor and thereby improve the dynamic range of the system.

Another measure of dynamic range enhancement is provided by the focusing optics. The focusing optics includes first and second lenses maintained in fixed positions in the path of the beam and wavefront. An arrangement of optical elements is disposed between the lenses in the path of the beam and the wavefront. The optical elements are adjustable to change the optical path length between the lenses.

A method aspect of the present invention, as herein described, determines aberrations of an eye requiring greater than a + or −3 diopter change, and includes directing an optical beam onto a retina of an eye, reflecting the optical beam from the retina of the eye, determining characteristics of a wavefront in a reflected optical beam, and generating data based on the characteristics of the wavefront, which data quantifies the aberrations of the eye. The data may further be generated based on refractive indices of media through which the optical beam passes. Yet further, data based on the characteristics of the wavefront, which data quantifies the aberrations of the eye for a discrete section of the eye may also be generated.

One method for determining aberrations of an eye, herein described by way of example, includes directing a probe beam along a probe beam path toward an eye, directing a fixation image along a fixation image path toward the eye, directing a light source along a video image path toward the eye, generating a video image of the eye, directing a wavefront originating from the eye along a wavefront path, wherein the probe beam path, the fixation image path, the video image path, and the wavefront path are coincident at least along a portion of their respective paths, the probe beam path terminating at the retina of the eye and the probe beam reflecting from the retina of the eye as a wavefront, aligning the eye with the probe beam path based at least in part on the video image of the eye generated by the light source directed along the video image path, measuring the wavefront, and generating data representative of the aberrations of the eye based on the measurement of the wavefront. Further, the aligning of the eye with the probe beam path based at least in part on the video image of the eye generated by the light source directed along the video image path, may have the wavefront pass through a single microlens array.

One apparatus for determining the aberrations of an eye comprises a patient head rest comprising vertical adjustment, the patient head rest associated with an optical table having a base. The base carries a probe beam generating apparatus, probe beam directing optics, the probe beam directing optics comprising a beam splitter; a mirror; and a lens, the probe beam directing optics being capable of directing a probe beam toward an eye of a patient positioned on the patient head rest, video image components, the video image components comprising a light source, a mirror, and a video camera, the video image components being capable of generating an image of an eye of a patient positioned on the patient head rest, eye fixation components, the eye fixation component comprising a fixation target; a light source; a lens; and a mirror, the fixation components being capable of generating a target that the eye of a patient positioned on the patient head rest can view, and wavefront directing and analyzing components, the wavefront directing and analyzing components comprising a lens, a mirror, a microlens array, a camera, and a data processor. The wavefront directing and analyzing components are capable of measuring the wavefront emanating from the eye of a patient positioned on the patient head rest and determining aberrations of said eye that range from at least about + or −1 diopters to at least about + or −6 diopters.

BRIEF DESCRIPTION OF THE DRAWINGS

Embodiments of the invention are described by way of example with reference to the accompanying drawings in which:

FIG. 2 is a simplified schematic of the system for determining ocular aberrations in accordance with the essential features of the present invention;

FIG. 25 illustrates a geometric effect of a curved corneal surface on a wavefront measurement;

FIG. 26A is a pictorial line drawing illustrating magnification modification to the embodiment of FIG. 12; and FIG. 26B is a pictorial line drawing illustrating optical elements of the present invention.

DETAILED DESCRIPTION OF THE INVENTION

The present invention will now be described more fully hereinafter with reference to the accompanying drawings, in which embodiments of the present invention are shown by way of illustration and example. This invention may, however, be embodied in many forms and should not be construed as limited to the embodiments set forth herein. Rather, these embodiments are provided so that this disclosure will be thorough and complete, and will fully convey the scope of the invention to those skilled in the art. Like numbers refer to like elements throughout.

By way of illustrative example, the present invention will be described with respect to diagnosing a human eye. However, it is to be understood that the teachings of the present invention are applicable to any optical system having a real image focus that can be, or can be adapted to diffusely reflect a focused spot of radiation from a rear portion of the optical system back through the optical system as a wavefront of radiation. Thus, the present invention can be used with human or animal eyes of patients that may be alive or dead, or any man-made optical system.

Figure 1A:
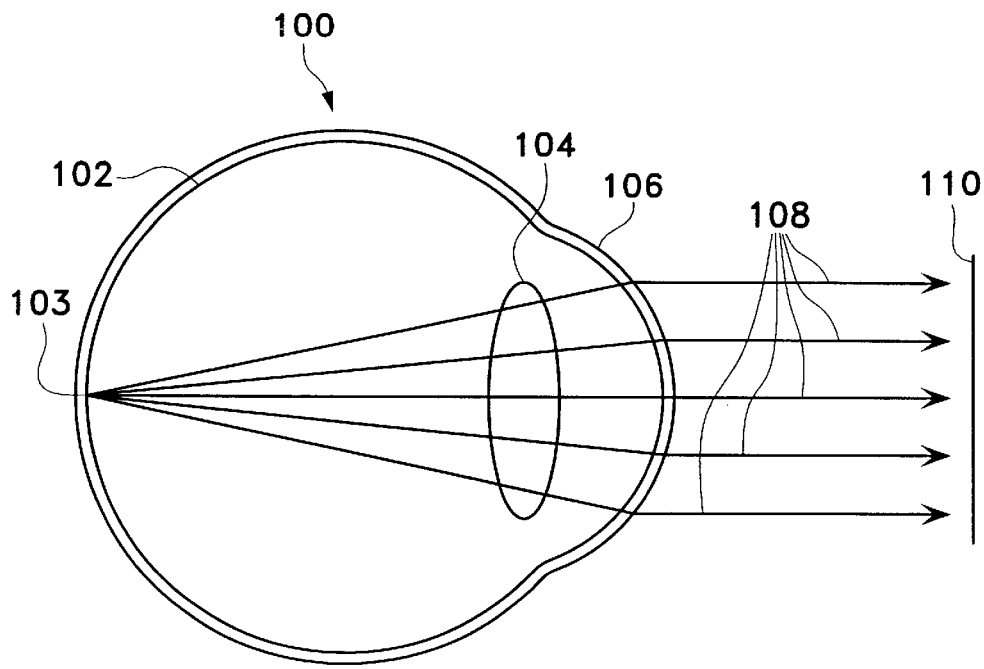
FIG. 1A is a schematic view of the ideal eye reflecting light from its retina as a planar wavefront.
Figure 1B:
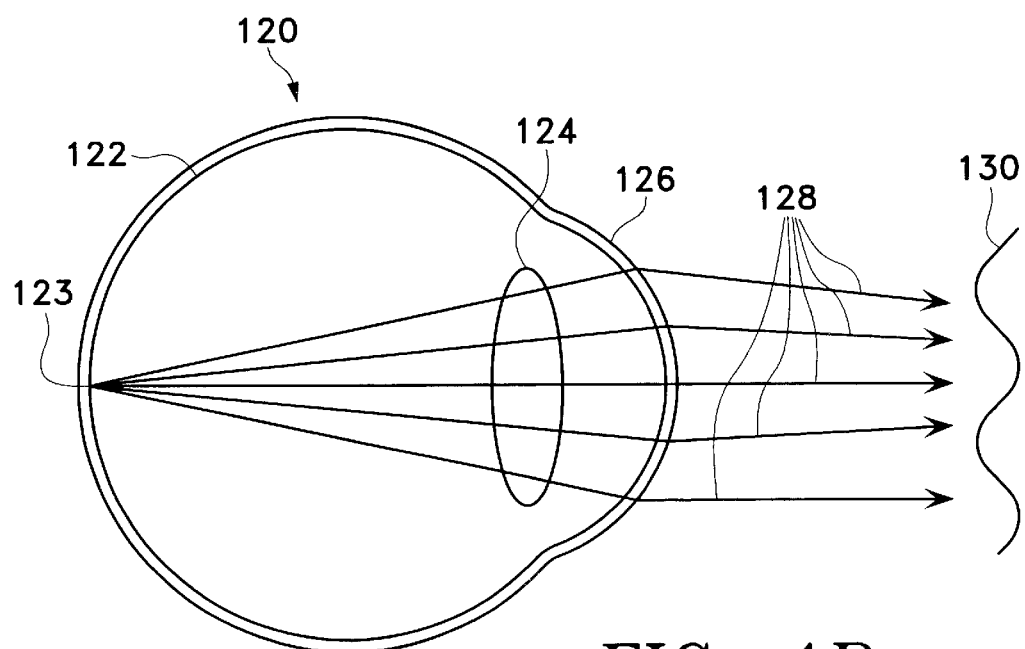
FIG. 1B is a schematic view of an aberrated eye reflecting light from its retina as a deformed wavefront.
Figure 1C:
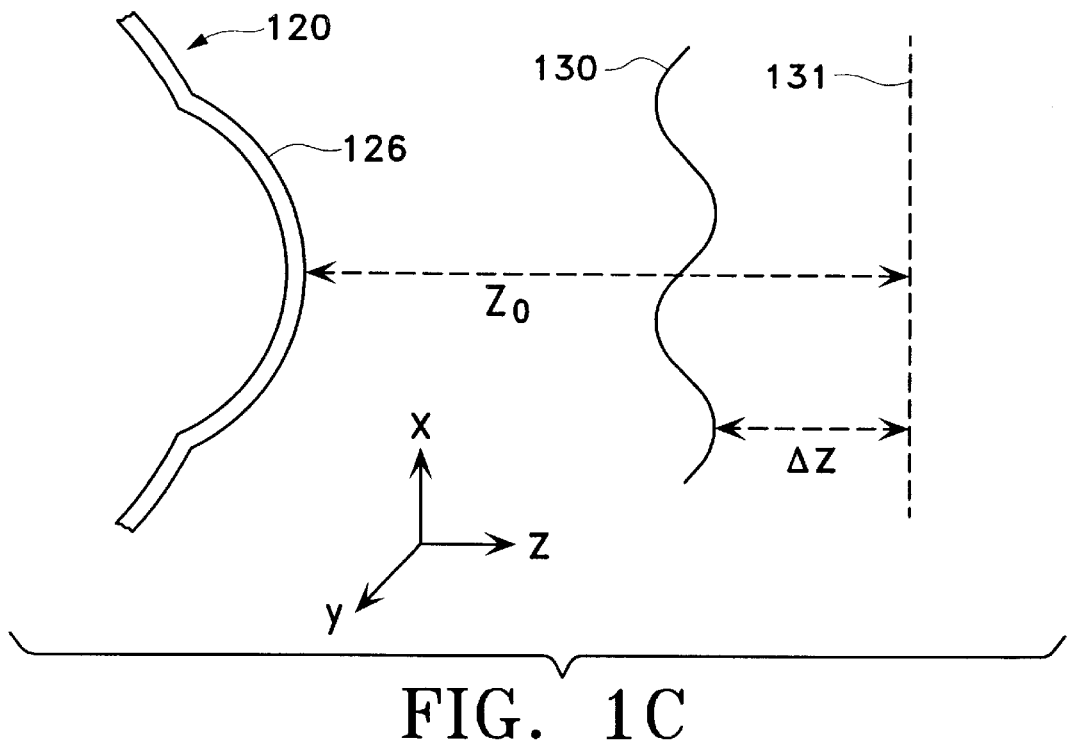
FIG. 1C is a schematic view of the distorted wavefront relative to a reference plane to show the wavefront error or optical path difference as a function of transverse distance in the propagation direction.

The method of using wavefront analysis will be introduced with reference to the eye example and the aid of the schematic drawings of FIGS. 1A, 1B, and 1C. As earlier described with reference to an ideal eye, and with reference now to FIG. 1A, the ideal emmetropic or perfect eye 100 diffusely reflects an impinging light beam (not shown for sake of clarity) from the back of its retina 102 (i.e., the fovea centralis 103) through the eye's optics which includes lens 104 and cornea 106. For such an ideal eye 100 in a relaxed state, i.e., not accommodating to provide near-field focus, the reflected light (represented by arrows 108) exits the eye 100 as a sequence of plane waves, one of which is represented by straight line 110. However, as illustrated with reference to FIG. 1B, a typical eye 120 normally has aberrations that cause deformation or distortion of a reflected wave exiting the eye, where the aberrated eye 120 diffusely reflects an impinging light beam (again not shown for sake of clarity) from the back of its retina 122 of the fovea centralis 123 through lens 124 and cornea 126. For the aberrated eye 120, the reflected light 128 exits the eye 120 as a sequence of distorted wavefronts, one of which is represented by wavy line 130.

With reference now to FIG. 1C, a coordinate system is defined for convenience, where positive x is upward in the plane of the figure, positive y is outward from the plane of the figure, and positive z is to the right along a propagation direction. The distorted wavefront 130 is herein described mathematically as W(x,y). One method of measuring distortions in the wavefront 130 is by determining a spatial separation Δz between a reference plane 131 (by way of example, a plane analogous to the ideal wavefront 110) at a known distance $z_0$ from the eye 120 at each (x,y) point of the distorted wavefront 130 as the leading edge of the wavefront 130 traverses the distance $z_0$. This is described mathematically as:

$$\Delta z(x,y) = z_0 - W(x,y) \quad (1)$$

These Δz measurements define optical path differences due to aberrations in the eye 120 being tested, by way of example.

Depending on the desired therapy (for example, synthetic lens addition), the material thickness at each (x,y) coordinate can be calculated directly if the refractive index of the material in question is known. For many procedures, such as intra-ocular lens implantation, a wavefront analysis may be performed repetitively during a procedure to provide feedback information as to the appropriate endpoint of the procedure.

Figure 1D:
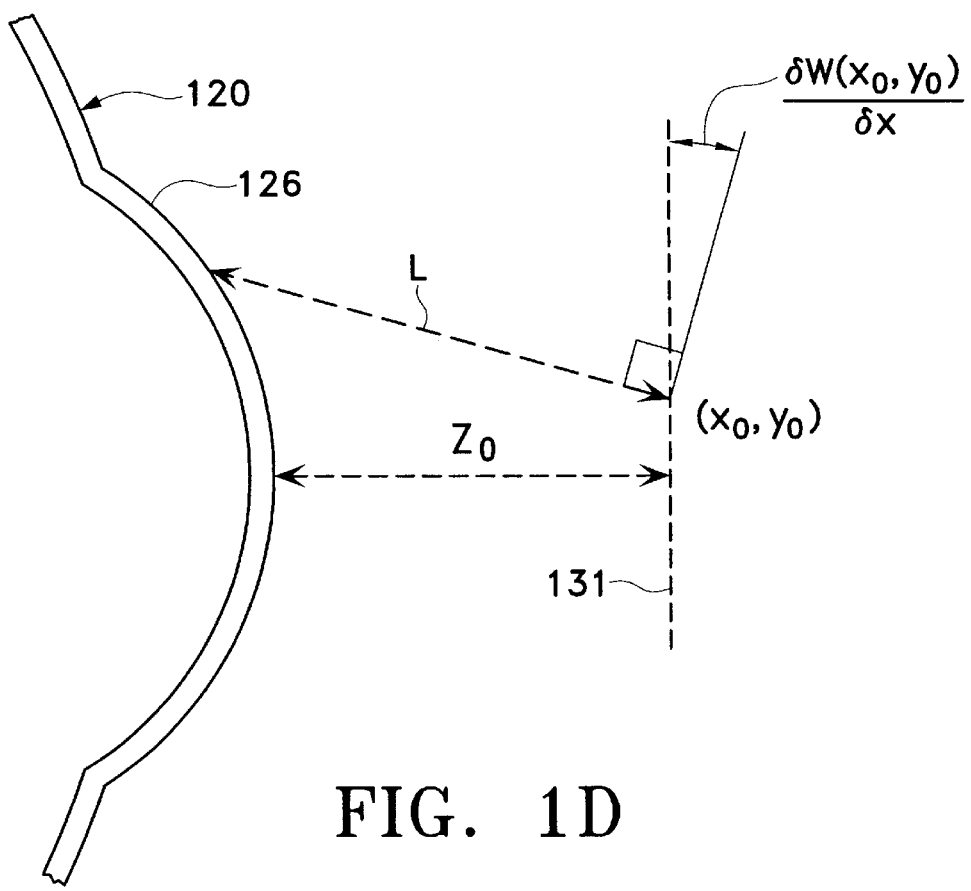
FIG. 1D is a schematic view illustrating use of a reference plane.

In terms of the illustrative example, the differences Δz(x, y) between the distorted wavefront 130 and the ideal wavefront 110 are the consequence of the aberrations in the eye. Measuring these aberrations consists of introducing an optical path difference at the reference plane 131 of negative Δz(x,y). If the treatment approach, by way of example, consists of adding material to the cornea 126, then one choice for the location of reference plane 131 is tangential to the surface of cornea 126 (i.e. at z=O). This is illustrated schematically with reference to FIG. 1D, where the curvature of the cornea 126 is greatly exaggerated for clarity of illustration.

The appropriate corneal addition at any (x,y) transverse coordinate is, to within a small error, given by:

$$\Delta z(x,y)/(n_c - 1) \quad (2)$$

where $n_c$ is the refractive index of corneal tissue or 1.3775. The method described in detail below calculates Δz(x,y) by first measuring the local slopes in wavefront 130, i.e. ∂W(x, y)/∂x and ∂W(x,y)/∂y, at a number of points in the transverse x and y directions in reference plane 131 and then generating a mathematical description of W(x,y) having slopes in best possible agreement with the experimentally determined values. One such slope ∂W(x,y)/∂x is illustrated with reference again to FIG. 1D. In doing this, a small error is introduced due to the fact that distorted wavefront 130 is measured at the reference plane 131 while wavefront 130 emerged from a curved corneal surface just posterior to reference plane 131. By way of example, an error $E_x(x,y)$ is the lateral displacement in the x-direction at each (x,y) location at the measurement plane (i.e., reference plane 131) to the curved corneal surface. A similar error will be manifest for any measurements involving curved optical surfaces. The error will generally increase with both (x,y) displacement from the point of tangency and local wavefront error.

The magnitude of error $E_x(x,y)$ can be found for each measurement location (x,y) measured at an arbitrary coordinate, e.g., $(x_0,y_0)$ by projecting that location back to the point of origin on the cornea 126. This is explained mathematically with reference again to FIG. 1D, where by way of example, it is assumed that the error is in the plane of the figure, i.e., the plane defined by $y=y_0$, although it is quite straightforward mathematically to extend the analysis to include errors in the y-dimension. The quantification of a line L tracing the propagation of the wavefront 131 measured at $(x_0,y_0)$ in the $z_0$ reference plane from the corneal surface to the reference plane is:

$$L(x) = z_0 - \frac{(x - x_0)}{\partial W(x_0, y_0)/\partial x} \quad (3)$$

If the corneal surface in the plane of the figure is described by the expression $S(x_0,y_0)$, then the point of origin for the wavefront 131 in question can be found by finding the point of intersection between L(x) and S $(x,y_0)$. Mathematically, one finds the value $x^1$, that satisfies $L(x^1) = S(x_0,y_0)$. The error $E_x(x_0,y_0)$ is then given as $Ex(x_0,y_0) = x^1 - x_0$. Extending the analysis to consider errors in the y-direction would yield a similar expression for $E_y$ where $E_y(x_0, y_0) = y^1 - y_0$. If significant, these transverse errors can be compensated for by laterally displacing the aberration calculated at each (x,y) coordinate by the amounts $E_x(x,y)$ and $E_y(x,y)$.

In the case of human corneas, the transverse error under most circumstances will be negligible. The error will be zero at the origin where the corneal tissue and reference plane 131 are tangent. For human corneas, the tissue is approximately spherical with a radius of curvature of approximately 7.5–8.0 mm. The treatment radius is typically no more than 3 mm, and local wavefront radius of curvature will almost never exceed 50 mm (a 20 diopter refractive error). The transverse error E at a 3 mm treatment radius for a local wavefront radius of curvature of 50 mm is less than 40 μm.

For certain ophthalmic procedures, wavefront analysis can also be used repetitively during the procedure to provide useful feedback information. One example of such use would be following placement of an intra-ocular lens implant (IOL). The analysis helps to identify whether the appropriate refractive power IOL has been inserted, or whether a different refractive power IOL should be used.

In order to perform wavefront analysis in a manner compatible with procedures such as those described above, the amount of spatial separation of component portions of wavefront 130 relative to the corresponding component portions of the planar or ideal wavefront 110 is measured. It is the system and method of the present invention that allows such separation to be objectively and accurately measured for even substantially aberrated eyes 120 including those exhibiting severe defects such as severe myopia or hyperopia.

For the evaluation or measurement portion of the present invention, the patient's pupil should ideally be dilated to approximately 6 mm or more, i.e., the typical size of a human pupil in low light. Smaller amounts of dilation or no dilation at all may also evaluated or measured. In this way, the eye is evaluated while it is using the greatest area of the cornea so that any measurement takes into account the largest usable corneal area of the patient's eye. A lesser amount of the cornea is used in daylight where the pupil is considerable smaller, e.g., on the order of 3 millimeters. Dilation can be brought about naturally by implementing the measurement portion of the present invention in a low light environment such as a dimly lit room. Dilation can also be induced through the use of pharmacologic agents.

Referring now to FIG. 2, a simplified schematic of one exemplary embodiment of the apparatus 10 of the present invention is illustrated. The apparatus 10 includes a laser 12 for generating optical radiation used to produce a small-diameter laser beam 14. The laser 12 generates a collimated laser light beam (represented by dashed lines for the beam 14) of a wavelength and power that is eye-safe. For ophthalmic applications, appropriate wavelengths would include the entire visible spectrum and the near infrared spectrum. By way of example, appropriate wavelengths may be in a range of from approximately 400 to 1000 nanometers, including 550, 650, 850 useful wavelengths. While operation in the visible spectrum is generally desired, since these are the conditions in which the eye operates, the near infrared spectrum may offer advantages in certain applications. For example, the patient's eye may be more relaxed if the patient does not know measurement is taking place. Regardless of the wavelength of the optical radiation, power should be restricted in ophthalmic applications to eye safe levels. For laser radiation, appropriate eye-safe exposure levels can be found in the U.S. Federal Performance Standard for Laser Products. If the analysis is to be performed on an optical system other than the eye, the examination wavelength range logically should incorporate the intended performance range of the system.

To select a small-diameter collimated core of laser light beam 14, an iris diaphragm 16 is used to block all of laser light beam 14 except for the part of a size desired for use. In terms of the present invention, the laser beam 18 will have a diameter in the range of approximately 0.5–4.5 millimeters with 1–3 millimeters being typical, by way of example. A badly aberrated eye uses a smaller diameter beam while an eye with only slight aberrations can be evaluated with a larger diameter beam. Depending on the output divergence of the laser 12, a lens, as will be later described, can be positioned in the beam path to optimize collimating of the beam.

Laser beam 18, as herein described by way of example, is a polarized beam that is passed through a polarization sensitive beam splitter 20 for routing to a focusing optical train 22 which optical train operates to focus the laser beam 18 through the optics of the eye 120 (e.g., the cornea 126, pupil 125 and the lens 124) to the retina 122. It is to be understood that the lens 124 may not be present for a patient that has undergone a cataract procedure. However, this does not affect the present invention.

In the illustrated example of FIG. 2, the optical train 22 images the laser beam 18 as a small spot of light at or near the eye's fovea centralis 123 where the eye's vision is most acute. Note that the small spot of light could be reflected off another portion of retina 122 in order to determine aberrations related to another aspect of one's vision. For example, if the spot of light were reflected off the area of the retina 122 surrounding the fovea centralis 123, aberrations specifically related to one's peripheral vision could then be evaluated. In all cases, the spot of light may be sized to form a near-diffraction limited image on the retina 122. Thus, the spot of light produced by laser beam 18 at fovea centralis 123 does not exceed approximately 100 micrometers in diameter and, typically, is on the order of 10 micrometers.

The diffuse reflection of the laser beam 18 back from the retina 122 is represented in FIG. 2 by solid lines 24 indicative of radiation that passes back through the eye 120. The wavefront 24, earlier described with reference to FIG. 1B as distorted wavefront 130 impinges on and is passed through the optical train 22 and on to the polarization sensitive beam splitter 20. The wavefront 24 is depolarized relative to the laser beam 18 due to reflection and refraction as the wavefront 24 emanates from the retina 122. Accordingly, the wavefront 24 is turned at the polarization sensitive beam splitter 20 and directed to a wavefront analyzer 26 such as a Hartmann-Shack (H-S) wavefront analyzer. In general, the wavefront analyzer 26 measures the slopes of wavefront 24, i.e., the partial derivatives with respect to x and y, at a number of (x,y) transverse coordinates, as earlier described with reference to FIGS. 1C and 1D. This partial derivative information is then used to reconstruct or approximate the original wavefront with a mathematical expression such as a weighted series of Zernike polynomials.

The polarization states for the incident laser beam 18 and the beam splitter 20 minimizes the amount of stray laser radiation reaching the sensor portion of the wavefront analyzer 26. In some situations, stray radiation may be sufficiently small when compared to the radiation returning from the desired target (e.g., the retina 122) so that the polarization specifications are unnecessary.

The present invention is able to adapt to a wide range of vision defects and as such achieves a new level of dynamic range in terms of measuring ocular aberrations. Dynamic range enhancement is accomplished with the optical train 22 and/or a wavefront sensor portion of the wavefront analyzer 26. With continued reference to FIG. 2, the optical train 22 includes a first lens 220, a flat mirror 221, a Porro mirror 222 and a second lens 224 all of which lie along the path of laser beam 18 and the wavefront 24. The first lens 220 and the second lens 224 are identical lenses maintained in fixed positions. The Porro mirror 222 is capable of linear movement as indicated by arrow 223 to change the optical path length between the lenses 220 and 224. However, it is to be understood that the present invention is not limited to the particular arrangement of the flat mirror 221 and the Porro mirror 222 and that other optical arrangements, as will herein be described by way of example, will be used without departing from the teachings and benefits of the present invention.

A "zero position" of the Porro mirror 222 is identified by replacing the eye 120 illustrated with reference again to FIG. 2, by a calibration source, as will be described later by way of further example, of collimated light to provide a reference wavefront such as the perfect plane wave 110, earlier described with reference to FIG. 1A. Such a source could be realized by a laser beam expanded by a beam telescope to the diameter that will cover the imaging plane of wavefront analyzer 26 and adjustment of the Porro mirror 222 until the wavefront analyzer 26 detects the light as being collimated. Note that the changes in optical path length brought about by the Porro mirror 222 can be calibrated in diopters to provide an approximate spherical dioptric measurement, as will be explained further below.

Figure 3:
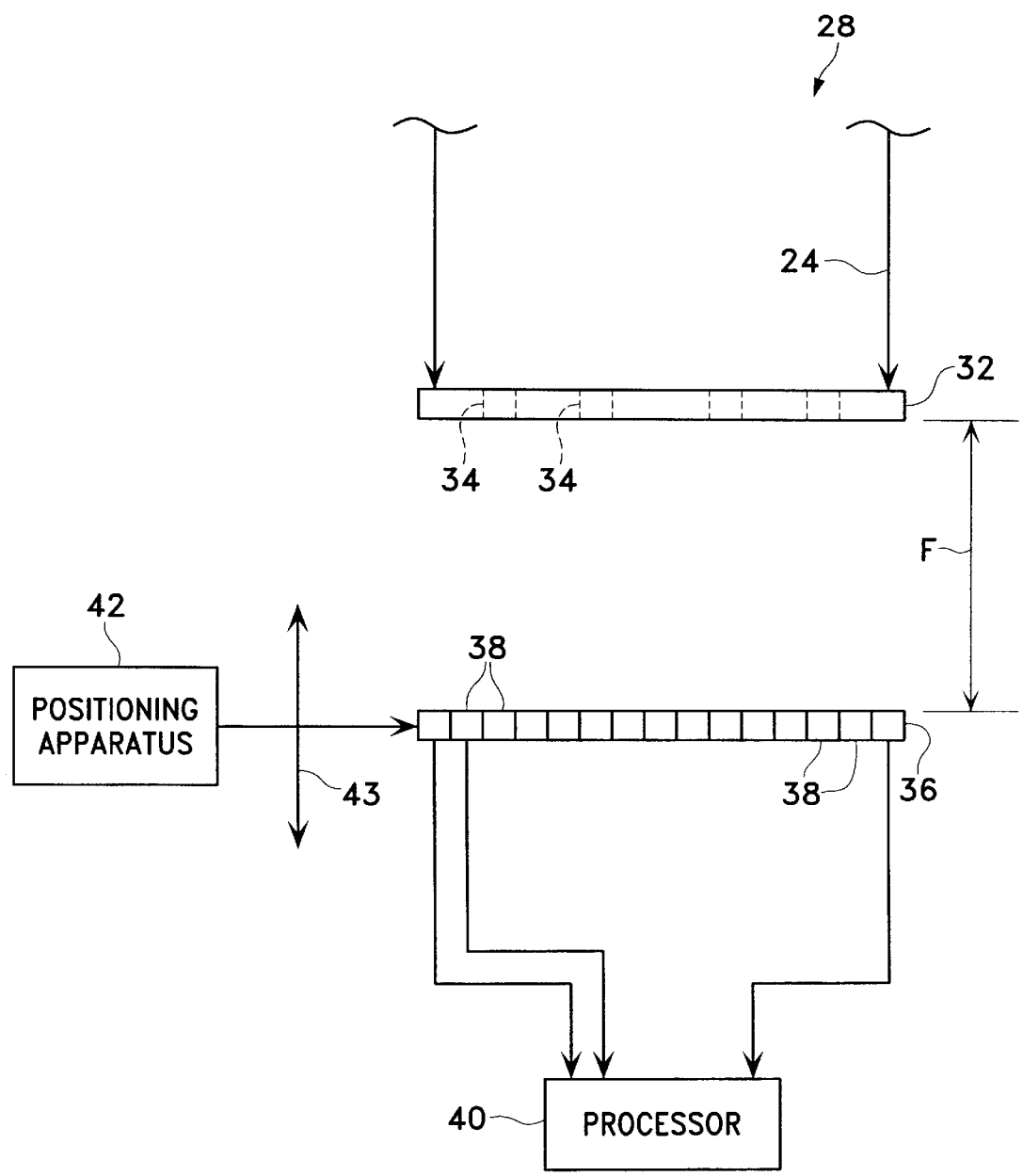
FIG. 3 is a schematic of one embodiment of a Hartmann-Shack wavefront analyzer used in the present invention.
Figure 4:
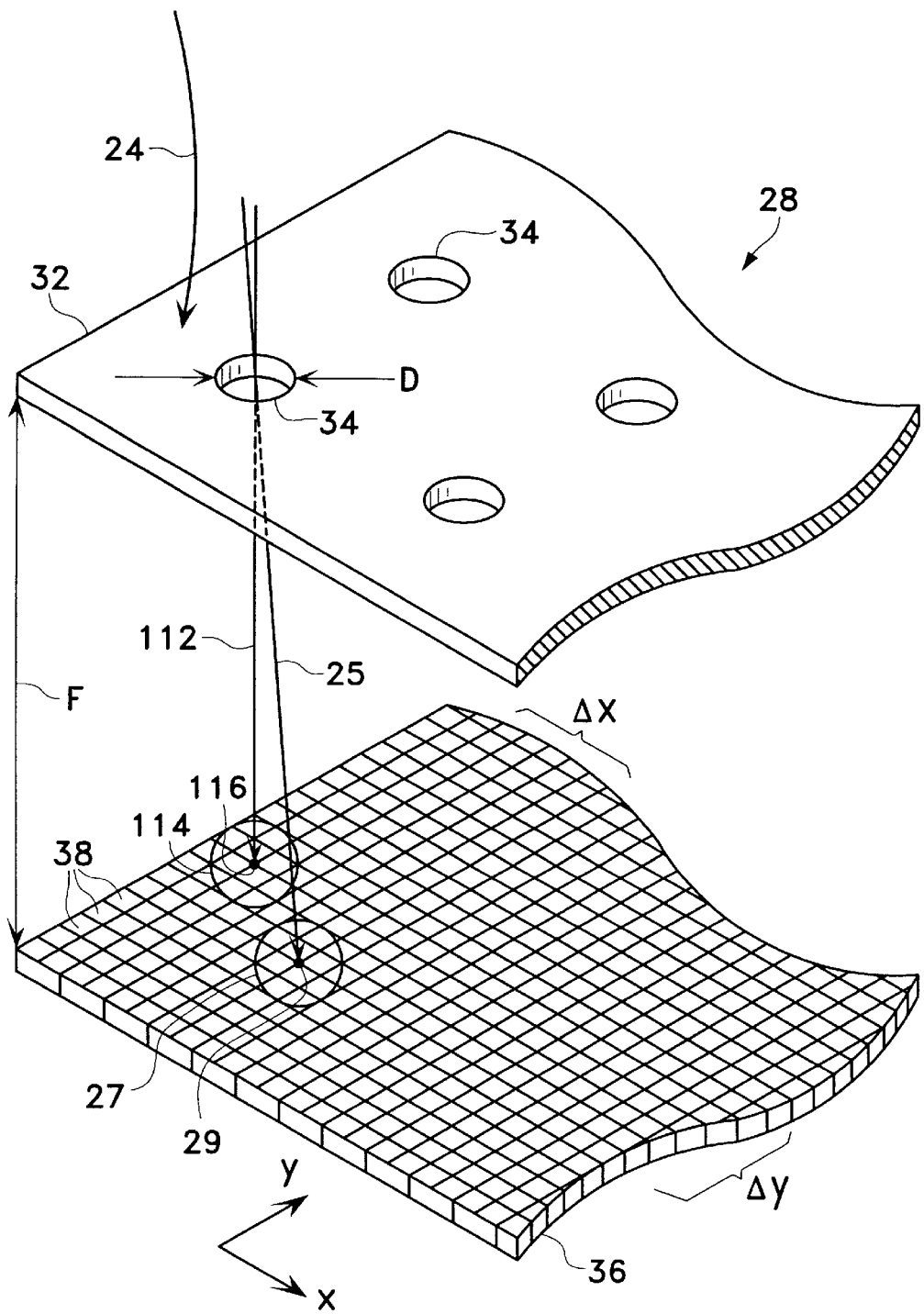
FIG. 4 is a perspective view of a portion of the pinhole imaging plate and planar array of light-sensitive cells comprising the wavefront sensor from the embodiment of FIG. 3 where the deflection of a wavefront piece associated with an aberrated eye is shown in comparison with a wavefront piece associated with a calibration or planar wavefront.

The dynamic range of the apparatus 10 is further improved by providing an improved wavefront sensor arrangement 28 as illustrated with reference to FIGS. 3 and 4. The wavefront analyzer 26 includes an opaque imaging plate 32 having an array of holes 34 passing therethrough, a planar array 36 of light-sensitive cells such as charge coupled device (CCD) cells 38, and a processor 40 operable with the planar array 36 of the CCD cells 38. The combination of the plate 32 and the planar array 36 provides one embodiment of the present invention. The plate 32 is held parallel to and spaced from the planar array 36 by a separation distance F. As will be explained further below, the separation distance F can be varied to adjust for signal gain. To do this, the planar array 36 is coupled to a positioning apparatus 42, e.g., a conventional motorized linear positioner having precise movement capability, that adjusts the position of planar array 36 relative to the plate 32 for changing the separation distance F as indicated by arrow 43. With respect to the array of holes 34, each of the holes 34 are of equal size and shape with a circle being typical owing to its ease of manufacture. As herein described by way of example, a square array geometry is used for the array of holes 34, although other array geometries will be used without departing from the teachings of the present invention.

As illustrated with reference to FIG. 4, when the wavefront 24 impinges on the plate 32, a portion of the wavefront 24, indicated by arrow 26, passes through the hole 34 to illuminate planar array 36. To a first order, the resulting image formed by each such wavefront portion 25 is a positive shadow of the respective hole 34. However, diffraction occurs as determined by the diameter D of each hole 34, the wavelength λ of the light source (e.g. the wavefront 24) and the separation distance F between the plate 32 and the planar array 36. The value of F is varied by the positioning apparatus 42 to adjust the gain based on the particular patient as will be explained further below.

Note that performance of the plate 32 with holes 34 may also be accomplished using a solid plate or film made from a light-sensitive material such as a photo-lithographic film. In such a case, the array of holes 34 would be replaced by an array of shaped light transmissive apertures through which light passes when impinging thereon. The remainder of such a plate or film would be impervious to light. Such an embodiment permits the light transmissive apertures to be easily made to conform to any desired shape.

Regardless of how each wavefront portion 25 is generated, the present invention measures the amount of angular deflection of each wavefront portion 25 relative to a wavefront portion 112 that results from a calibration wavefront such as the planar wavefront earlier described. The calibration or planar wavefront of light results in the wavefront portion 112 impinging at a normal or perpendicular to plate 32 and illuminates a geometric spot 114 on the planar array 36. In contrast, continuing with the wavefront 24 representing a distorted wavefront as described above, the wavefront portion 25 will exhibit an amount of angular deflection relative to the calibration wavefront portion 112. The angular deflection causes the wavefront portion 25 to illuminate a geometric spot 27 on the planar array 36 that is offset from the spot 114. In terms of the present invention, the amount of offset is measured relative to centroids 116 and 29 of spots 114 and 27, respectively. In the two dimensions of the planar array 36, the centroid 29 is typically deflected in both the x and y directions of the array 36. Thus, the angular deflection in each of the x and y directions is given by $\Delta x/F$ and $\Delta y/F$, respectively.

With reference again to FIG. 2, the lenses 220 and 224 in one embodiment are identical as mentioned above. However, in certain applications it may be desirable to magnify or minify the wavefront at the wavefront sensor. This can be accomplished by using lenses 220 and 224 of different focal lengths and adjusting dimensions of the apparatus 10 accordingly. For ophthalmic evaluation, the object plane of the apparatus should ideally be tangent to the corneal surface which can be achieved by a variety of means. Thus, each point at the object plane of the optical train 22 very nearly corresponds to the same point on the cornea 126. However, since the cornea 126 is curved, there will be a slight lateral displacement. The plate 32 described earlier with reference to FIG. 4 of the wavefront analyzer 26, or an imaging plane of any wavefront sensor portion, is positioned at the focal plane of lens 220. In this way, the object plane is always imaged on the plate 32 in direct correspondence with the wavefront image emerging from cornea 126. This will be true regardless of the optical path length between the lenses 220 and 224. There are several advantages to this structure, one of which is that there are very good planar arrays of light-sensitive cells that are commercially available to image an area corresponding to the 6 millimeter central circular region of the cornea.

The plate 32 (or the imaging plane of any wavefront sensor portion of a wavefront analyzer) breaks the wavefront 24 into wavefront pieces that can each be measured independently in terms of propagation direction at the planar array 36. Since in an embodiment herein described by way of example, the optical train 22 does not magnify or reduce the image in the object plane, a point at the object plane corresponds to the same point at the image plane of the optical train. With the Porro mirror 222 set at its zero position, the direction each portion of the wavefront 24 is traveling toward the object plane is reproduced exactly at the image plane of wavefront analyzer 26. By way of example, if one wavefront portion at a location in the object plane was traveling away from the optical axis at an angle of 20° with respect to the optical axis that is perpendicular to the object plane, the wavefront portion at the same location in the image plane will also be traveling away from the optical axis at an angle of 20°.

Note that a person who is myopic will produce a wavefront such that the wavefront portions/pieces isolated by the plate 32 will converge toward the center of planar array 36. A hyperopic person will produce a wavefront such that the wavefront pieces isolated by the plate 32 diverge. Thus, a person with a significant vision error becomes difficult to evaluate because wavefront portions can either overlap (myopia) at the planar array 36 or spill off (hyperopia) the planar array.

In the present invention, five ways of compensating for such severe aberrations are herein described by way of example. The first way is to utilize a wavefront sensor with sufficiently small light sensitive cells 38 and sufficiently large holes 34 (or any other transmissive aperture). In this way, measurement of each wavefront piece can be performed to an acceptable accuracy using a small value for F. A second way is to move planar array 36 along the optical axis to change the separation distance F to the plate 32. For a person with a severe aberration, the planar array 36 is positioned close to the plate 32 to keep the projected wavefront portions well separated and on the planar array. For a mild aberration, the planar array 36 is moved to increase the separation distance F to the plate 32 to make a more accurate measurement. The advantage of moving the planar array 36 to change the separation distance F to the plate 32 is that the wavefront analysis is easily achieved for any position. Yet another way of compensating for severe aberrations using the present invention is to change the optical path length between lenses 220 and 224. Moving the Porro mirror 222 will not affect where the wavefront hits the plate 32, but will change the angular deflections at which the projected wavefront portions pass through the plate 32, i.e., $\Delta x/F$ and $\Delta y/F$. Decreasing the optical path length between lenses 220 and 224 will tend to pull the wavefront portions toward the center of planar array 36 thereby compensating for hyperopia. Increasing the optical path length between lenses 220 and 224 will tend to spread the wavefront portions toward the edges of the planar array 36 thereby compensating for myopia. The degree to which the angular deflection associated with each wavefront piece is altered is a linear function of its distance off the optical axis and the movement of the Porro mirror 222 from its zero position. A fourth way of compensating for severe aberrations is to insert one or more trial lenses of specified sphero-cylindrical power at the location of the intermediate focal plane, as will be discussed in detail later in this section. This serves to reduce or remove low order aberrations from the wavefront so that displacement of spots at the CCD cells 38 is minimized and accurate evaluation can proceed. The effect of the specified lens addition is then included in the final wavefront reconstruction. A fifth way is to increase the magnification of the wavefront at the wavefront sensor relative to that at the eye. This is accomplished by an appropriate choice of lenses in the relay optic design. Magnification will reduce the slope of the wavefront uniformly, thereby reducing the displacement of each spot at the CCD.

Figure 5:
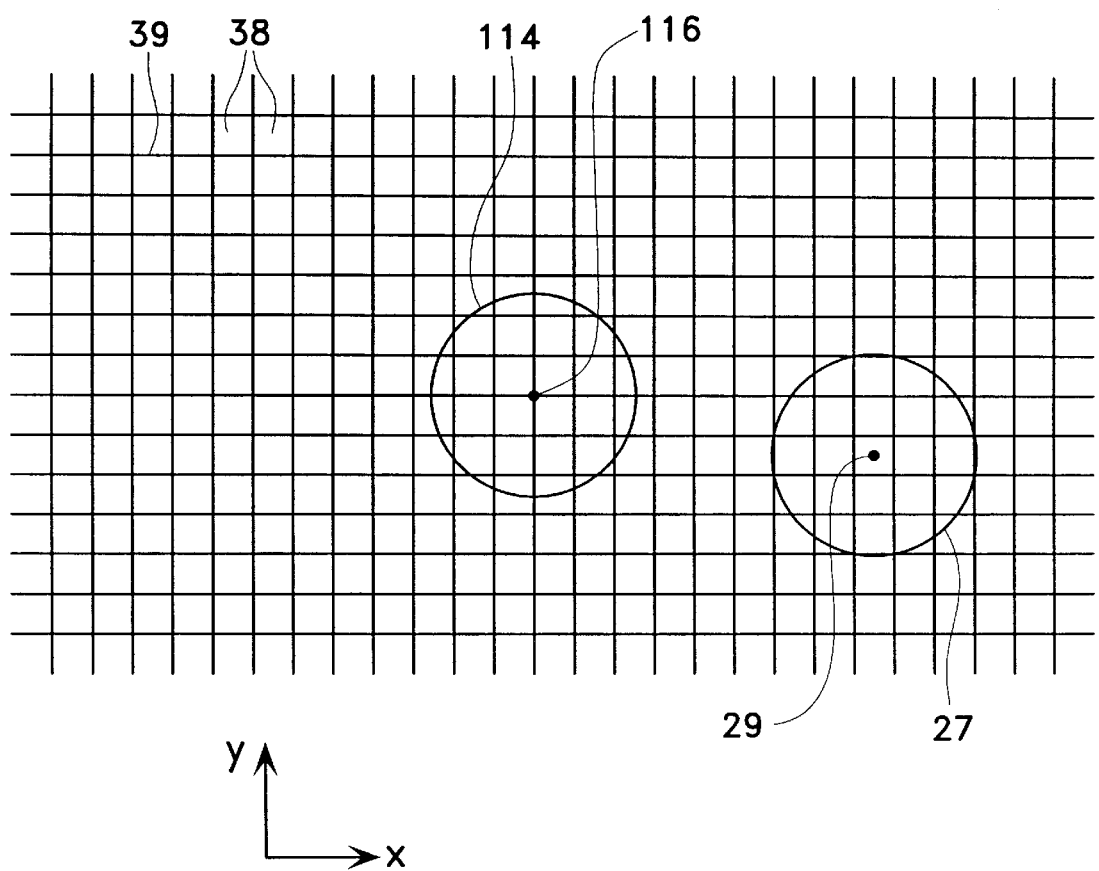
FIG. 5 is a plan view of a designated area on the planar array of light-sensitive cells associated with a corresponding hole.

By way of example, to accurately determine the centroid 29 of the spot 27 of light impinging on the planar array 36, a fine structure of cells 38 relative to a spot size is provided. Each spot covers a plurality of cells 38. One method used to determine the centroid 29 of each spot 27 unambiguously with respect to a spot caused by another one of the holes 34, assigns a unique number of cells 38 to each hole 34. The "assigned areas" are designated, as illustrated with reference to FIG. 5, by way of example, with the heavy grid lines 39. It is to be understood that the grid lines 39 are not actual physical boundaries between cells 38 but are shown simply to illustrate the unique designated areas containing a plurality of the cells 38. It is anticipated that other centroid strategies will be utilized that do not necessitate such partitioning of the array 36 given the teachings of the present invention. An alternative method for identifying and correlating centroids is later described in this section.

Figure 6:
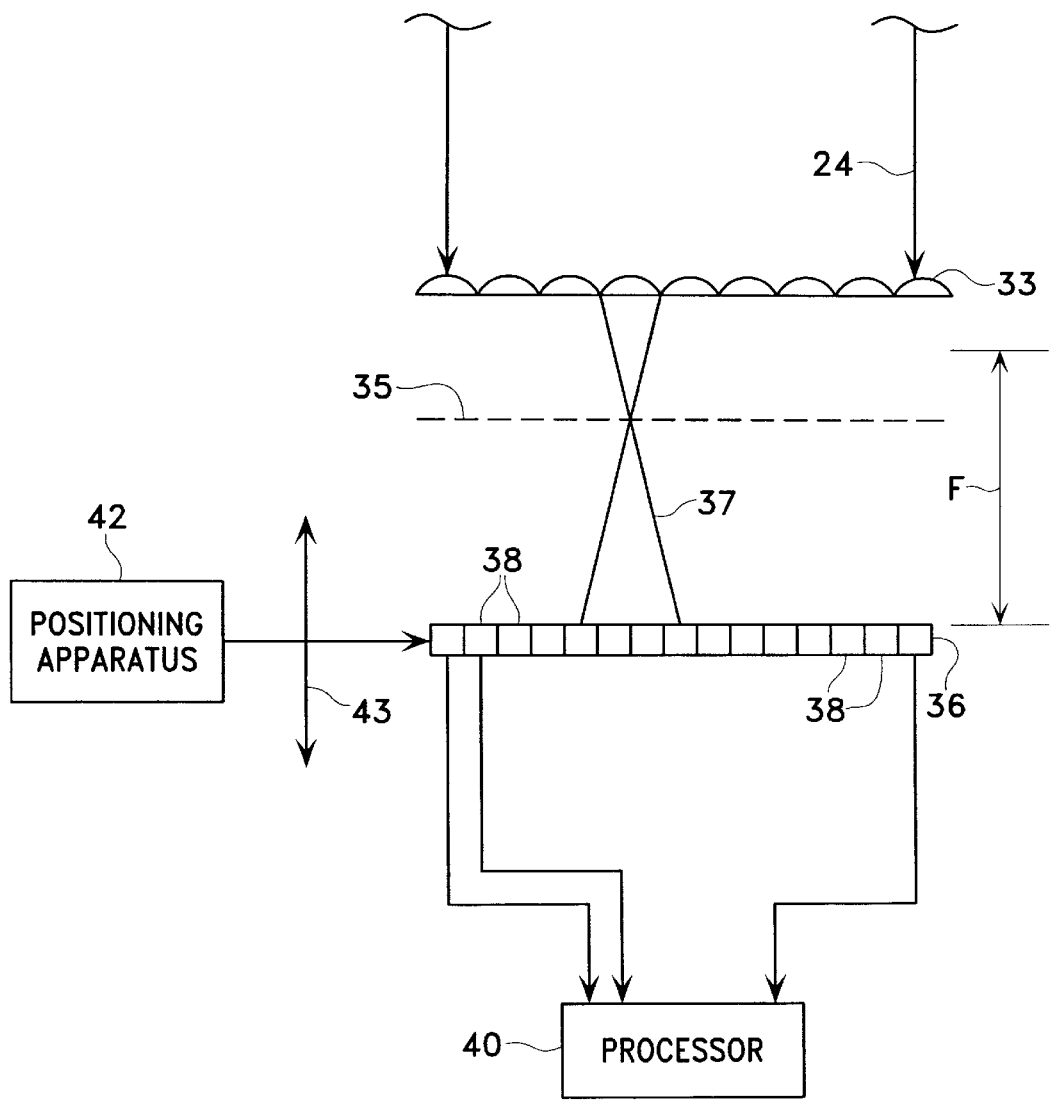
FIG. 6 is a schematic of another embodiment of a wavefront analyzer used in the present invention.

By way of example, the present invention could also be practiced with a wavefront analyzer that replaces plate 32 described with reference to FIG. 3, with a two dimensional array of identical spherical lenslets 33, as illustrated with reference to FIG. 6. In such an embodiment, the lenslet array 33 may be operable by the positioning apparatus 42 such that separation distance F is independent of the focal length f that defines the focal plane of the lenslet array 33 which is represented by dashed line 35. Each wavefront portion 37 passed through a sub-aperture of the lenslet array 33 is reduced in size (e.g., diameter) but is not necessarily brought to a minimum focus at the planar array 36 as it would be if separation distance F were equal to focal length f. In the operation of this embodiment configuration, the lenslet array 33 is positioned to concentrate the light in each wavefront portion of an area for providing sufficient intensity onto the planar array 36, yet still illuminating a substantial plurality of cells 38 for greatest accuracy in determining the deflection of the centroids 29.

Regardless of the structure of the wavefront sensor, the processor 40 computes each two-dimensional centroid 29 of each spot 27 generated by the wavefront 24. The amount of two dimensional centroid shift relative to the centroid of the calibrating spot for each designated area associated with a corresponding hole 34 (or sub-aperture of lenslet array 33) is divided by the separation distance F to generate a matrix of local slopes of the wavefront, i.e., $\partial W(x,y)/\partial x$ and $\partial W(x,y)/\partial y$ at the (x,y) coordinates of the centers of holes 34. For simplicity of discussion, these will be indicated by $P(x,y)=\partial W(x,y)/\partial x$ and $Q(x,y)=\partial W(x,y)/\partial y$, respectively.

Numerous methods exist for using the partial derivative data to calculate the distorted wavefront 130 and 24 as described above with reference to FIGS. 1B and 2. One acceptable approach is that described by Liang et al. in the aforementioned Journal of the Optical Society of America paper, where the wavefront is approximated using Zernike polynomials. This is a standard analytic technique described in numerous optics texts such as "Principles of Optics, 11 by M. Born and E. Wolf, Pergamon Press, Oxford, England, 1964. By way of example, the Zernike polynomial approach will be discussed herein. However, it is to be understood that other mathematical approaches can be used in approximating the distorted wavefront. By way of example, such approaches may include the use of Fourier series and Taylor series.

$$W(x, y) = \sum_{i=0}^{n} C_i Z_i(x, y) \tag{4}$$

Briefly, the wavefront W(x,y) is expressed as a weighted sum of the individual polynomials where $C_i$ are the weighting coefficients, and $Z_i(x,y)$ are the Zernike polynomials up to some order. The upper limit n of the summation is a function of the number of Zernike polynomials, i.e., the highest order, used to approximate the true wavefront. If m is the highest order used, then $$n=(m+1)(m+2)/2 \tag{5}$$

Derivation of the Zernike polynomials up to an arbitrary order n is described in numerous optical texts such as the aforementioned book by Born and Wolf. One possible method of determining the centroid 29, 116 of a spot 27, 114, respectively, as earlier described with reference to FIGS. 4 and 5, and calculation of the Zernike weighting coefficients will now be explained. The directions of the unit normals at the center of each hole 34 are based on the centroids of the spots on cells 38. Since each spot will illuminate a plurality of cells varying intensity, a standard amplitude-weighted centroid calculation can be used to find the center of each spot. In order to clearly delineate each centroid from background noise, by way of example, resulting from spurious light reaching the CCD surface between valid spots, standard mathematical techniques such as a matched spatial filter can be applied to the CCD data prior to centroid identification.

An alternative method is herein described for identifying individual spots and correlating their geometry. The apparatus is configured such that the optical axis is aligned to the center of a particular aperture at the entrance face of the wavefront sensor. This aperture is located at or near the center of the entrance face. If the probe beam entering the eye is also aligned to the system optical axis, then due to the reversible nature of light rays, a light spot will always be seen directly behind the aligned aperture. That is, a spot will always be seen on the CCD sensor at this location, regardless of the wavefront aberrations, and will always correspond to the overlying aperture. Immediately adjacent spots will be minimally displaced from their zero slope" locations. As one moves further from the central reference spot, generally greater spot displacements will occur. Using this knowledge, it is a relatively straight forward process to identify all the spots in the CCD pattern and establish their geometric relationships.

The displacement of the centroid from that of a perfectly collimated light beam, corresponding to ideal and emmetropic vision, is then calculated and used to determine the wavefront slope at each sample location. The location of the centroids for a collimated light beam may either be directly measured in a calibration step prior to the patient exam, or taken from a calculated reference pattern based on the wavefront sensor construction.

Multiple exposures may be used to check for improper eye alignment or eye movement during individual exposures. If eye movement during exposures cannot be analyzed successfully by acquiring multiple exposures, then the apparatus 10 can be augmented by the addition of an eye tracker 25, illustrated with reference again to FIG. 2. One possible placement of the eye tracker 25 is herein illustrated. However, it is to be understood that the eye tracker 25 could be placed elsewhere within the apparatus 10. In this way, wavefront analysis is performed even during a limited amount of eye motion.

A one-time calibration exposure can also be used to determine the relative sensitivities of the individual cells. This is made in uniform collimated light with plate 32 removed. The responses of individual cells are then recorded. For each light transmissive aperture (e.g., hole 34), the centroid in the collimated case serves as a dedicated origin for the particular hole. The shift from the "origin" for each hole to the centroid caused by the wavefront 24 (as observed in this coordinate system) is determined by the direction of the wave surface corresponding to that hole. If $\Delta x(m,n)$ is the x-component of the (m,n)th centroid and F is the plate separation, then the P-value for the (m,n)th centroid is:

$$P(m,n)=\partial x(m,n)/\partial z=\Delta x(m,n)/F \qquad (6)$$

The corresponding expression for Q is:

$$Q(m,n)=\partial y(m,n)/\partial z=\Delta y(m,n)/F \qquad (7)$$

Thus, each P(m,n) and Q(m,n) represents the partial derivatives of W(x,y) with respect to x and y for the (x,y) coordinates of each hole 34. For an m-order Zernike approximation of the original wavefront, the experimentally determined P's and Q's are then used in the following equations to calculate the appropriate $C_i$ weighting coefficients as follows:

$$P(m, n) = \frac{\partial W(x, y)}{\partial x} = \sum_{i=0}^{n} C_i \frac{\partial Z_i(x, y)}{\partial x} \qquad (8)$$

$$Q(m, n) = \frac{\partial W(x, y)}{\partial x} = \sum_{i=0}^{n} C_i \frac{\partial Z_i(x, y)}{\partial x} \qquad (9)$$

By using a least-squares approx(m,n)/∂zach to minimize the error between the actual wavefront slopes on the left hand side in the above equations and the Zernike approximations on the right hand side, optimal values for the weighting coefficients can be obtained.

In one possible approach to calculating a centroid $(x_c, y_c)$ each hole 34 is assigned its dedicated area of the array 36 or $(i_{m,n} \pm \Delta i, j_{m,n} \pm \Delta j)$. This square of many light-sensitive cells is large enough that neighboring hole images never encroach, and all illumination from this hole is contained. The square contains $4\Delta i * \Delta j$ cells.

If array 36 is designated $C_{k,1}=(x_c(i,j),y_c(i,j)),k, 1=0 \ldots 2\Delta 1, 2\Delta j$, and the spacing on centers is $\Delta x=\Delta y=d$, the measured cell responses are V (k,1) and the relative responsivities are R (k, I), then the x-component $x_c$, a function of i, j is represented by $$x_c(i,j)=[\Sigma_{k,1}V(k,1)*R(k,1)*d*k]/[\Sigma_{k,1}V(k,1)*R(k,1)] \qquad (10)$$

and the y-component $y_c$, as a function of i,j is represented by $$y_c(i,j)=[\Sigma_{k,1}V(k,1)*R(k,1)*d*1]/[\Sigma_{k,1}V(k,1)*R(k,1)] \qquad (11)$$

Then, if $(x_{c0}(i,j),y_{c0}(i,j))$ is the "origin centroid" for the (i,j) hole, i.e., made in perpendicular collimated light, and $(x_{cw}(i,j),y_{cw}(i,j))$ is the corresponding centroid found for the wavefront to be measured, then the relative centroid shift $(x_{cr}(i,j)), Y_{cr}(i,j))$ is found as $$x_{cr}(i,j)=x_{cw}(i,j)-x_{c0}(i,j) \qquad (12)$$

$$y_{cr}(i,j)=y_{cw}(i,j)-y_{c0}(i,j) \qquad (13)$$

The values P(i,j) and Q(i,j) are determined from $$P(i,j)=x_{cr}(i,j)/F \qquad (14)$$

and $$Q(i,j)=y_{cr}(i,j)/F \qquad (15)$$

The surface partial derivatives P(i,j) and Q(i,j) for the array of hole centers of plate 32 are next used to calculate the appropriate Zernike polynomial weighting coefficients to describe the original wavefront W(x,y). This will now be explained by way of illustration for a 7×7 square array of holes 34. However, it is to be understood that other sizes and shapes of hole arrays could be used.

First, a 1×98 matrix (i.e., column vector) PQ(k) is formed as $$PQ(k)=P(7i+j),j=0 \ldots 6,i=0 \ldots 6,k=0 \ldots 48 \qquad (16)$$

$$PQ(k)=Q(7i+j),j=0 \ldots 6,i=0 \ldots 6,k=49 \ldots 98 \qquad (17)$$

with j cycling for each i, i.e., PQ (18)=P (2,5).

The matrix PQ is multiplied from the left with a transition matrix TM to get the matrix C as follows $$C=TM*PQ \qquad (18)$$

where TM is a 98 wide by 14 high matrix and C is a 1 wide by 14 high matrix or column vector. C is the matrix $C_k$ k=1, ... , 14 such that, to a least square error, $$W(x,y)=\Sigma_k C_k * Z_k(x,y) \qquad (19)$$

and TM is calculated for a given aperture, e.g., a 6 millimeter pupil aperture. The functions $Z_k$ (x,y) in equation (19) are the Zernike polynomials. There is no standard convention as to their sequence. Thus, for consistency, it is important that the same sequence is used to produce the set $C_k$ that was chosen for deriving the matrix TM. They occur in groups of the same order, which is the highest exponent in the group, with the total number of members in an order increasing with the order. For example, in a fourth order analysis, orders up to and including 4 are used (less $Z_0$—the single member of order 0 that is the constant 1 which describes the reference position of the group in the z direction). Since wavefront 24 is moving along z (at the velocity of light), this "piston term" describes only an arbitrary offset in Z, and this term may be ignored. The first 5 orders (0, 1, . . . , 4) contain 15 functions including the piston term.

Thus, in the illustrated example, 14 values of $C_k$ are calculated as coefficients of 14 Zernike polynomials. By way of example, one such order used to calculate TM is herein illustrated, and includes both the Zernike functions and their partial derivatives. ZERNIKE (X,Y) POLYNOMIAL EXPANSION THROUGH ORDER 4

| Polynomial Order 0 | |
|---|---|
| Z(0) | +1 |
| dZ(0)/dx | 0.0 |
| DZ(0)/dy | 0.0 |
| Polynomial Order 1 | |
| Z(1) | +y |
| dZ(1)/dx | 0.0 |
| dZ(1)/dy | +1 |
| Z(2) | +x |
| dZ(2)/dx | +1 |
| dZ(2)/dy | 0.0 |

-continued

| Polynomial Order 2 | |
|---|---|
| Z(3) | $-1 + 2y^2 + 2x^2$ |
| dZ(3)/dx | $+4x$ |
| dZ(3)/dy | $+4y$ |
| Z(4) | $+2xy$ |
| dZ(4)/dx | $+2y$ |
| dZ(4)/dy | $+2x$ |
| Z(5) | $-y^2 + x^2$ |
| dZ(5)/dx | $+2x$ |
| dZ(5)/dy | $-2y$ |

| Polynomial Order 3 | |
|---|---|
| Z(6) | $-2y + 3y^3 + 3x^2y$ |
| dZ(6)/dx | $+6xy$ |
| dZ(6)/dy | $-2 + 9y^2 + 3x^2$ |
| Z(7) | $-2x + 3xy^2 + 3x^3$ |
| dZ(7)/dx | $-2 + 3y^2 + 9x^2$ |
| dZ(7)/dy | $+6xy$ |
| Z(8) | $-y^3 + 3x^2y$ |
| dZ(8)/dx | $+6xy$ |
| dZ(8)/dy | $-3y^2 + 3x^2$ |
| Z(9) | $-3xy^2 + x^3$ |
| dZ(9)/dx | $-3y^2 + 3x^2$ |
| dZ(9)/dy | $-6xy$ |

| Polynomial Order 4 | |
|---|---|
| Z(10) | $+1 - 6y^2 + 6y^4 - 6x^2 + 12x^2y^2 + 6x^4$ |
| dZ(10)/dx | $-12x + 24xy^2 + 24x^3$ |
| dZ(10)/dy | $-12y + 24y^3 + 24x^2y$ |
| Z(11) | $-6xy + 8xy^3 + 8x^3y$ |
| dZ(11)/dx | $-6y + 8y^3 + 24x^2y$ |
| dZ(11)/dy | $-6x + 24xy^2 + 8x^3$ |
| Z(12) | $+3y^2 - 4y^4 - 3x^2 + 4x^4$ |
| dZ(12)/dx | $-6x + 16x^3$ |
| dZ(12)/dy | $+6y - 16y^3$ |
| Z(13) | $-4xy^3 + 4x^3y$ |
| dZ(13)/dx | $-4y^3 + 12x^2y$ |
| dZ(13)/dy | $-12xy^2 + 4x^3$ |
| Z(14) | $+y^4 - 6x^2y^2 + x^4$ |
| dZ(14)/dx | $-12xy^2 + 4x^3$ |
| dZ(14)/dy | $+4y^3 - 12x^2y$ |

The choice of sequencing the Zernike polynomials dictates the interpretations of the $C_k$ in equation (19) and therefore the order of terms in the TM matrix. Hence, the TM matrix is calculated after the choice is made. The development of the TM matrix for the illustrated example will be explained below.

Note that the fourth order analysis is only an example and is not the only possibility. A Zernike analysis can be done to any order. In general, the higher the order, the more accurate the result over the tested points. However, an exact polynomial fit over the tested points is not necessarily desirable. Such fits have the typical disturbing property that, unless the surface itself happens to be an exact polynomial of order no higher than that used for the surface fit, forcing an exact fit at separated points often causes wild swings between fitted points. That is, in polynomial surface fitting, an exact fit at a finite number of points can yield a poor average fit for a general function.

Calculation of the $\Delta z$ (x,y) optical path difference information from the Zernike reconstruction of the wavefront is accomplished simply by subtracting a constant from the Zernike approximation. The value of the constant will depend on the desired characteristics of $\Delta z$ (x,y). Depending on the method chosen to compensate for the aberrations (e.g., lens addition, etc.) it may, for example, be desirable to set either the maximum, mean or minimum value in $\Delta z$ (x,y) equal to zero.

The development of the transition matrix TM will now be explained for the illustrated example of a 7×7 array of holes in plate 32. At each point $(x_i, y_j)$, the tangents of the components of the normal are P $(x_i, y_j)$ and Q $(x_i, y_j)$ where $$P(x_i,y_j)=\partial W(x_i,y_j)/\partial x \quad (20)$$

and $$Q(x_i,y_j)=\partial W(x_i,y_j)/\partial y \quad (21)$$

Combining these with equation (11), $$P(x_i,y_j)=\Sigma_k C_k \partial W(x_i,y_j)/\partial x \quad (22)$$

and $$Q(x_i,y_j)=\Sigma_k C_k \partial W(x_i,y_j)/\partial y \quad (23)$$

each applicable to 49 (i,j) combinations. These are combined into a single column vector PQ that is 98 elements high, i.e., a 98×1 matrix. Defining two matrices $C_k$ (14 high×1 wide) and $M_{k,(i,j)}$ (14 wide×98 high)

$$(M_{k,(i,j)})=\partial Z_k(x_i,y_j)/\partial x; \partial Z_k(x_i,y_j)/\partial y \quad (24)$$

where the x-derivatives are the first 49 rows and the y-derivatives are the last 49 rows. Then, equation (19) can be rewritten as the matrix equation $$(PQ)=(M)(C) \quad (25)$$

where the top 49 rows of M are the $\partial W (x_i, y_j)/\partial y$.

The expression in equation (25) gives the normal components in terms of the Zernike coefficients for a surface described by the array of 14 C's. These are exact, but it is not guaranteed that the actual total surface can be described by such an array of coefficients. Accordingly, if it is assumed that the description is within an acceptable tolerance, i.e., tolerating the errors that remain after least square error determination, then equation (26) can be considered to define the column vector C implicitly in terms of the mathematical matrix M and the measured vector PQ, both of which are known. The method of effecting the solution under the minimization condition is as follows. First, equation (25) is multiplied on the left by MT, the transpose of M such that $$(M^T)(PQ)=(M^T)(M)(C)=(S)(C) \quad (26)$$

where $$S \equiv M^T M \quad (27)$$

is a square and symmetric matrix, e.g., of dimensions 14×14 (with each element the sum of 98 products). Such a matrix has an inverse unless the determinant of its coefficients is zero. Since this is based on the Zernike polynomials alone, and they are all independent of each other, the determinant is non-zero, so that an inverse $S^{-1}$ is defined. Next, equation (25) is multiplied on the left by $S^{-1}$ to yield $$(S^{-1})(M^T)(PQ)=(S^{-1})(S)(C)=(I)(C)=C \quad (28)$$

Then, the mathematical transition matrix (independent of measurement) is $$(TM)=(S^{-1})(M^T) \quad (29)$$

and the "best fit" array of C's from the measured PQ's can be produced by the simple matrix multiplication $$(C)=(TM)(PQ) \quad (30)$$

To evaluate the eye unambiguously, all spots illuminating the planar array 36 due to a wavefront 24 are incident on the planar array simultaneously. If it is desired to reduce effects of eye movement, a pulsing or shuttering laser source may be used, or an eye tracker.

Figure 7:
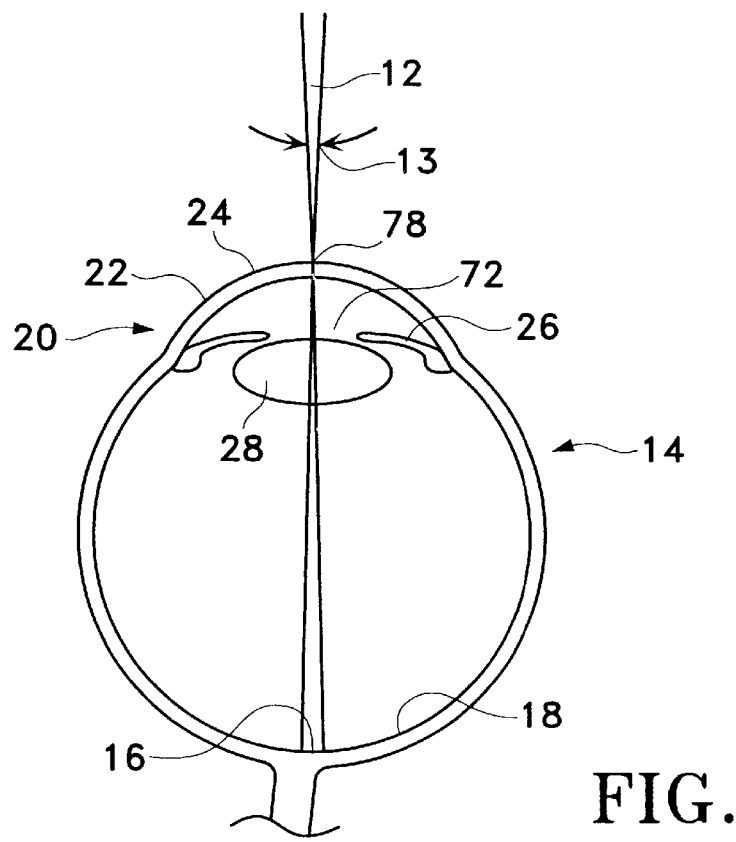
FIG. 7 is a schematic view of an eye to be measured by the present invention.

With reference again to FIGS. 7 and 8, a beam of linearly polarized light (S-component) is emitted from a diode laser (670 nm, 3 mW by way of example), which beam of light passes through an electromechanical shutter, which controls the duration of light exposure on the eye 14 of the patient, and in particular, the exposure of the retina 18 of the eye 14 illustrated with reference again to FIGS. 7 and 8. It is expected that alternate sources of light, for example, non-coherent and non-polarized, as well as alternate light transmitting techniques will come to the mind of those skilled in the art. When the shutter is open, the projected beam, collimated light from the diode laser, is directed by a long focal length lens for focusing on the anterior surface 22 of the cornea 24 of the eye 14, as illustrated with reference to FIG. 7, passing through the pupil 72 and lens 28 of the eye 14, and onto the retina 18 as the small measurable spot 16. In an alternate embodiment, the lens comprises a zoom lens for varying the focus and moving the focus location as desired. By focusing on the cornea 24, the measurement is minimally dependent on the curvature of the cornea. However, other locations proximate the corneal surface are acceptable.

Figure 8:
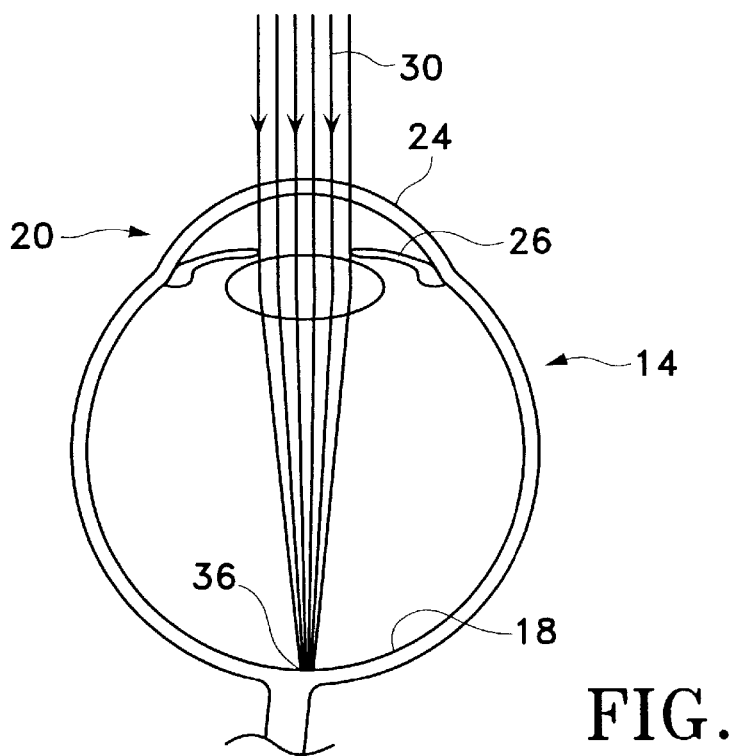
FIG. 8 is a schematic view of an eye to be measured by the present invention.

It is typical in the art of eye measurements to form a collimated beam and attempt to focus the collimated beam onto the retina, using lenses and lens combinations with the optics of the eye to produce the smallest possible spot 36, as earlier described with reference to FIG. 8. Lenses and focusing techniques typically take valuable time and include multiple attempts to focus a spot on the retina using various lenses and lens combinations to accommodate each unique vision of each patient being measured. With this technique, and the understanding that most of the blurring results from the curvature of the cornea, the technique eliminates the need to find lenses or lens combinations to minimize the size of the spot on the retina that is used as the secondary source of radiation.

Figure 9:
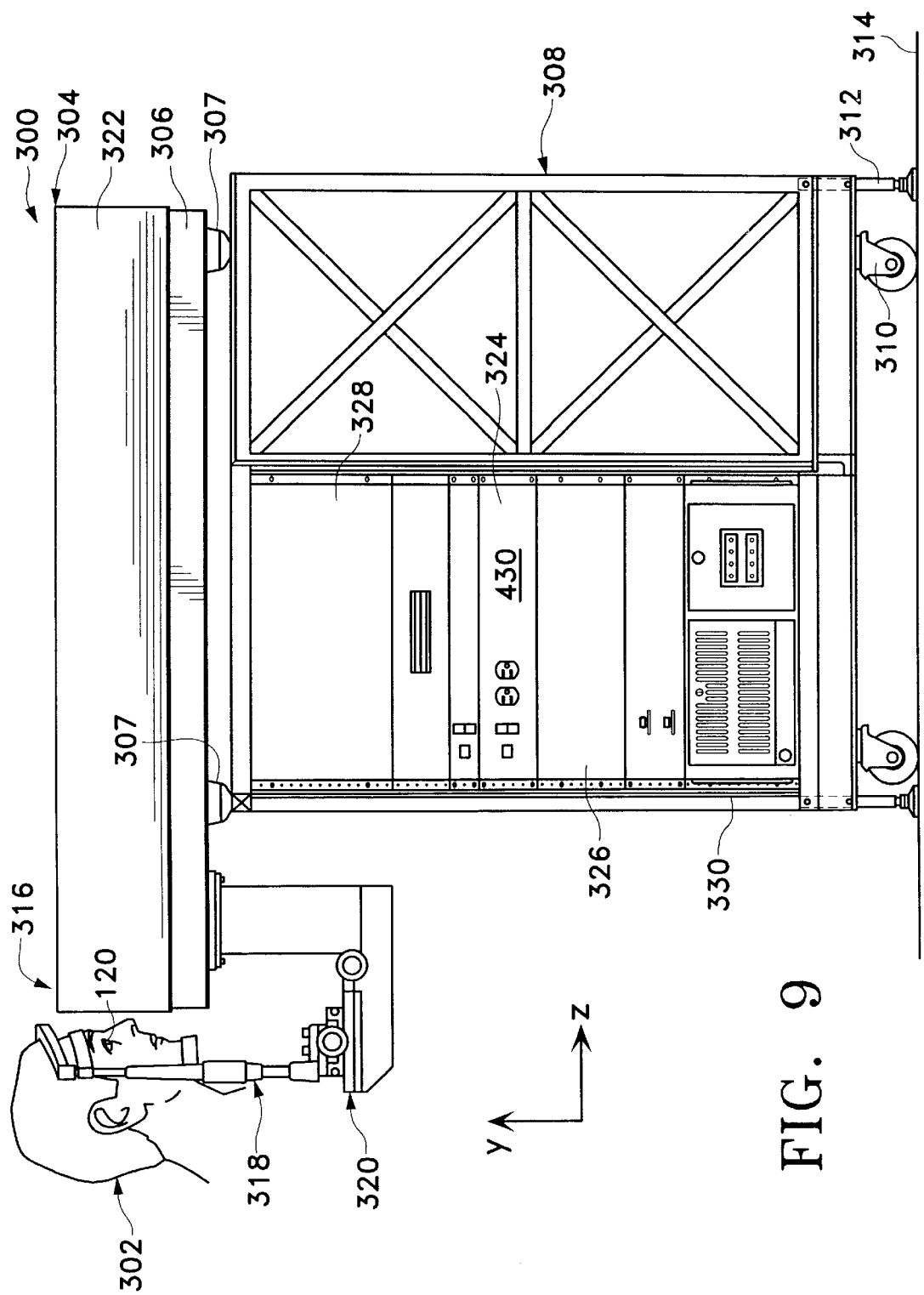
FIG. 9 is a side elevation view of one embodiment of the present invention illustrating a patient positioning for measurement.
Figure 10:
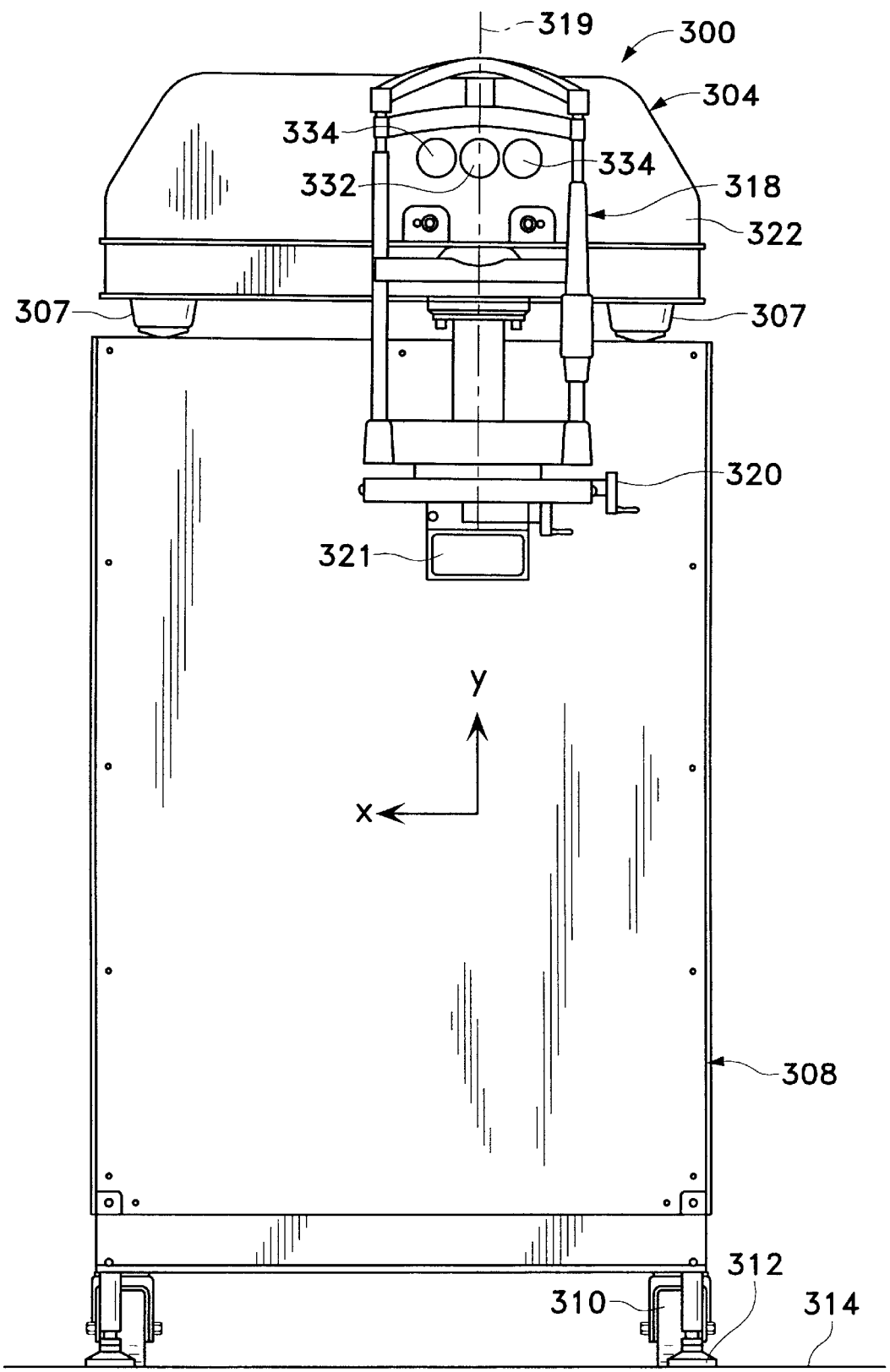
FIG. 10 is an end elevation view of the embodiment of FIG. 9.
Figure 11:
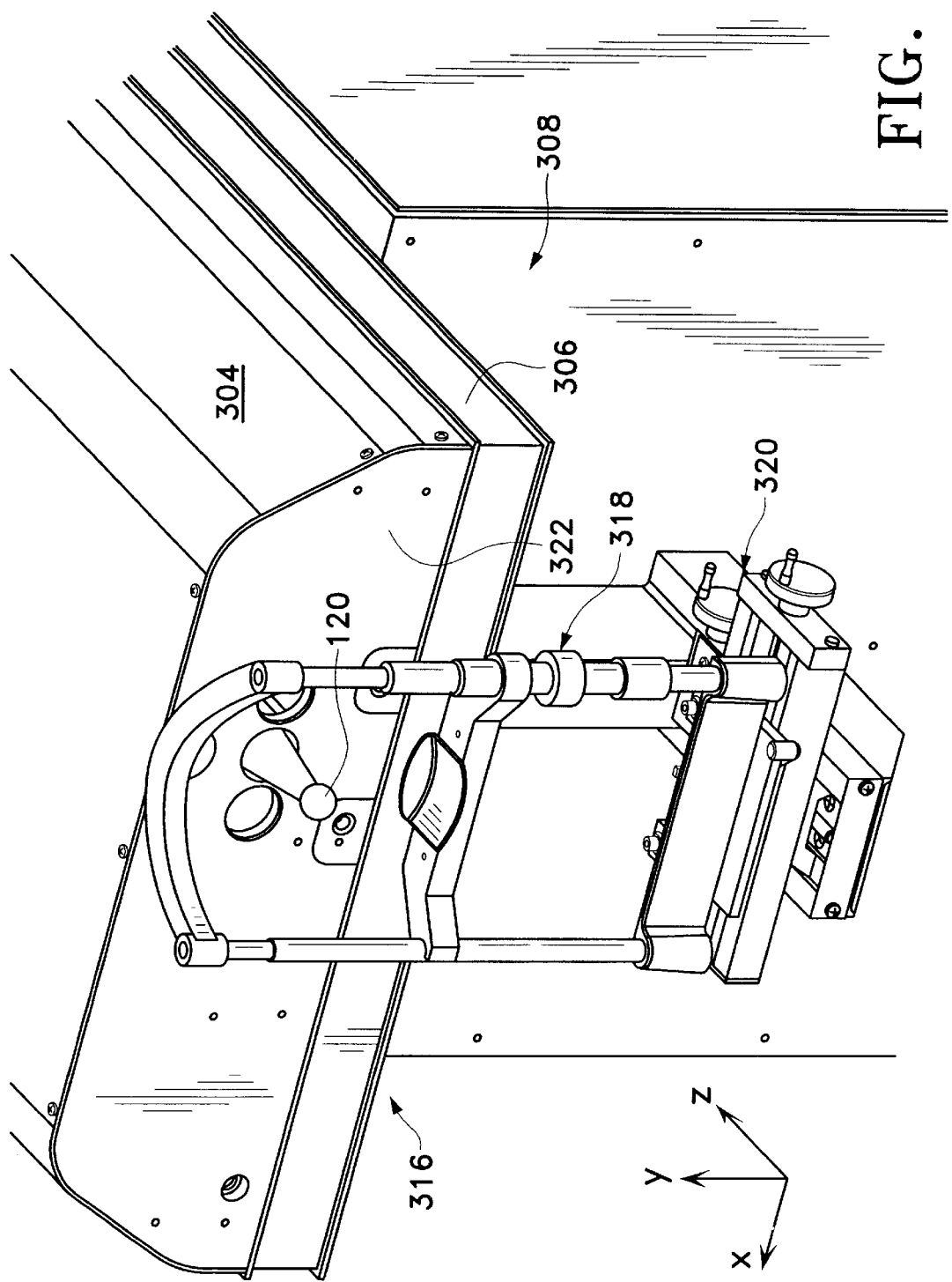
FIG. 11 is an enlarged perspective view of an patient positioning portion of the embodiment of FIG. 9.

With reference now to FIGS. 9–11, an exemplary embodiment of the apparatus 10 will be herein described beginning with series 300, which improved apparatus 300 is constructed as a patient examination station which allows the patient 302 to be comfortably positioned for the measurement of the eye 120, as earlier described. For convenience to the technician operating the apparatus 300, a computer monitor, mouse, and keyboard are located on a separate cart for this embodiment of the present invention, herein described. The apparatus 300 includes a housing 304 having a platform 306 which is carried by a rigid frame 308. The frame 308 includes wheels 310 to facilitate shipping and installation at the clinical site, as well as locking and leveling feet 312 for securing the apparatus to the supporting floor 314. Once the apparatus is positioned, the integrated leveling feet 312 are deployed to provide a stable stationary frame 308, and thus platform 306.

As illustrated, by way of example with reference again to FIGS. 9–11, the patient 302 sits at a patient end 316 of the apparatus 300, with his or her head resting in a headrest 318, which headrest is adjustable in directions left/right (X-direction), up/down (Y-direction), or toward/away (Z-direction) relative to the platform 306, using adjustment assembly 320. The headrest 318 is attached to the lower surface of the platform 306 which forms an optical table for mounting optical components thereon, as illustrated with reference to FIG. 12, and as will herein be described in further detail. The housing 304 includes a removable optical table cover 322 which protects the optical components carried within the housing. The optical table cover 322 is secured to the platform 306 with keyed locks to prevent unauthorized access to the optical components. The platform 306 is bolted to the rigid frame at four locations 307, as illustrated with reference again to FIGS. 9 and 10. The frame 308 also carries electronics 324 and a computer 326 which includes the processor 40 earlier described with reference to FIG. 6, as well as a connector plate for a computer keyboard, monitor and mouse. The frame 308 also includes an upper bay 328 housing electronics controlling optical components carried by the platform 306, and a lower bay 330 housing an uninterruptible power supply (UPS) and an isolation transformer.

As illustrated with reference again to FIGS. 9–12, three ports are positioned within the cover 322, and include an examination port 332 to allow the wavefront measurement of the eye 120 to take place, and two eye illumination ports 334 which allow lamps 336 carried within the housing 304 to illuminate the eye for visualization by an internal video camera 338. In addition, the adjustment assembly 320 includes a position sensor 321 which senses an x-direction displacement for detecting a position of the headrest 318 to the left or to the right of a reference center line location 3191. A signal indicative of the sensed displacement is provided to the computer 326 for automatically recording the appropriate eye 120 (e.g. left or right) being measured.

As illustrated with reference again to FIG. 12, the platform 306 provides an optical table with the patient positioning the eye 120 for measurement by the apparatus 300. The platform surface measures approximately two feet by four feet, with the optical components fixed to the surface using a combination of commercial and customized precision hardware mounts. All transmissive optical elements have surface anti-reflection coating optimized for the selected probe beam wavelength. The optical layout includes five distinct optical pathways which share the optical elements as will herein be described, by way of example. With reference again to FIG. 12, a first optical path 340, a fixation target image optical path illustrated in isolation in FIG. 12A for convenience to the reader, displays a fixation target image to the patient seated at the apparatus 300. The patient aligns his/her visual axis to the optical axis 342 by looking at the center of a target reticle 344 having a grid pattern. With reference again to FIG. 12, a second optical path 346, a video image optical path illustrated in isolation in FIG. 12B for convenience to the reader, captures a video image of the corneal plane. This allows the technician to assist in aligning the eye 120 for examination, and to record the exact location of the eye during each measurement using software reticles superimposed on a video image. With reference again to FIG. 12, a third optical path 348, a probe laser optical path illustrated in isolation in FIG. 12C for convenience to the reader, sends a probe laser beam 350 into the eye 120 along the optical axis 342. As earlier described with reference to FIGS. 2 and 7, the probe laser beam 14, herein referred to with numeral 350 is attenuated to an eye-safe intensity and linearly polarized before being focused onto the corneal surface. With reference again to FIG. 12, a fourth optical path 352, a re-emitted wavefront optical path illustrated in isolation in FIG. 12D for convenience to the reader, conveys the reflected wavefront 24 of FIG. 2, and herein described with numeral 354 re-emitted from the eye 120 and directed towards a wavefront sensor 356. To accomplish this, first and second afocal relay stages 358, 360 transfer the reflected wavefront 354 from the corneal plane of the eye 120 to the entrance face of the wavefront sensor 356. Finally, with reference again to FIG. 12, a fifth optical path 362, a calibration wavefront optical path illustrated in isolation in FIG. 12E for convenience to the reader, injects collimated laser light into the wavefront transfer path leading to the sensor 356. Software operable within the computer 326, described earlier with reference to FIG. 9, uses collimated light wavefront sensor output data to calibrate the apparatus 300 prior to patient measurement.

Figure 12:
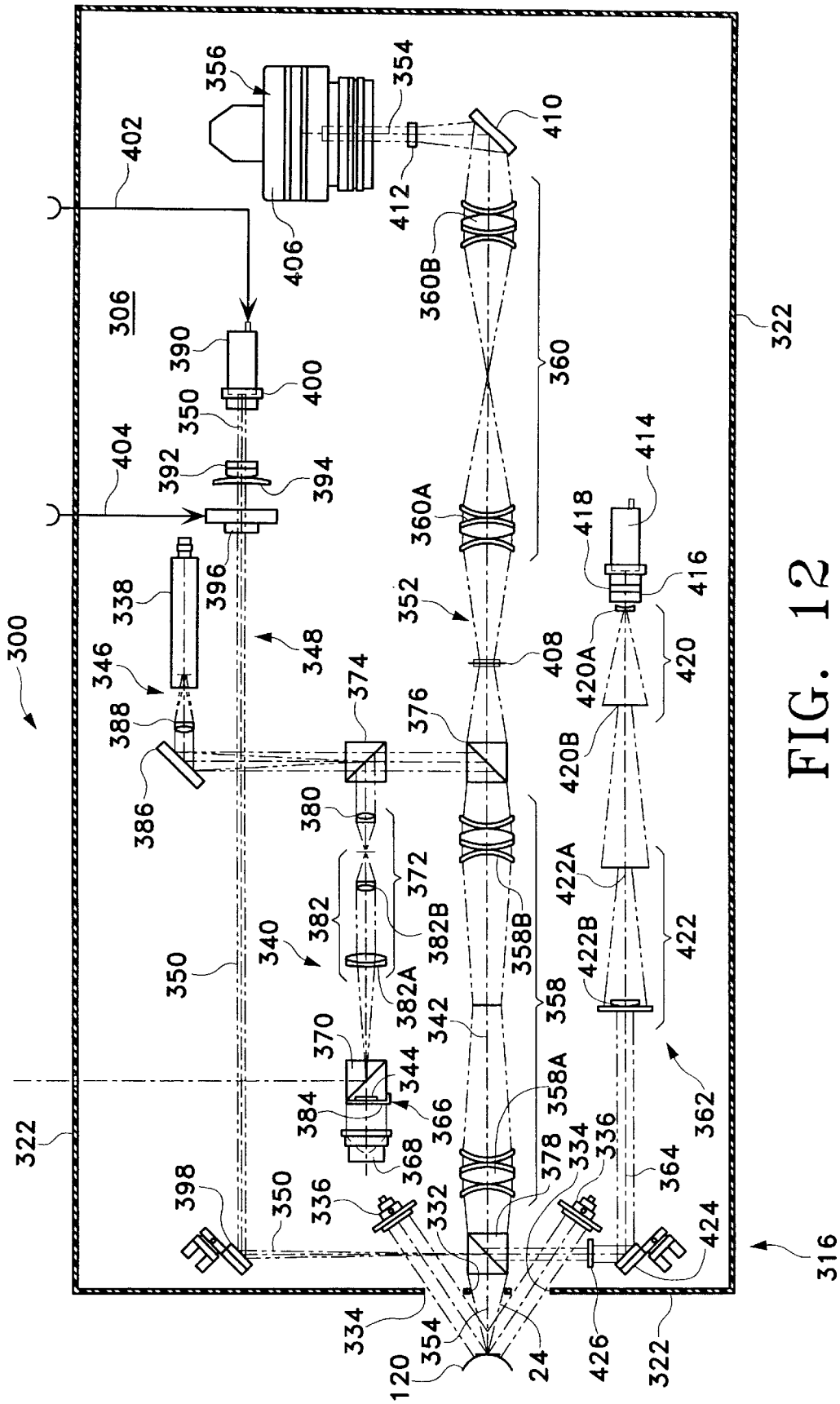
FIG. 12 is a top plan view of optical elements of the embodiment of FIG. 9.
Figure 12A:
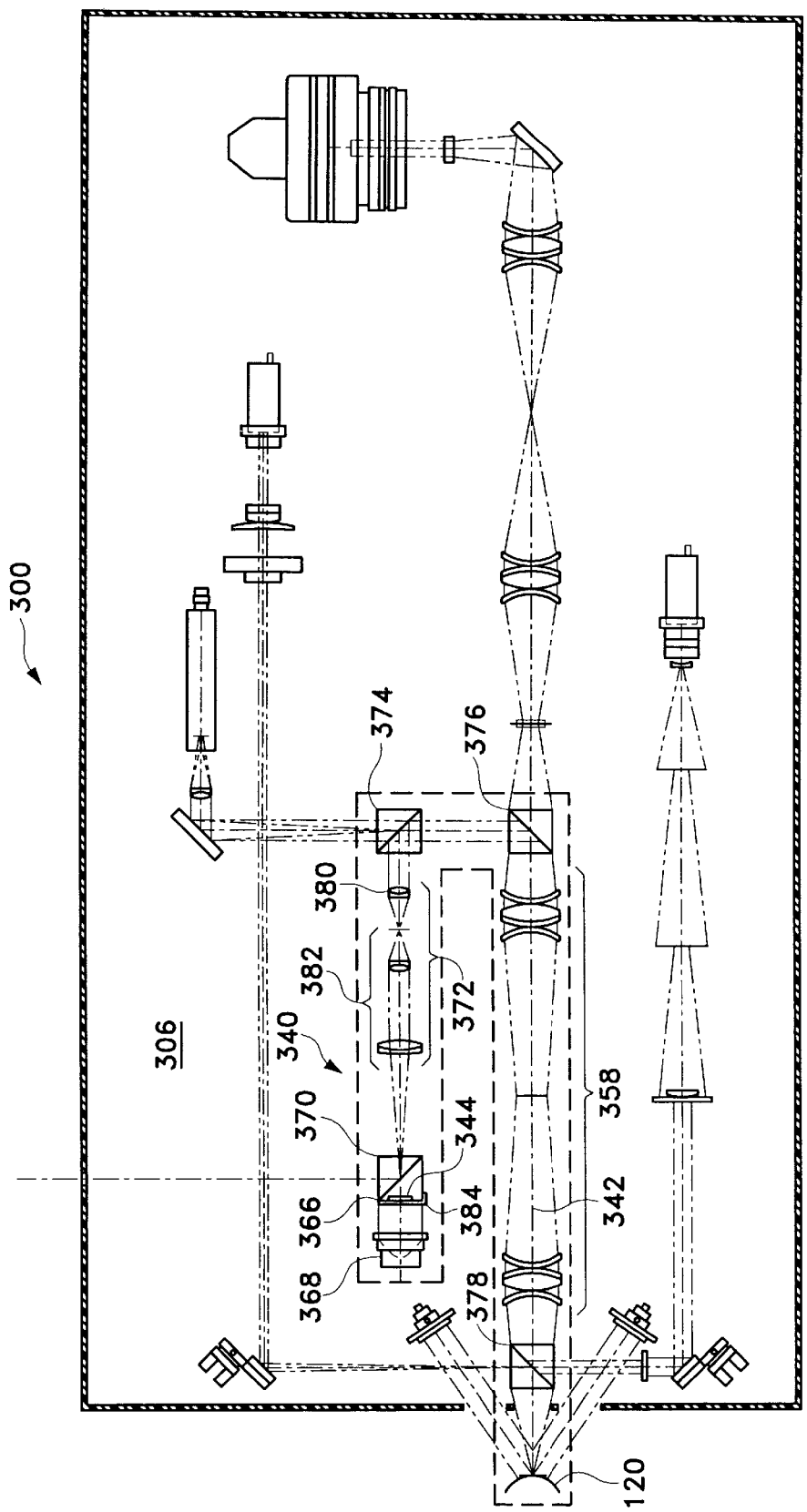
FIG. 12A illustrates a fixation target optical path of FIG. 12.
Figure 12B:
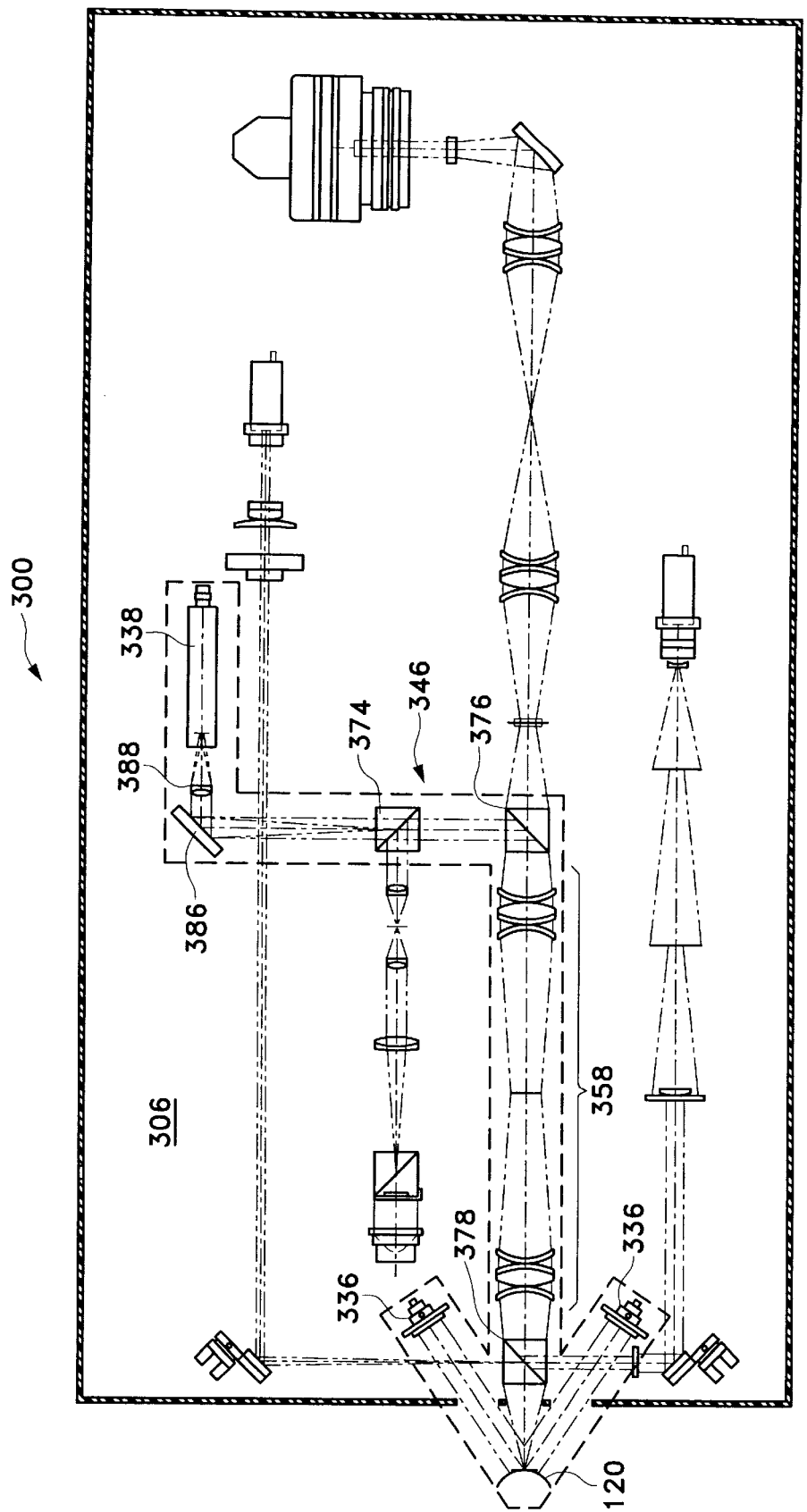
FIG. 12B illustrates a video image optical path of FIG. 12.

With continued reference to FIGS. 12, and 12A, the first optical path 340 is herein described as a fixation path which provides a reference image to the patient, such that the eye 120 is properly aligned when the patient is fixating on the reticle 344 of a reference target 366. A target illumination lamp 368 back-lights the fixation target 366, which fixation target image reaches the patient eye 120 by transmission through a 50/50 beam splitter 370, lenses 372, reflection in 50/50 beam splitters 374, 376, and transmission through lens combinations of afocal relay stage 358, as well as through polarizing beam splitter 378. In addition, a spectral filter is placed over the target illumination lamp 368 to remove radiation over the 620–790 nm wavelength range that might otherwise interfere with a wavefront measurement at 670 nm. The lens combinations in the first relay stage 358 contain identical lens elements mounted in reverse order. Each consists of two meniscus lens elements, with an interposed achromatic doublet. The lens combinations work in tandem as a unity magnification afocal relay stage.

The optical elements including the polarizing beam splitter 378, the lenses of the first afocal stage 358, the beam splitters 374, 376, and one lens 380 of the lenses 372 are mechanically fixed in place on the surface of the platform 306. The optical elements including a lens pair 382 of the lenses 372, the beam splitter 370, the fixation target 366, and the illumination lamp 368 are all mounted on one precision linear translation stage, capable of movement along the optical axis 342 of this pathway. Translation of these optical elements focuses the fixation target 366 for the patient's view, compensating for any myopia/hyperopia present in the eye 120. During patient examination the focus translation stage is adjusted to place the target optically just beyond the eye's infinity focal plane. This allows the patient to see a relatively distinct reticle pattern without stimulating accommodation by the eye 120. The beam splitters 378, 376, 374 serve as interfaces between other optical pathways within the optical axis 342, as will herein be described in further detail. By way of example, the beam splitter 370 is included for alignment purposes. A photo-detector 384 attached to the center of the left edge of beam splitter 370 senses light transmitted toward the fixation target along the optical axis.

With reference again to FIGS. 12 and 12B, the second optical path 346 captures video images of the eye 120 at an examination plane. This allows the clinical operator/technician to assist in patient alignment, and to measure actual eye displacement during the wavefront measurement. As earlier described, the illumination lamps 336 illuminate the eye 120. The image of the eye is conveyed to the video camera 338 by transmission through the polarizing beam splitter 378 and the lens combinations 358, reflection in the 50/50 beam splitter 376, transmission through the 50/50 beam splitter 374, reflection off mirror 386, and transmission through lens 388. All these optical elements are fixed in place on the surface of the platform 306. By way of example, this second path 346 provides a video field of view approximately 22 mm in diameter at the eye plane, with a limiting resolution of ~64 mm. As earlier described, a number of filters are placed in front of each eye illumination lamp 336 to reduce the spectral bandwidth of the radiation reaching the eye 120. By way of example, these will includes a blue filter to remove light at wavelengths below ~455 nm (for eye safety), an infrared filter to remove light at wavelengths above ~920 nm (for eye safety), and a rejection filter to remove light over the wavelength range 620 nm–790 nm (to prevent interference with the wavefront measurement at 670 nm).

Figure 12C:
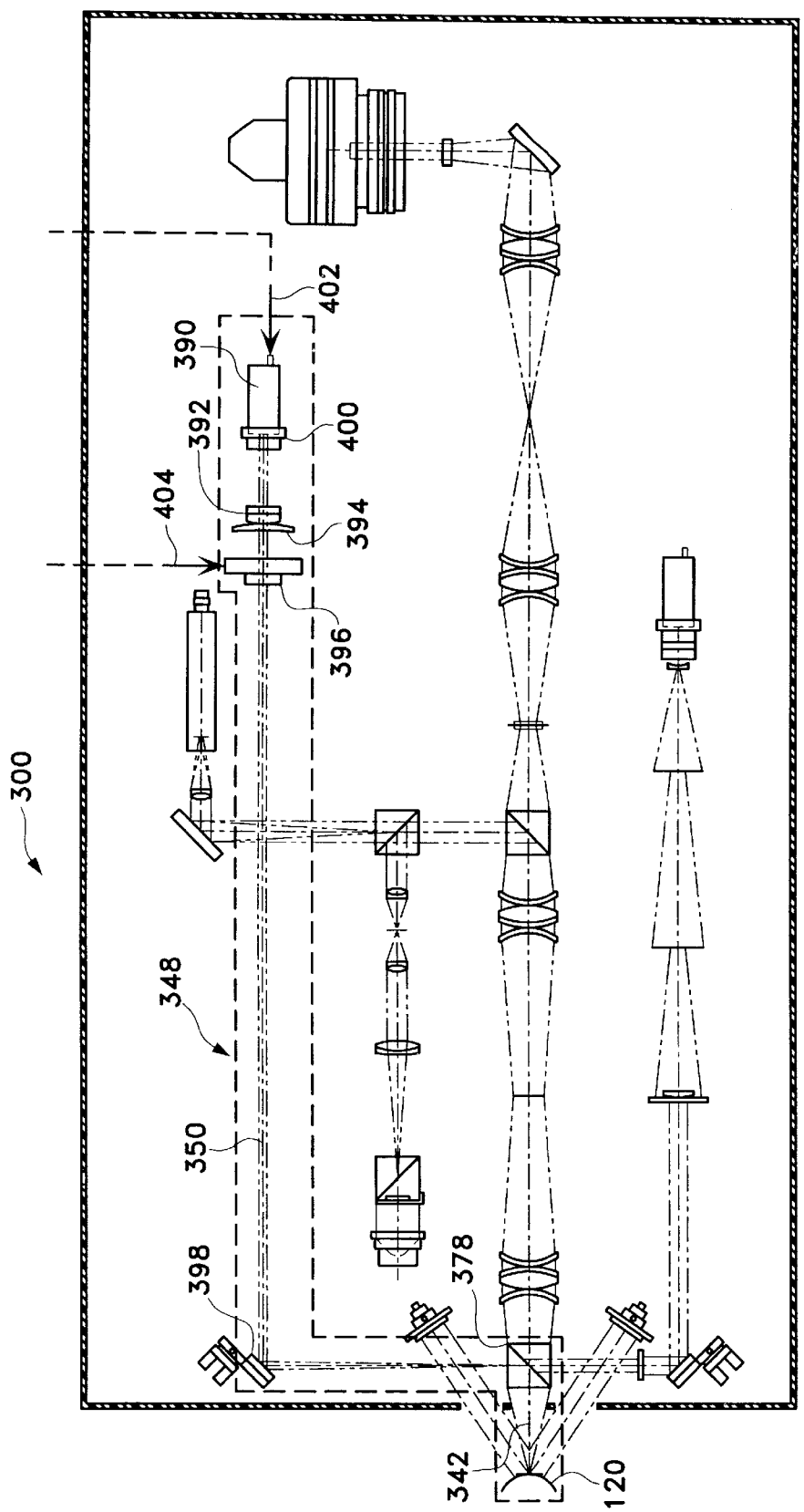
FIG. 12C illustrates a probe laser optical path of FIG. 12.
Figure 12D:
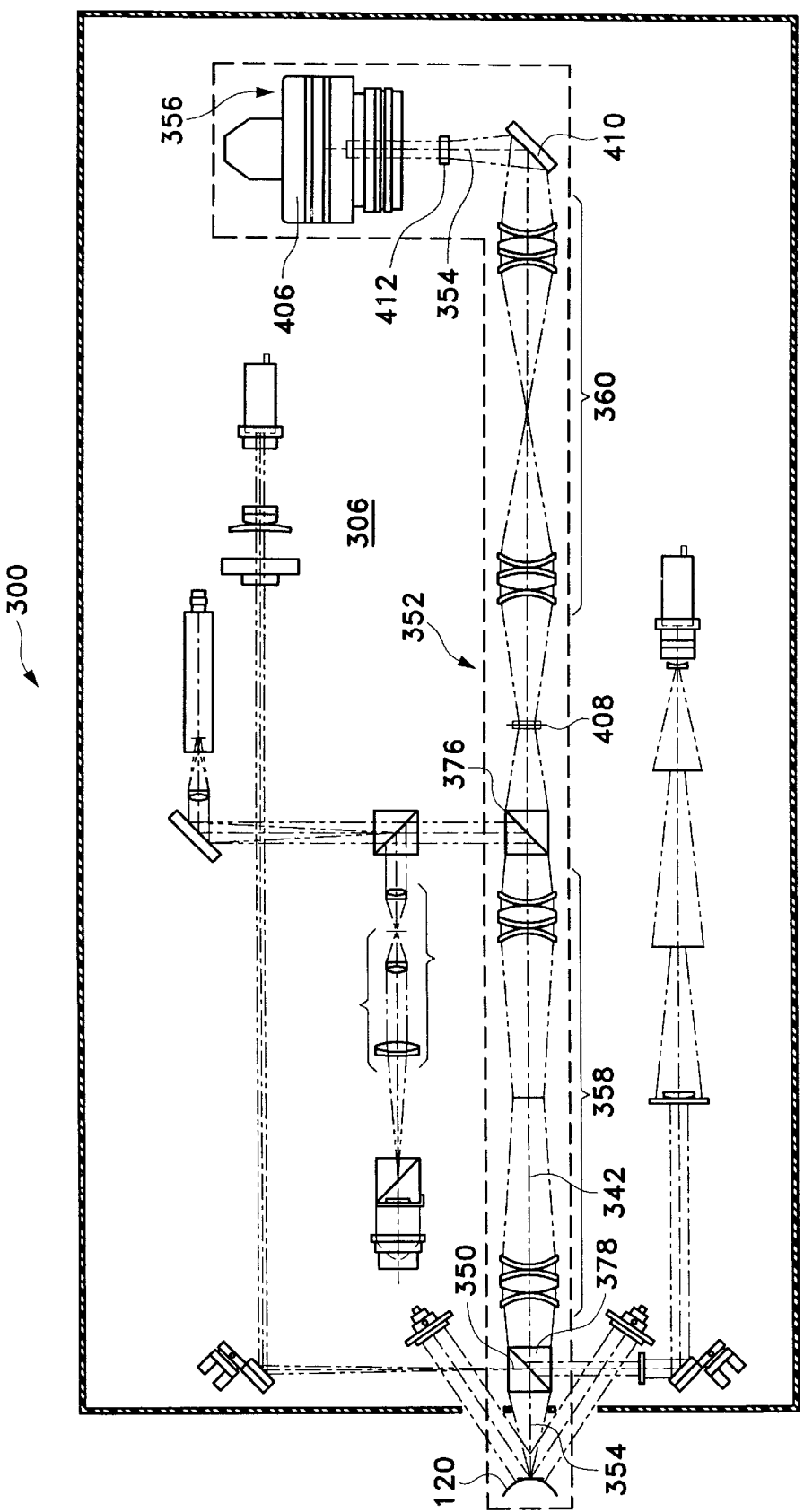
FIG. 12D illustrates a re-emitted wavefront optical path of FIG. 12.
Figure 12E:
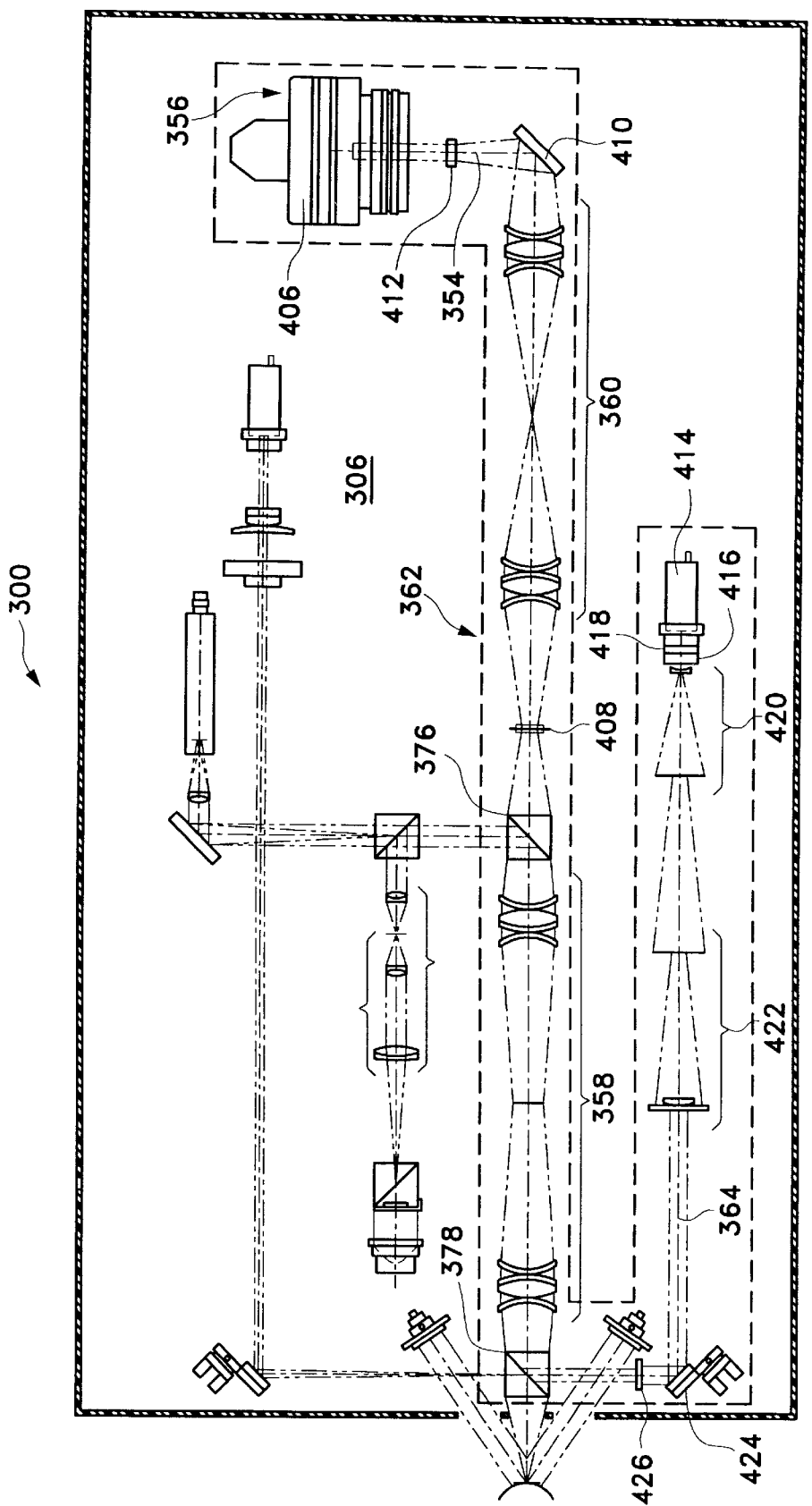
FIG. 12E illustrates a calibration wavefront optical path of FIG. 12.

With continued reference to FIGS. 12 and 12C, the third optical path 348 irradiates a small spot on the patient's retina with eye safe laser radiation, as earlier described with reference to FIGS. 1A–1D. The irradiated retinal spot on the fovea centralis 123 of the retina 122 is, as herein described, the origin of the re-emitted wavefront 130 measured by the sensor 356. The output beam, probe laser beam 350 from diode laser 390 reaches the patient eye 120 by transmission through a linear polarizer and attenuator 392, lens 394, shutter 396, and reflection off mirror 398 and in the polarizing beam splitter 378. All these elements are fixed in position.

In one embodiment of the present invention, output of the diode laser 390 is essentially collimated and is focused onto a corneal surface of the eye 120 by lens 394. The projected probe laser beam 350, collimated light from the diode laser 390, is directed by a long focal length lens 394 for focusing on the anterior surface of the cornea 126 of the eye 120, as illustrated by way of example with reference again to FIG. 1B, passing through the pupil and lens 124 of the eye 120, and onto the retina 122 as a small measurable spot on the fovea centralis 123. As earlier described with reference to FIG. 7, in one embodiment, the lens 394 illustrated with reference again to FIG. 12, comprises a zoom lens for varying the focus and moving the focus location as desired. By focusing on the cornea 126, the measurement is minimally dependent on the curvature of the cornea. However, other locations proximate the corneal surface are acceptable.

While diffraction and various aberrations are present, the present invention 5 avoids the aberration effects from the cornea which typically dominate. The lens of the eye 120 contributes a relatively small aberration effect when compared to that of the cornea 126. Further, and with regard to the selection of the lens 394, selecting a lens with a short focal length would provide a relatively large incident angle of the beam 350, a well focused point on the surface of the cornea 126, and less aberration effects from the cornea. A small incident angle provides a larger focus point on the cornea 126, but a more desirable smaller spot on the retina 122, which spot size will depend on the wavelength and starting point size and focal length of the lens 394 selected. Embodiments of the present invention including lenses of approximate one half meter and 100 mm, by way of example, haves been effectively used.

The polarizer 392 linearly polarizes the probe beam 350 into an s-state (by way of example, out of the plane of the drawing of FIG. 12). The angled interior interface of the polarizing beam splitter 378 reflects s-polarized light, so that light entering the eye 120 is s-polarized. A linear polarizer 400 is angled with respect to the polarizer 392 and works in conjunction with the attenuator to attenuate probe beam power delivered to the eye 120 to less than 10 $\mu$W, by way of example. The diode laser 390 is triggered by an external electrical trigger signal 402. A nominal illumination duration for eye measurement is 700 ms. The shutter 396 is included as an additional safeguard against overexposure of the eye 120 to the probe laser beam 350. The shutter 396 is normally closed and is opened by an independent electrical trigger signal 404 synchronized to the laser trigger signal 402.

By way of example, one retinal exposure for each illumination by the probe beam is 10 μW×0.7 s=7 μJ. Up to 10 repeat measurements may be obtained during a single patient examination session. Such exposures are well within the safety limits defined in the American National Standard for Safe Use of Lasers (ANSI Z136.1-1993, American National Standards Institute, New York, N.Y.). In that reference, the maximum permissible exposure (MPE) for "intrabeam" viewing a laser beam in the 400–700 nm wavelength range and the $18 \times 10^{-6}$ to 10 second pulse duration range is $1.8 * t^{3/4}$ mJ/cm$^2$. (t is the pulse duration in seconds). A limiting aperture for the eye is identified as approximately 7 mm in diameter. As a result, an allowable single-pulse energy is $0.6927 * t^{3/4}$ mJ. For a single 0.7 second pulse the MPE is 530 μJ, almost two orders of magnitude larger than a delivered energy per pulse, for the apparatus herein described. An additional calculation is performed to assess the safety of the repetitive exposures. The relevant calculation in the Standard multiplies the single pulse MPE by $n^{-1/4}$, where n is the total number of pulses in the exposure duration $T_{max}$. For the apparatus of the present invention, the 10-pulse safety limit is 530 μJ/pulse×$10^{-0.25}$= 298 μJ/pulse, still a factor of 40 larger than the actual pulse energy focused into the eye.

Figure 12F:
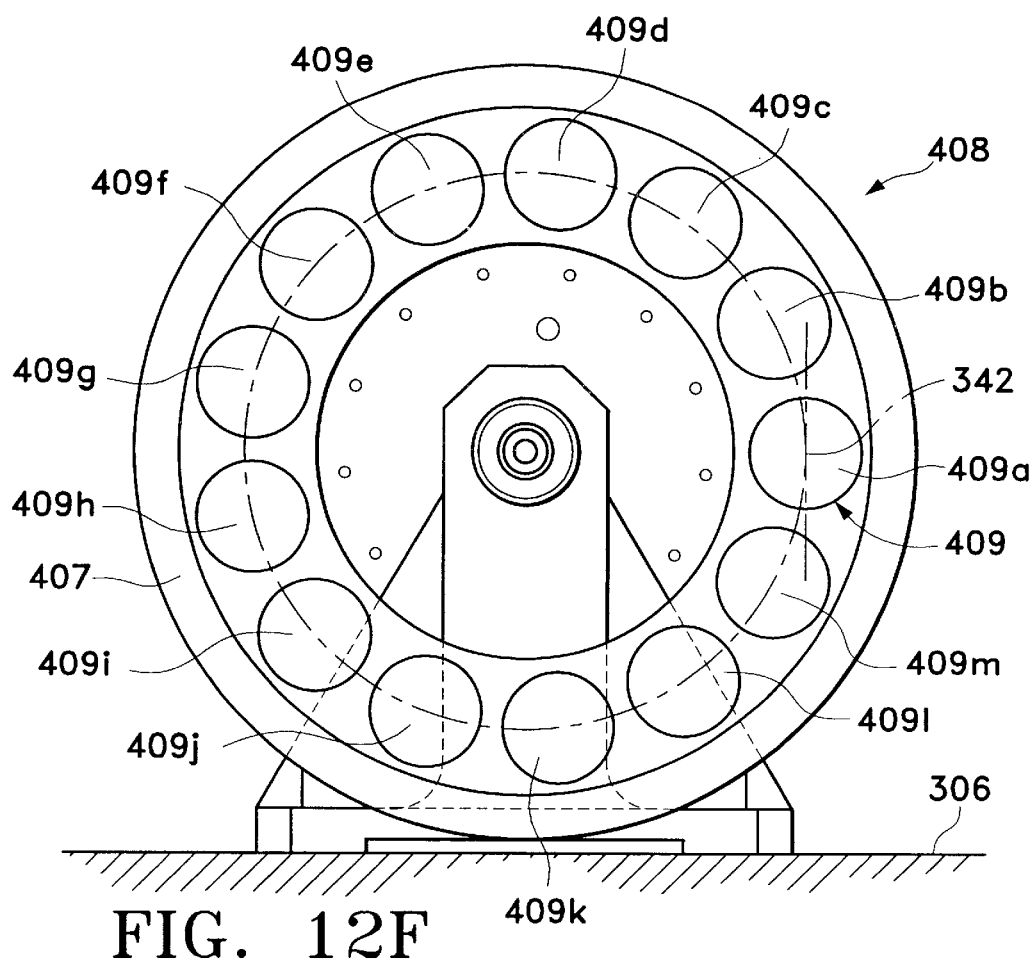
FIGS. 12F and 12G are front elevation and top plan views of a trial lens holder useful with embodiments of the present invention herein described.
Figure 12G:
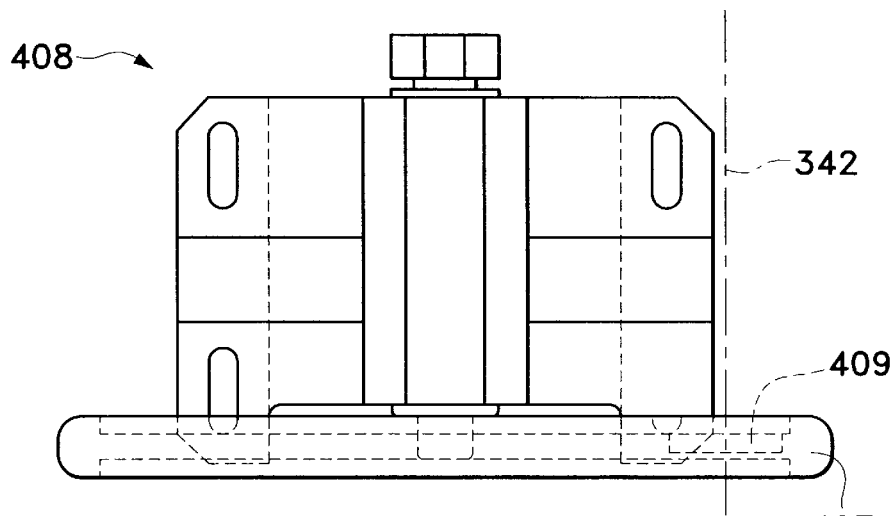

As illustrated with reference again to FIGS. 12 and 12D, the fourth optical path 352 conveys the wavefront 354, earlier identified by numeral 130 with reference to FIG. 1B, emerging from the eye 120 to the wavefront sensor 356, herein described using a Hartman-Shack sensor by way of example for the wavefront analysis. The wavefront 354 re-emitted by the eye 120 in response to the probe beam 350 irradiation is conveyed to a CCD camera 406 by transmission through the polarizing beam splitter 378, the first afocal relay stage 358 lens combination, the 50/50 beam splitter 376, a trial lens holder 408, the second afocal relay stage 360 lens combination, reflection off mirror 410, and transmission through microlens array 412, as earlier described with numeral 33 with reference to FIG. 6. With the exception of the changeable trial lens holder 408, illustrated with reference to FIGS. 12F and 12G, all these optical elements are fixed in place on the surface of the platform 306.

The polarizing beam splitter 378 transmits only linearly polarized light in a p-state. The radiation of the probe beam 350 reflected from the corneal surface of the eye 120 will retain the incident s-state polarization and will not be appreciably transmitted by the beam splitter 378. In contrast, light that has been scattered off the retina of eye 120, light forming the wavefront 354 of interest, will be largely depolarized. The p-polarized fraction of this light will be transmitted by the beam splitter 378. Thus the beam splitter 378 selectively suppresses the corneal surface reflection that could otherwise complicate the wavefront measurement. A wavefront originating at the corneal plane of eye 120 is transferred to a plane of the trial lens holder 408 with unity magnification. This plane of the trial lens holder 408 provides an intermediate pupil plane and is included for placing an ideal N-diopter lens 409, see FIGS. 12F and 12G, at the trial lens plane to change the spherical curvature of the wavefront 354 by N-diopters, without altering other aberration content. The capability to reduce/remove the general wavefront curvature in a preselected manner significantly extends the dynamic range in wavefront measurement, without degrading the measurement accuracy. Trial lenses 409a–409m, by way of example and herein described of varying spherical powers, ranging from −16 diopters to +8 diopters in two-diopter increments, are mounted on a rotating wheel 407 of the holder 408. The wheel's axis of rotation is parallel to but offset from the optical axis 342. Turning the wheel places one of a plurality of preselected trial lenses at the trial lens plane. The wheel has precision mechanical detents that register the selected lens properly in the optical path.

A narrow band-pass optical filter is also placed at trial lens holder 408 location just anterior to the lens position. This filter has maximum transmission for 670 nm wavelength radiation (the probe beam wavelength), and a bandwidth of approximately 10 nm (full-width-half-maximum). This filter is used to reject spurious light (from the fixation target illumination, the eye illumination, and the like) from the wavefront path.

In one embodiment, as herein described by way of example, each of the lenses of the second afocal relay stage 360 consists of three lens elements, two meniscus lenses and an interposed achromatic doublet. However, they are not identical, and their combined action serves to magnify the passing wavefront 130. The wavefront 354 at the trial lens holder 408 location is imaged onto the surface of the microlens array 412 with a magnification of 1.22. Magnification of the wavefront image by this defined factor of 1.22 reduces the wavefront slope at each point in the image plane by the same 1.22 factor. This extends the measurement dynamic range of the device, again without decreasing accuracy. In addition, this magnification distributes the wavefront 130 over more elements, CCD cells 38 as earlier described with reference to FIG. 6, in the microlens array 412, thus increasing the number of slope measurements provided by the wavefront sensor 356. The mirror 410 is included to fit elements of the apparatus 300 within the dimensions of the platform 306. In addition, the mirror 410 also allows optical alignment adjustment for the microlens array 412 and the CCD camera 406 combination. As earlier described, by way of example, with reference to FIGS. 3–6, the microlens array contains a square array of microlenses which divide the incident wavefront into a transverse array of secondary "wavelets." These wavelets are focused onto a detector surface of the CCD camera, which is positioned parallel to the microlens array and one focal length posterior thereto. The pattern of focused wavelets in the CCD image is used to calculate the shape of the incident wavefront.

As illustrated with reference again to FIGS. 12 and 12E, the calibration beam path 362 provides the collimated beam 364 to the Hartman Shack wavefront sensor 356. Wavefront data for the collimated beam 364 is used as a reference in reconstructing the aberrated wavefront 354 from the real eye measurement. The source for the collimated reference beam 364 consists of a diode laser 414 coupled to beam expander 416. In one embodiment of the invention herein described, the diode laser 414 used for reference is identical to the diode laser 390 used for the probe beam path 348. The collimated reference beam 364 is conveyed to the CCD camera 406 by transmission through polarizer/attenuator 418, negative lens and aperture 420, aperture and positive lens 422, reflection off mirror 424, transmission through aperture 426, reflection in the polarizing beam splitter 378, transmission through the first afocal relay stage 358, the 50/50 beam splitter 376, the trial lens holder 408, the second afocal relay stage 360, reflection off the mirror 410, and finally transmission through the microlens array 412. Except for trial lens holder 408, all these optical elements may be fixed in position on the surface of the platform 306.

The optical element of the polarizer and attenuator 418 contains two linear polarizers and a neutral density filter.

The linear polarizer furthest from the diode laser 414 polarizes the laser radiation in the s-state for maximum reflection in the polarizing beam splitter 378. The linear polarizer closest to the diode laser 414 is partially "crossed" with respect to the polarizer 378 to attenuate the laser power. The neutral density filter further attenuates the beam, such that the laser power reaching the CCD Camera 406 is optimal for calibration of the sensor 356. The negative lens and positive lens of elements 418, 420 expand the diode laser output and form the collimated reference beam 36. Intervening apertures of elements 418, 420 transmit only the central portion of the expanding beam with the most uniform intensity. The mirror 424 is included to reduce the overall dimensions of the apparatus 300. The aperture 426 is conjugate to the corneal plane, and is included so that the collimated reference beam 364 illuminates approximately the same area on the microlens array 412 as would the wavefront 354 re-emitted by a maximally dilated eye.

Figure 13:
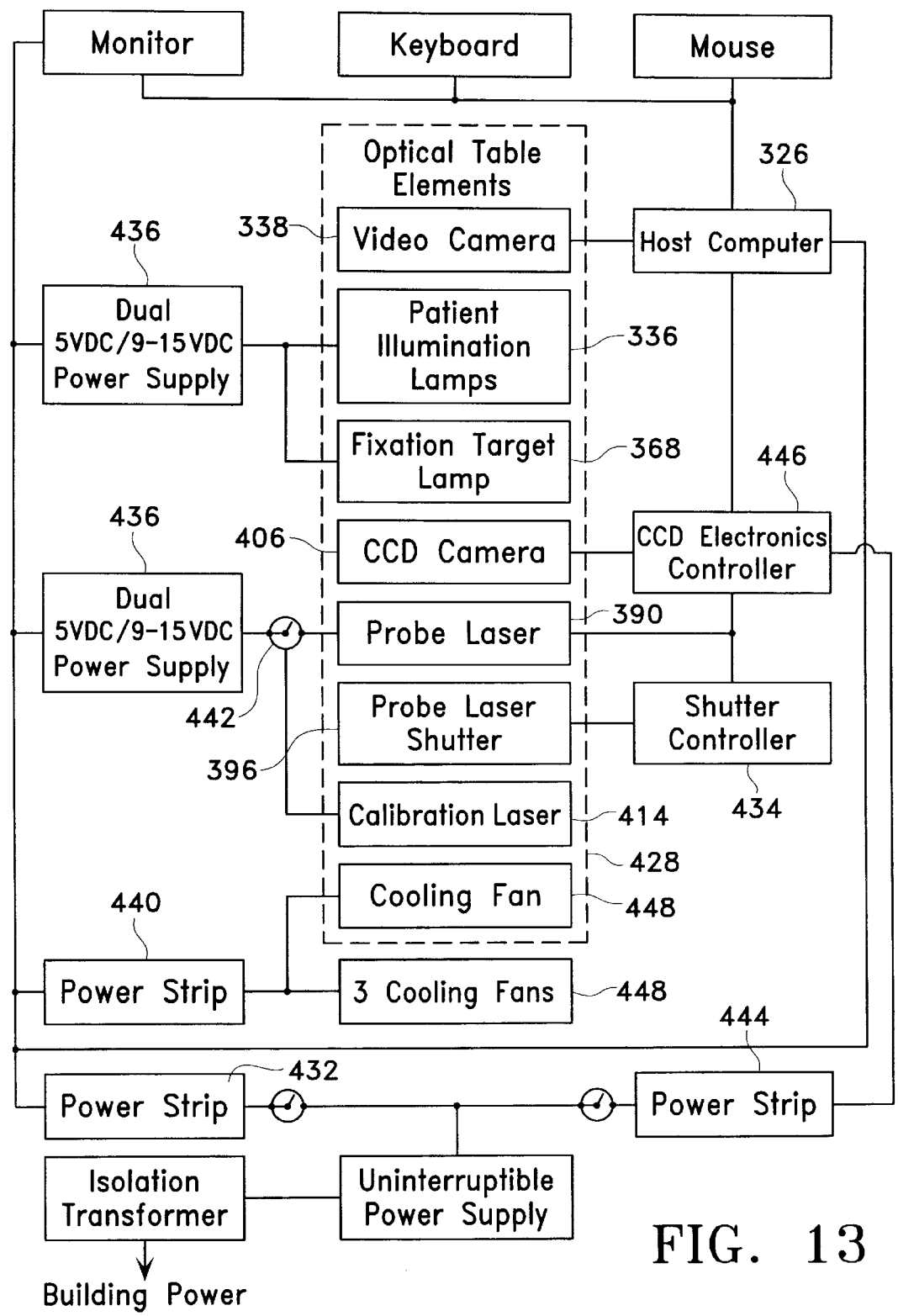
FIG. 13 is a block diagram illustrating electrical components of the embodiment of FIG. 9.

By way of illustration, optical components suitable for use with embodiments of the present invention herein described by way of example, are provided with reference to Table 1. An electrical component layout of the apparatus 300 is illustrated with reference to FIG. 13, wherein a dashed box 428 indicates the platform 306 with the heretofore described element carried thereon. Except for the computer monitor, keyboard, and mouse all other electrical components are located within the frame under the optical table. Switches in the diagram are all located on a front panel 430 of the electronics 324 for ease in operator/technician access, as described earlier with reference to FIG. 9. Electrical power from the clinical facility is drawn by an isolation transformer, which in turn supplies power to an uninterruptible power supply (UPS). The UPS delivers power to three power strips carried in the frame 308. The host computer 326 has a self contained On/Off switch, as do the three power strips. One power strip 432 supplies power to the shutter controller 434, which commands the probe laser shutter 396 through the signal 404, two dual power supplies 436, each capable of providing both 5 VDC and 9–15 VDC output, the host computer 326, a computer monitor 438, and a third power strip 440. One dual power supply supplies 5 VDC power to the two patient illumination lamps 336, and 9 VDC power to the target illumination lamp 368. A second dual power supply supplies 5 VDC power to both diode lasers 390, 414. A user-accessible 3-position switch 442 allows the system operator/technician to provide power to either the probe laser 390 or the calibration laser 414, with a center switch position being the "off" state.

A third power strip 444 supplies power to the CCD electronics controller 446. The power strip 440 also supplies power to cooling fans 448 located on the platform and within the frame.

By way of example and for illustration purposes, operation of the apparatus 300 may generally proceed with the operator/technician first activating each of the electrical elements, with the CCD electronics controller 434 being last to be enabled. The operator then activates the calibration laser 414 via the 3-position switch 442. The operator then instructs the computer 326 to acquire a calibration wavefront measurement. The computer 326 relays this command to the CCD controller electronics 446, which activates the CCD camera 406 to take a predefined exposure. The CCD controller electronics 446 also sends trigger signals 402, 404 described earlier with reference to FIG. 12, to the probe laser 390 and the probe laser shutter 396. However, since the probe laser 390 is not powered at this point, no probe beam 350 is delivered. Calibration CCD data are transferred to the CPU of the computer 326, and stored for later analysis. The calibration laser 414 is switched off at the end of the calibration procedure.

The technician/operator then proceeds to patient measurements. The output switch 442 at the dual voltage power supply 436 is positioned to a probe laser setting. The probe laser 390 is now in a "ready" state awaiting an additional trigger signal to operate. The operator then positions the patient appropriately in the apparatus 300 as earlier described with reference to FIGS. 9–11, with the assistance of an image from the video camera 338 displayed on the computer monitor, by way of example. With the patient situated, the operator instructs the computer 326 to obtain wavefront data, as earlier described with reference to FIGS. 2–7. The computer 326 relays appropriate commands to the CCD electronics controller 446, which triggers the probe laser 396 to fire, triggers the shutter controller 434 to open the probe laser shutter 396, and exposes the CCD camera 406. CCD camera image data is transferred back to the computer 326. The computer 326 includes software that analyzes the patient and calibration data to calculate the patient wavefront profile for use. At the end of the data collection, the operator shuts down the electronics, starting with the CCD electronics controller 446. The software integrated into the apparatus 300 may be described, by way of example, as including: A graphical user interface (GUI) to allow the technician to perform all desired operations to enter and save patient information and perform the desired measurements; database and file system interfaces to allow for the saving and tracking of patient information, measurement, and hardware details; control of the electro-optical and electro-mechanical components as necessary in order to be able to accurately and safely perform the desired measurements; and processing of the measurement data to generate mathematical descriptions of the aberrations (the optical path difference) measured in the subject eye.

By way of further example, patient measurement and apparatus configuration information is stored in multiple tables in a Microsoft Access™ 7.0 database. The interface to this within the code is based upon the Microsoft Foundation Classes (MFC) wrapper to the Microsoft Jet Engine. The framework generates a Structured Query Language (SQL) to create, retrieve and update records in the database. Use of the Microsoft Access application to access the data is not needed. In one embodiment of the present invention, the following data may be stored in the database: patient information—name, address, medical record number, and the like; measurement Information—geometry, time of measurement, and the like; and system Information—hardware serial numbers and key hardware parameters.

Additionally, the software may be developed with two operating levels—password-protected and not-password-protected. From within the password-protected-mode, the technician/operator has access to system configuration information and features necessary for system setup and maintenance that are not accessible from the not-password-protected mode. All patient entry and measurement capabilities are available from the not-password-protected mode. All patient information desired in order to be able to uniquely identify and track the patient is entered via the graphical user interface (GUI) and stored in the Microsoft Access database. Selecting the "Patient Data" menu item brings up a patient information data information screen, from which the technician can enter new patient data as well as being able to review and edit existing information. The patient data that can be stored and retrieved, typically includes: name, address, medical record number, data of birth, phone number, sex, manifest and cycloplegic refractions and vertex distance as well as centration information.

Figure 14:
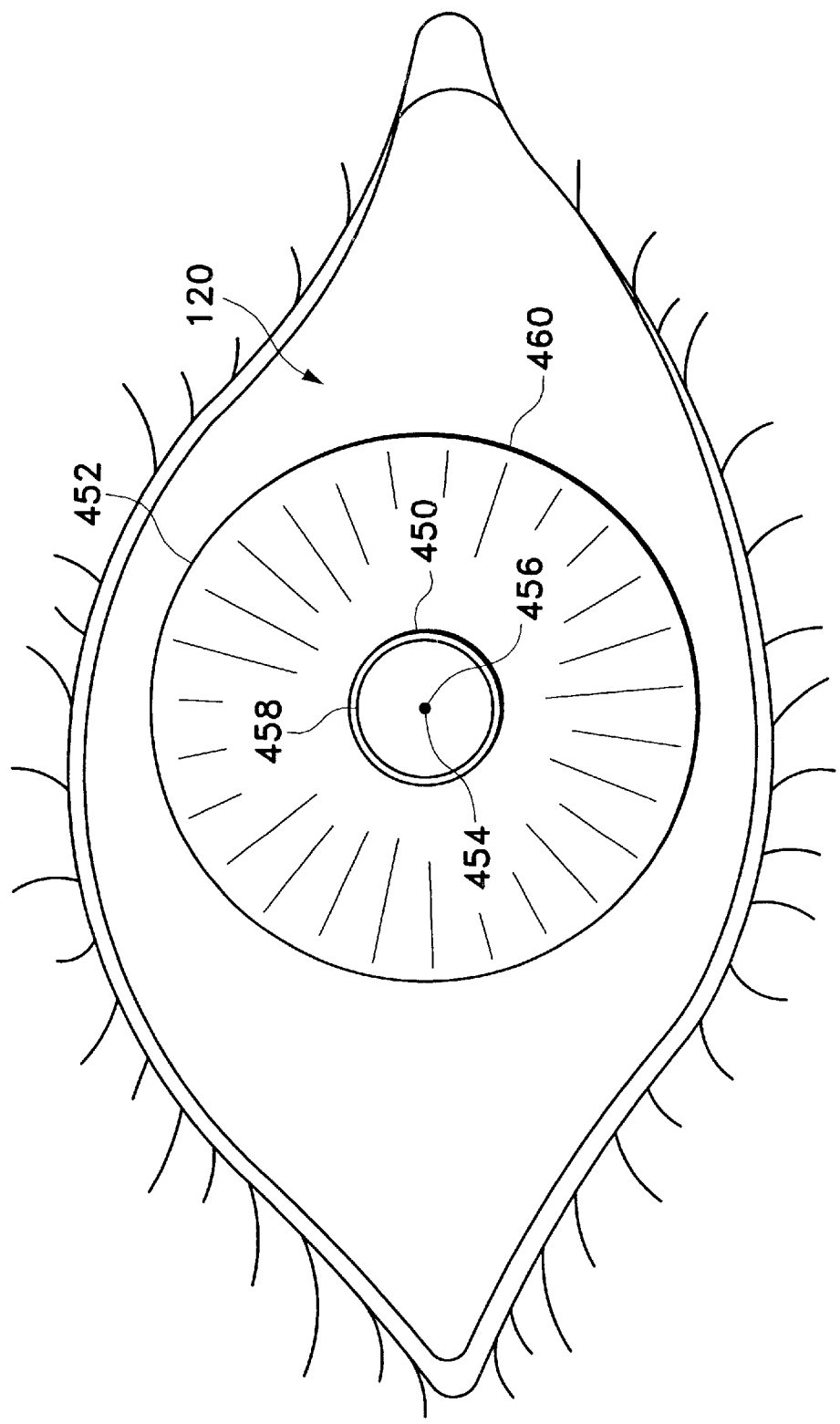
FIG. 14 is an enlarged image of an eye illustrating a centration image.

Centration information that is measured via a centration process and stored as part of the patient record describes the position of the center of the constricted pupil with respect to the center of the limbus. This information is used in aligning the patient for the measurement where the goal is to align the visual axis of the eye with the optical axis 342 of the apparatus 300. When the centration procedure is invoked a list is displayed of all patients that have been entered into a database operable with the apparatus 300 but have not yet had the centration steps performed. The monitor displays all patient information including a review of centration information, or alternatively, for just those patients entered for a given time period. In order to perform centration for a given patient and eye, that patient is selected from this list by clicking on the desired patient/eye with the mouse. An example of the centration process is illustrated with reference to FIG. 14. Once a patient has been selected, the patient is instructed to look into the apparatus 300 and at the fixation target 366, as earlier described with reference to FIG. 12.

By way of further disclosure, the fixation target 366 is, as earlier described, included so that the patient 302 can stare along the optical axis 342 of the apparatus 300. For best fixation, the target should be clearly visible to the patient. However, care should be taken to see that the patient does not attempt to accommodate when fixating on the target. This would occur if the target were optically closer than the patient's infinity focal plane. If the patient did accommodate, i.e., if the lens in the eye changed shape to provide increased focusing, then the eye would appear excessively myopic during the wavefront measurement. To avoid this, the fixation target optics are adjusted so that the target appears to lie optically just beyond the patient's far-field focus. Thus for each patient the target will appear relatively clear, but not in sharp focus. The patient may initially try to accommodate to improve the sharpness of the image, but will eventually find that the clearest image is seen for the most relaxed (non-accommodative) state. This technique is known as "fogging," and is routinely performed by optometrists when doing clinical evaluations. The eye drops used to dilate the eye for the measurement also reduce the lens' ability to accommodate, thereby further ensuring valid wavefront measurement.

With reference again to FIG. 14, an image of the patients eye 120 is frozen. Two reticles 450, 452 are then used to locate the centers 454, 456 of the constricted pupil and limbus, respectively. Each reticle 450, 452 can be moved and sized—one reticle 450 is positioned over the perimeter of the constricted pupil 458 and the other reticle 452 over the limbus 460. Once they have been located, the information is saved to the database. This can be performed for as many patients as is desired and the centration procedure is then exited.

Figure 15:
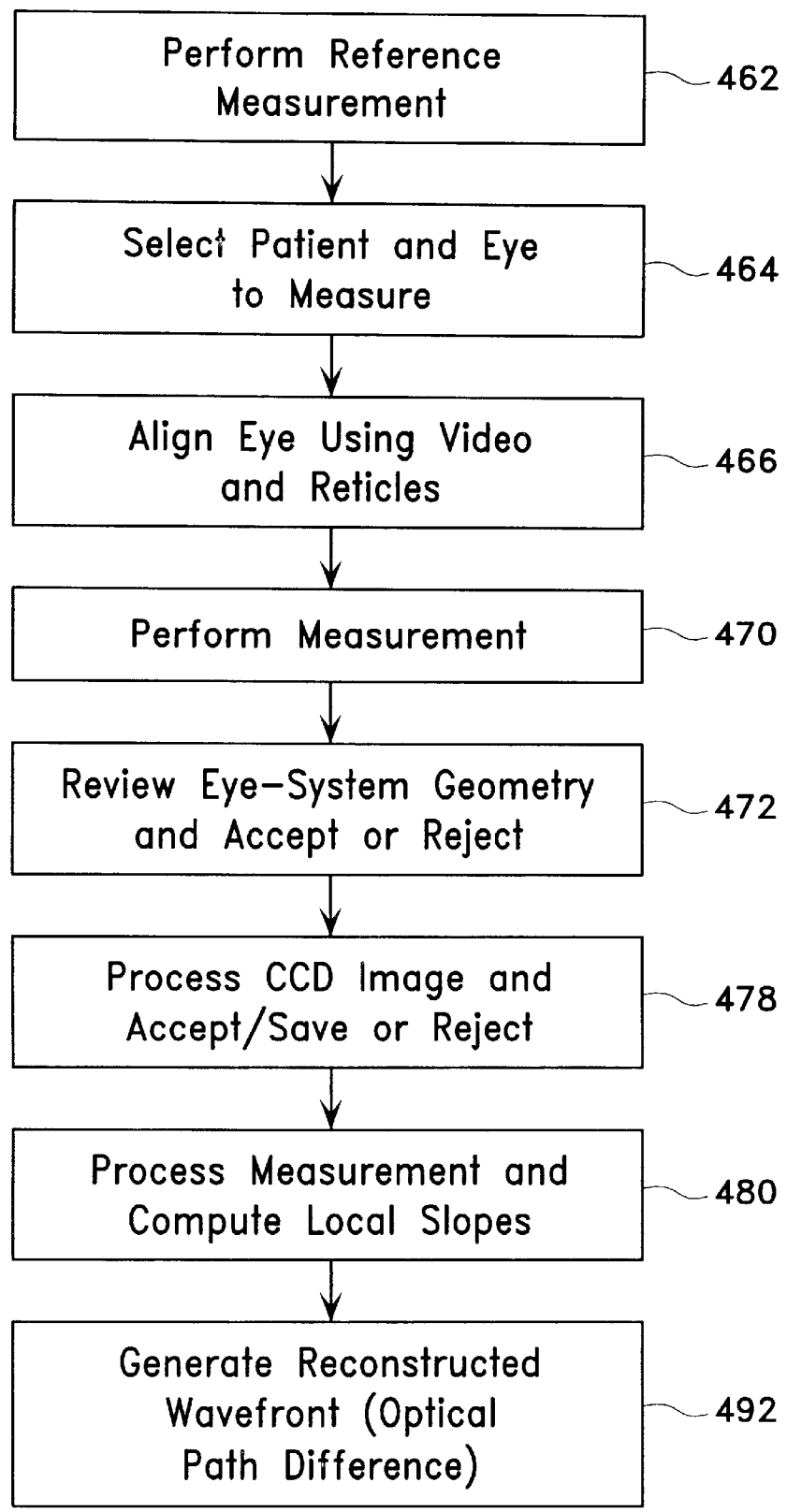
FIG. 15 is a block diagram illustrating an operable flow of steps used in one embodiment of the present invention.

For illustration, a sequence of events followed in measuring the refractive errors in an eye and computing the corresponding optical path difference (OPD) is illustrated with reference to FIG. 15. By way of example, steps include performing a reference measurement 462. To provide a reference with which to compare the measurement of the eye 120 and also to check the alignment of the apparatus 300, a reference measurement is made using the collimated laser light 36, as earlier described with reference to FIG. 12. The software forces the operator to make at least one such measurement at the start of each day and an additional one at the end of each day. More reference measurements can be performed as desired by the operator. When patient measurements are performed, the measurement records in the database identify which reference measurements correspond to each measurement, i.e., which reference image was the latest one done prior to the measurement. A "Perform Reference Measurement" screen may be provided for viewing a sample reference image.

A next step includes selecting a patient and eye to measure 464. The patient and eye to be measured may be selected from a "Patient Select" dialog screen. It is desired that all patients are displayed along with a check mark to show whether or not centration has been performed for that patient. If a patient is selected that has not yet had centration performed then the operator is informed of this and no measurement can be performed. Once a valid patient/eye has been selected to be measured then the perform measurement dialog is displayed which includes GUI buttons necessary in order for the operator to perform and check the measurement.

A next step includes aligning the eye using the video camera and reticles 466. The apparatus 300 is operated with the visual axis of the eye aligned, as close as is practically possible, to the optical axis 342 before performing a measurement. The center of the constricted pupil 454 is used as the approximate anatomical landmark for the visual axis. Given that the eye 120 is dilated when the measurement is performed, it is not possible to directly determine this center. However, the centration procedure performed on each patient defines the center of the constricted pupil 454 with respect to the limbus 460 and thus it is possible to use the position of the limbus to place the eye 120 in a desired location.

Figure 16:
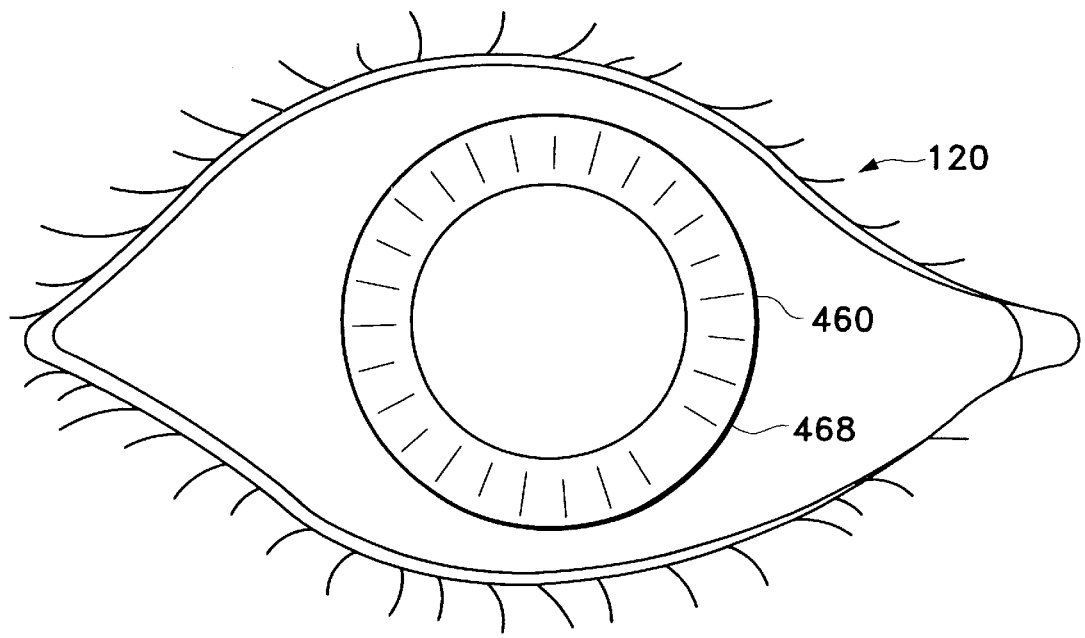
FIG. 16 is an enlarged image of an eye illustrating a pre-measurement eye alignment.

As illustrated with reference to FIG. 16, a reticle 468 is displayed on screen that is offset from the optical axis by the appropriate amount such that when the limbus 460 of the eye 120 is aligned to this reticle 468, the eye 120 is positioned as desired. Prior to taking the measurement, it is the operator's responsibility to ensure that the patient is positioned appropriately such that the limbus 460 is aligned with the reticle 468 while the patient is looking at the fixation target 366.

A measurement is then performed 470. Once the eye 120 is aligned, the operator presses an "acquire" button to perform the wavefront measurement of the patients eye. The system response to the acquire command is as follows:

1. Video image is frozen
2. Probe beam laser is activated
3. External shutter is opened so that the probe beam can reach the eye
4. CCD shutter opens and the CCD is exposed to the re-emitted wavefront (1–4 generally performed simultaneously)
5. CCD shutter closes and the exposure is completed
6. CCD data is transmitted to the computer
7. External shutter closes and the probe beam turns off.

The software continually checks the status of the CCD electronics and the temperature of the camera and only allows measurements to be taken when everything is working nominally.

Figure 17:
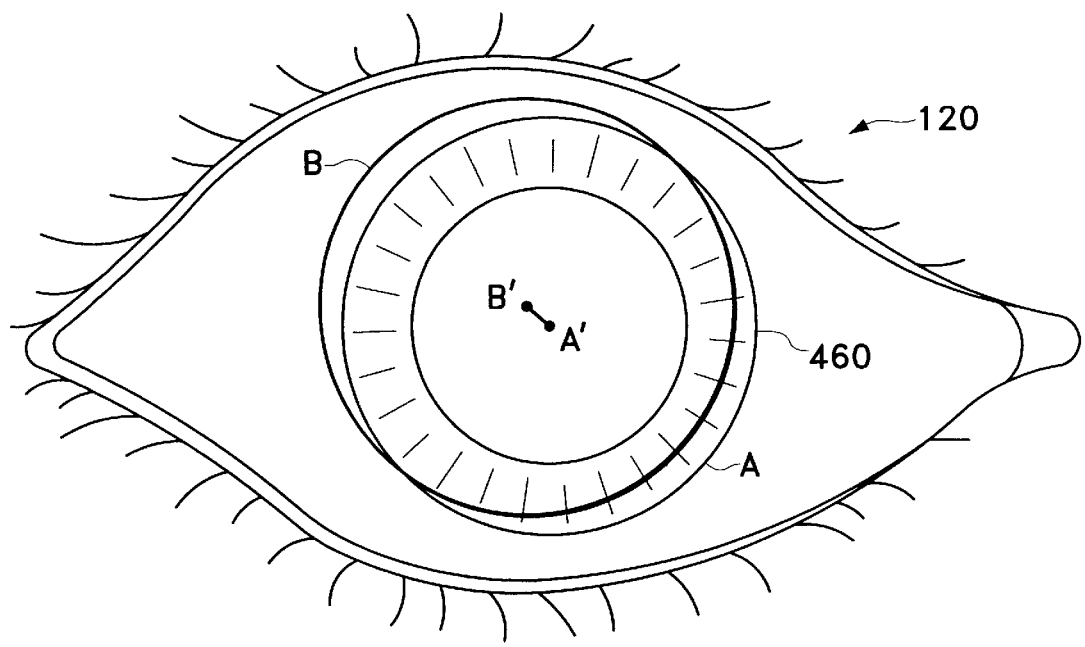
FIG. 17 is an enlarged image of an eye illustrating a pre-measurement eye alignment checking thereof.

A review of eye and apparatus geometry is accepted or rejected 472. Although it is not necessary for the eye 120 to be perfectly aligned with respect to the optical axis 342 (the software compensates for minor misalignments), it is desirable for it to be close. The eye 120 will have been aligned prior to the measurement but uncontrollable eye motion (e.g. saccades and loss-of-fixation) may make the alignment sub-optimal at the time of the exposure. To check that the alignment is acceptable, the video image of the eye is frozen at the time the measurement is taken. The operator then aligns a reticle to the limbus ring and presses a "check geometry" button on the GUI. If the software determines that the alignment is not acceptable, the operator is informed of this and a new exposure is made as desired. By way of example, and with reference to FIG. 17, optimal measurement as herein described, would have the limbus 460 aligned to circle B. In actuality, the eye 120 was offset during the exposure and the limbus 460 was aligned to circle A. The difference between these two states is shown by the line A'B'. The software determines whether or not the image is acceptable based on the length of A'B'.

Figure 18:
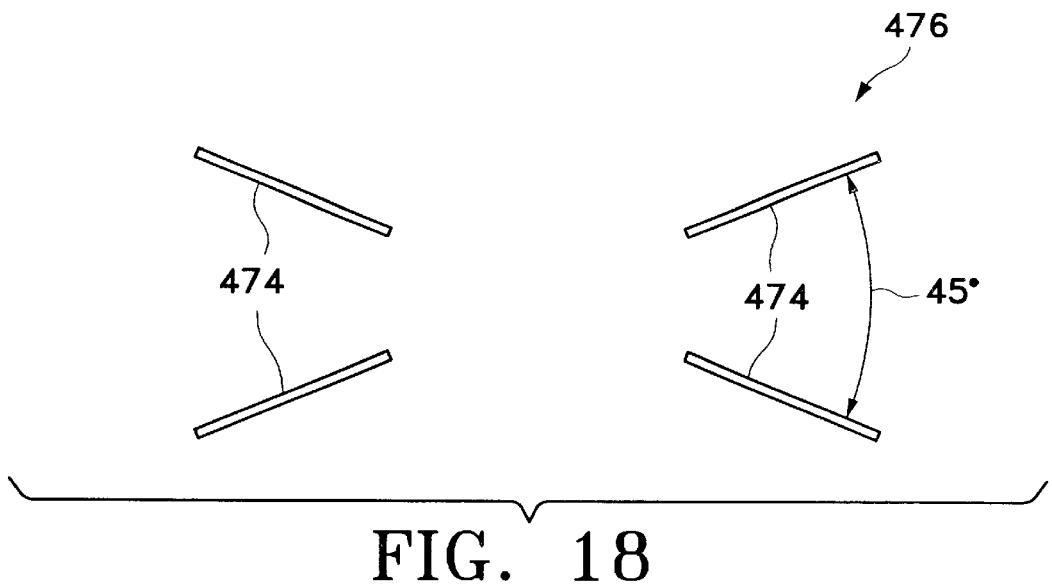
FIG. 18 is a line diagram illustrating an eye registration pattern.

It is also at this point that the operator records the rotational state of the eye. Prior to the wavefront measurement, a pattern of four line segments 474 arranged in an "X" pattern 476, as illustrated with reference to FIG. 18, around the periphery of the cornea are applied to the eye using a mechanical instrument. The pattern 476 consists of two pairs of collinear line segments 474 angled at 45° with respect to each other. Each line segment 474 is 4 mm long, and collinear segments are separated by 7 mm. At the same time the limbus ring reticle is aligned with the actual limbus in the frozen video image, an X reticle that matches this pattern is aligned to the applied eye marks in the frozen image. The orientation information is then saved by the software along with the limbus position data.

Figure 19:
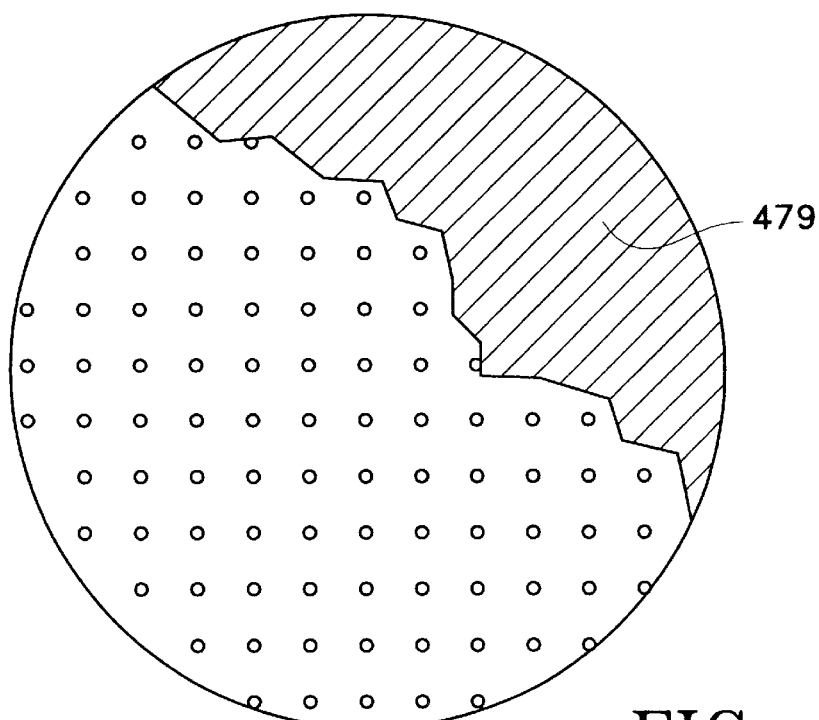
FIG. 19 illustrates a rejected CCD image.

As a next step in the process, the CCD image is processed, accepted and saved, or rejected 478, as illustrated with reference again to FIG. 15. If the geometry of the measurement is acceptable, it is then probable that the quality of the CCD image will be high. It is desirable, however, to check that this is so. The software processes the image and then presents an auto-scaled image to the operator to review. If the software determines that the image is unacceptable then the operator will be informed of this and a new exposure made. If the user decides that the image is unacceptable for whatever reason then the image can be manually rejected at this stage. An example of an unacceptable image is illustrated with reference to FIG. 19. In this example, a significant portion 479 of the image is obscured in some manner, resulting in wavefront data for only part of the pupil. By unacceptable, it is meant that such an image is not believed to result in the accuracy and precision of measurement that is desired for surgical procedures which are obtained by the present invention. It does not mean that such as illustrated may not be usable in any sense.

Figure 20:
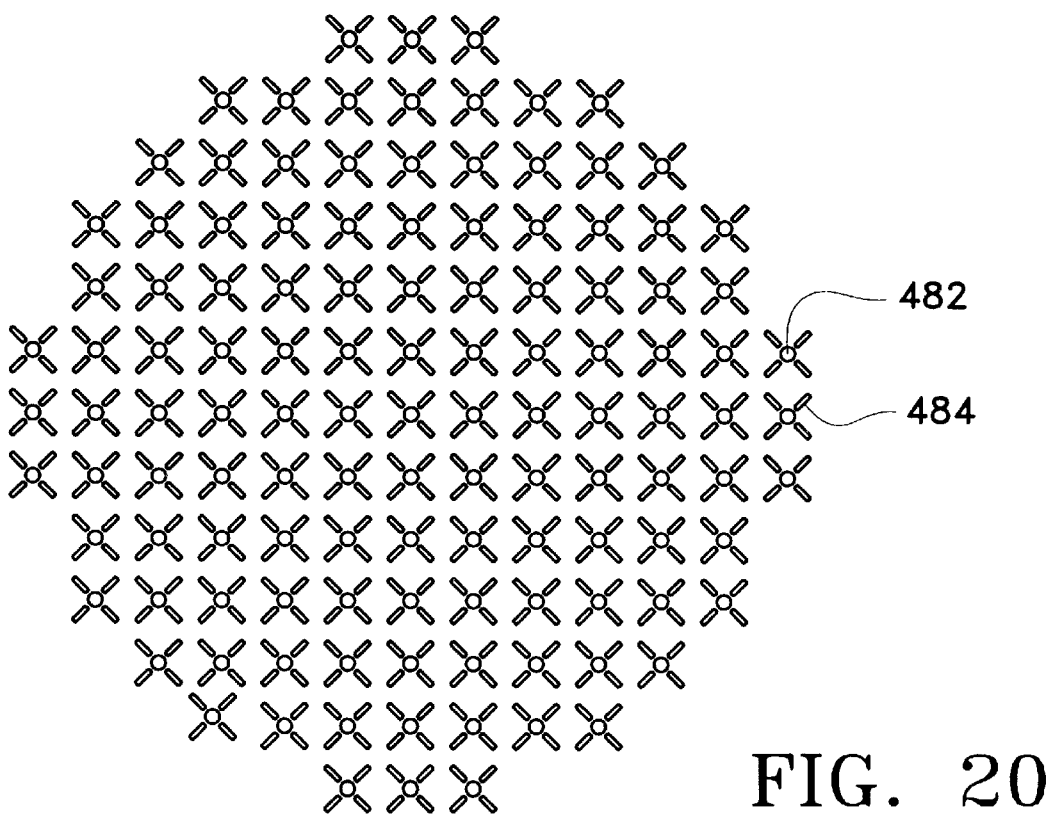
FIG. 20 illustrates a CCD image including centroids.
Figure 21:
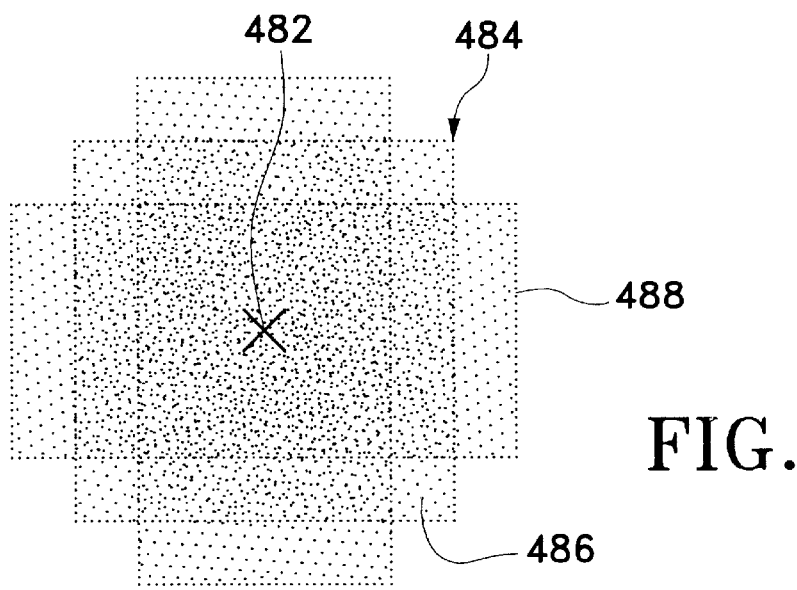
FIG. 21 is an enlarged image of a centroid.

Once a valid measurement has been made the next step 480 is to measure the local slopes of the wavefront 130, as earlier described with reference to equations herein presented. As described with reference to FIGS. 4–6, it is necessary for the software to compute the centroids 116 of the clusters of light on the CCD array 38 and then determine the distances of each of these centroids 116 from the corresponding reference centroids 29. The centroids are determined by first computing which pixels should be processed and grouping them together into clusters. The intensity-weighted centroid of each cluster is then computed. As illustrated with reference to FIG. 20, an example of an image from a myopic eye with the computed centroids 482 of cluster 484 marked by "X"s is shown. FIG. 21 illustrates a close-up of one of the clusters 484 and displays not only the centroid 482 but also the pixels 486 used in the centroiding calculation for the cluster 484. CCD pixels 488 processed in the centroiding algorithm are marked by dots. This algorithm, by way of example, isolates centroids by use of a spacial filter which removes stray light signals that create noise for the CCD image. Such filtering may be desirable before calculation of light cluster positions.

Figure 23A:
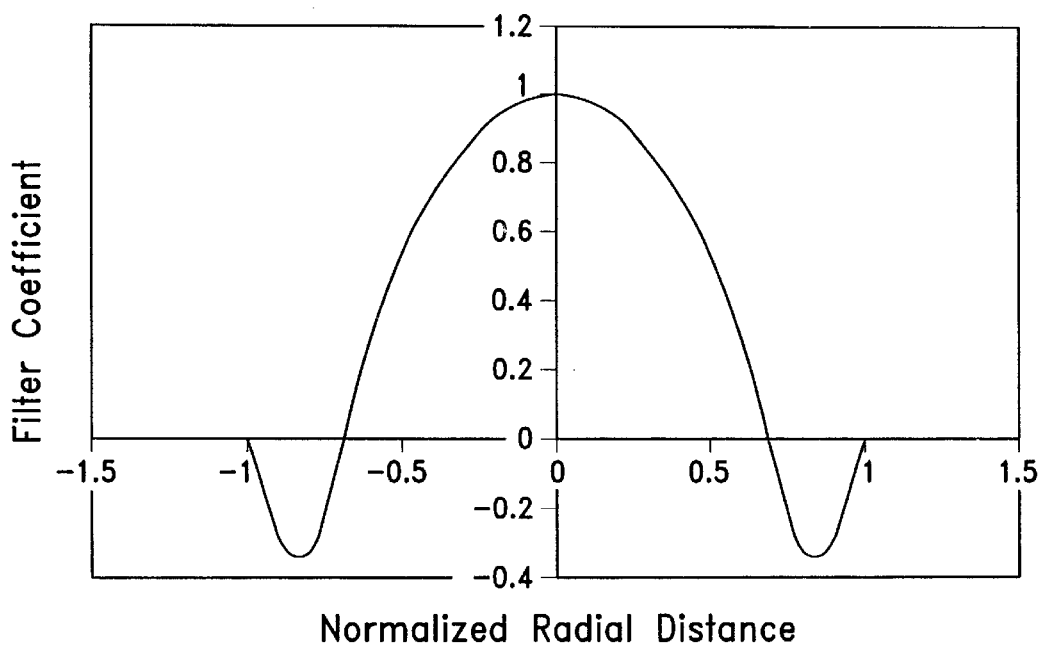
FIG. 23A illustrates a spacial filter operable in one embodiment of the present invention.
Figure 23B:
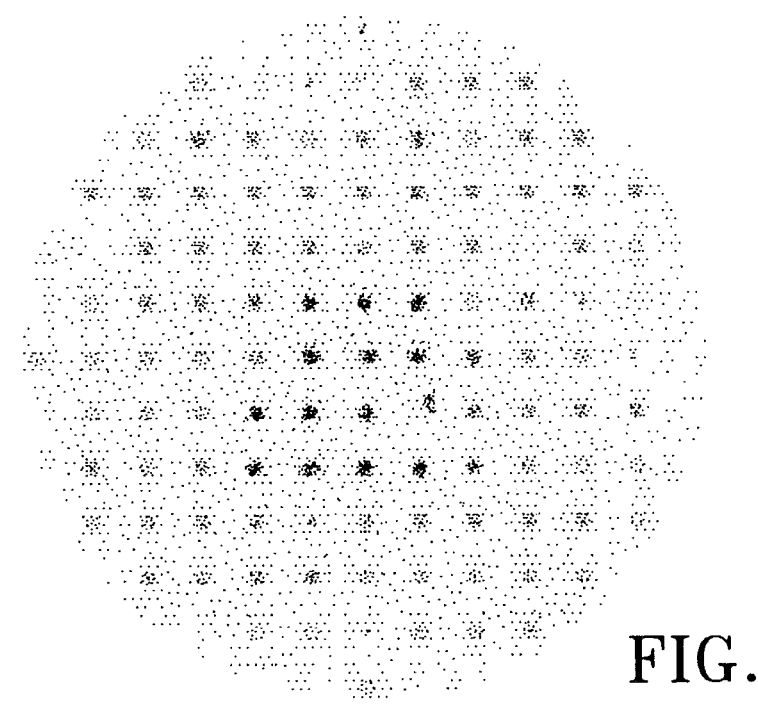
FIG. 23B illustrates a noisy CCD image before filtering to provide an image as illustrated with reference to FIG. 20.

Without filtering, computation of the cluster centroids may be made difficult as a result of noise on the image such that individual pixels with no actual data content may be brighter than pixels containing relevant data, speckle in the image may result in valid data clusters having irregular profiles with significant variation in intensity of adjacent pixels, haze or background noise may be high relative to the actual data or may be non-uniform across the image, intensity of valid data may be non-uniform across the image, scatter from different parts of the eye may result in spurious signals on the image, and high aberrations in the eye may significantly distort the clusters of valid data, by way of examples. The spatial filter permits a re-computation of the brightness of each pixel in a bitmap using a weighted averaging technique that considers surrounding pixels. In a particular application herein described for illustration and by way of example, the spatial filter is designed to yield a maximum value when centered on valid data, reduce an effect of individual bright pixels or small groups thereof, normalize background levels, smooth valid data profiles, and simplify the task of extracting the valid data from background noise or haze. One filter employed in one embodiment of the present invention is square (n×n) and includes real values (positive and negative) assigned to each pixel. The filter is designed to be optimally matched to images obtained from eyes with high, yet measurable, levels of aberration. By wave example, a cross-section through the filter is illustrated with reference to FIG. 23A. An effect of applying such a filter improves an image such as illustrated with reference to FIG. 23B to the image illustrated with reference again to FIG. 20, by way of example, a cleaner image and one that is easily processed for identification and computation of cluster centroids. By applying the filter, images that would otherwise be deemed to noisy or of insufficient quality to process, can now be processed and desired wavefront information computed.

Figure 22:
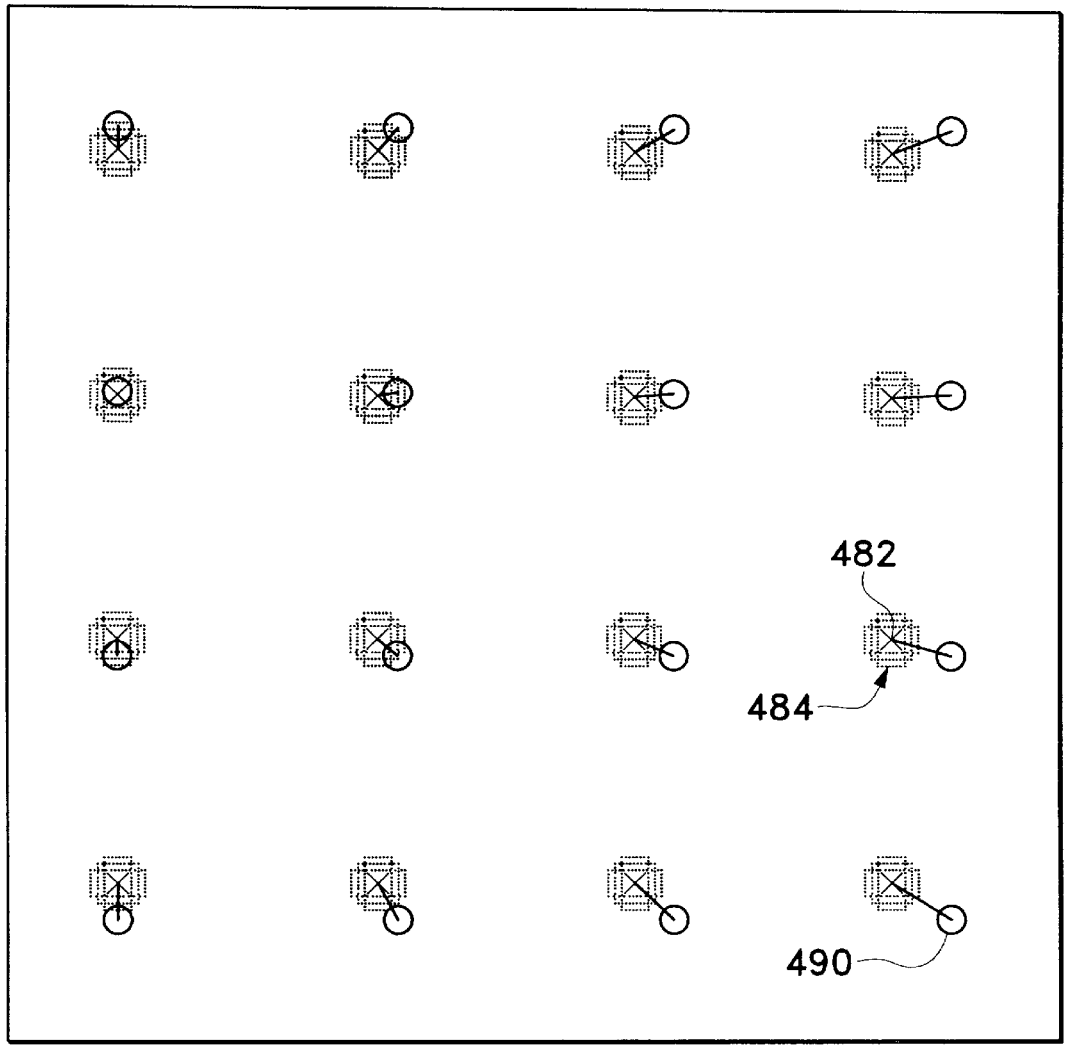
FIG. 22 illustrates an image available to an operator of a measured and reference centroid.

The center of each centroid is calculated using a standard center of mass algorithm based on light intensity. The clusters and centroids illustrated with reference to FIG. 22 are illustrated with the locations of the corresponding reference centroids 490 also visible. The open circles in this figure indicate the locations of the reference centroids. Lines connect these with the associated sample centroids 482. From the distances between the reference and measurement centroids 490, 482 respectively, and the distance between the lens array 33 and the CCD plane 36, described with reference to FIG. 6, the local slopes are calculated. Given these local slopes and information about the apparatus setup, including any and all magnification factors, it is then possible to determine the local slopes at the pupil plane and, from these, and compute the optical path difference of the eye being measured.

A description of the wavefront is then made 492. As earlier described, the reconstructed wavefront is described via a set of Zernike polynomials. The number of locations on the eye 120 at which the local slopes are determined (i.e. the number of sample points) greatly exceeds the number of terms in the polynomials that will describe the wavefront. A least-squares-fit calculation is done to find the coefficients that best describe the surface. The order of the polynomial used is sufficient to describe not only the spherical and cylindrical refractive powers ($2^{nd}$ order) but also the levels of coma ($3^{rd}$ order) and spherical aberration ($4^{th}$ order) present.

Figure 24A:
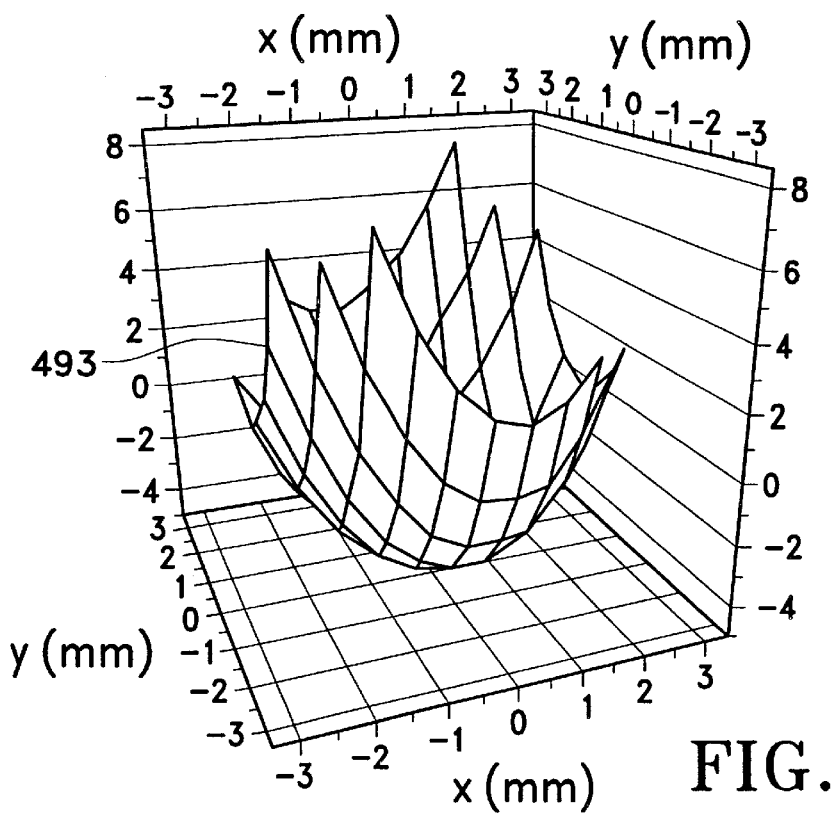
FIG. 24A is a three dimensional plot of a wavefront reconstruction in accordance with the present invention.
Figure 24B:
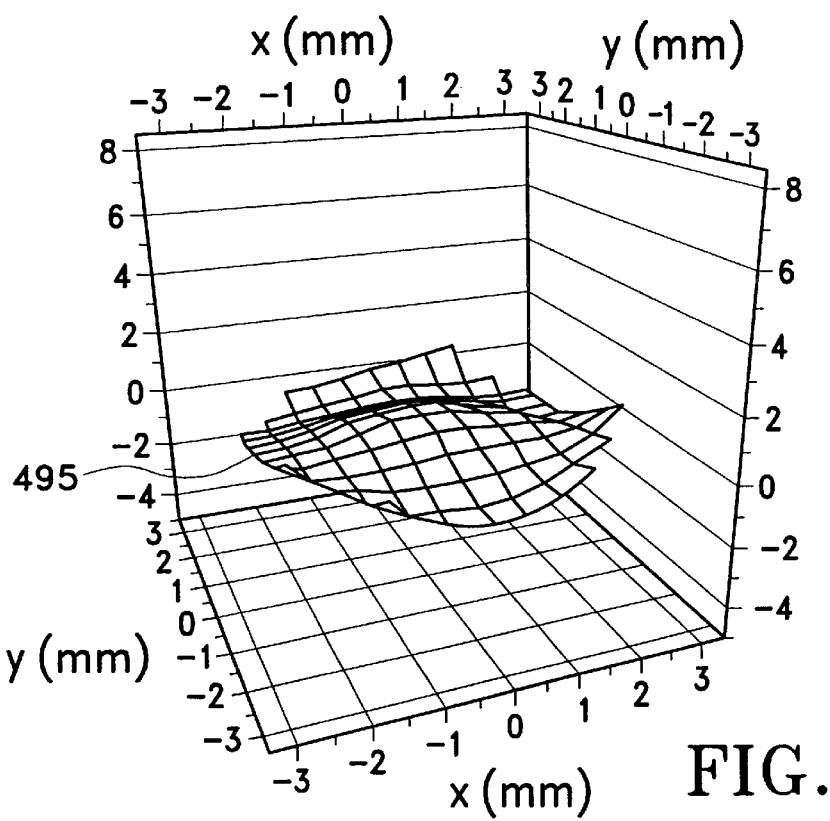
FIG. 24B illustrates a higher order aberration for the wavefront of FIG. 23.

An example of the computed Zernike coefficients for an eye and the corresponding wavefront reconstruction 493 is illustrated with reference to FIG. 24A. By way of example, for the wavefront illustrated with reference to FIG. 24A, the spherical and cylindrical powers computed from the wavefront are −1.60/−1.13×150.4. The corresponding values obtained by an optometrist performing a phoropter examination (converted to the corneal plane) were −1.47/−1.19× 150. The standard measurements of spherical and cylindrical powers agree well with the computation of spherical and cylindrical powers, but there are also higher order aberrations present. By way of further example, FIG. 24B illustrates just these higher order aberrations 495 on the same scale as the plot of FIG. 24A.

With regard to the optical path difference (OPD), scaling an optical path difference profile, OPD(x,y), by a refractive index difference (cornea to air) is not the only step. This wavefront measurement is made at a plane tangent to the cornea, as illustrated with reference to FIG. 25, which is exaggerated to illustrate the effect. The image plane of the wavefront path is the lenslet array plate. The object plane of the wavefront path is the reference plane 494. In this highly-exaggerated myopic case, herein described by way of example, one light ray 496 emerging from the eye 120 at transverse location a is detected at a transverse location b. The wavefront reconstructed from sensor data will have the slope of this ray at location b. Although this is true of the wavefront at the reference plane 494, simple scaling of this wavefront would suggest a measurement at corneal location b that may not be entirely accurate. In actuality this effect is small. The radius of curvature of the cornea is typically on the order of 7.5 mm. (a range of 7–8 mm encompasses most eyes.) At a transverse location 3 mm from the corneal apex, the distance from the corneal surface to the reference plane is only ~0.63 $\mu$m. For a 10 diopter myope, a light ray exiting the cornea at a=3.0 mm will cross the reference plane at b=2.98 mm. The difference between a and b in this example is only 20 $\mu$m. Although small this geometric effect is systematic, having progressively greater impact on the measurement with increasing radial distance from the corneal apex. To increase accuracy, compensating for the curved geometry may be performed in the following manner:

1. Wavefront slopes are calculated at each measurement point in the reference plane.
2. The cornea is assumed to have a nominal radius of curvature (~7.5 mm).
3. The wavefront slopes measured at the reference plane is projected back onto the nominally curved cornea. The wavefront is measured to have a certain slope at b in the reference plane, described above. It is a straightforward mathematical process to calculate the point a where this ray exited the cornea.
4. The wavefront is reconstructed based on the measured slopes at the calculated corneal locations.

As above described, it is desirable to obtain the best information with a wavefront measurement having patient positioned at the apparatus 300. The eye 120 being measured is at the desired location and looking in the appropriate direction. Based on analysis of the allowable eye-positioning tolerances, the apparatus 300 of this embodiment of the present invention provides the following patient position information:

The capability for ensuring that the subject eye is at the right location along the longitudinal (z) axis of the apparatus with an accuracy of +/−1 mm.

The capability for ensuring that the subject eye is properly positioned laterally with respect to the apparatus (i.e., in x-y) with an accuracy of +/−1 mm.

The capability for ensuring that the subject eye is desirably positioned in angle with respect to the apparatus (i.e., the difference between the visual axis and the optical axis of the system) with an accuracy of +/−0.5 degrees.

The capability for aligning an on-screen reticule to a set of marks applied to the eye outside the limbus to record the rotational orientation of the eye (i.e., about z) with respect to the apparatus with an accuracy of +/−one degree.

Once in position, the patient's eye can be successfully examined by the wavefront sensing technique. This embodiment of the apparatus includes a sufficient dynamic range to measure eyes over the expected scope of refractive errors.

The following list provides range and accuracy parameters, by way of example, for clinical wavefront measurements that can be obtained by this embodiment of the apparatus. This list is provided by way of illustration and does not limit the scope of the present invention.

1. capable of measuring wavefronts with spherical refractive powers in the range +6 to −15 diopters and cylindrical powers in the range 0 to −6 diopters.
2. capable of measuring coma and spherical aberration.
3. capable of measuring refractive errors over a pupil zone of up to 8 mm in diameter.
4. able to measure the refractive errors within the specified ranges to an accuracy of 0.042 $\mu$m RMS in air.

With reference again to FIG. 6, and by way of further example, the output from wavefront analyzer 26, e.g., the Zernike expansion of equation (19), can be used in a variety of ways. For example, the output may be used to continually or periodically monitor the progress or effects of an ophthalmic procedure, with such stored on disc or transmitted via e-mail, and the like. The output of the wavefront analyzer 26 is input to a processor 90 which converts the Zernike expansion of equation (19) into a form suitable for subsequent use as desired. Alternatively, the processor 90 may also be implemented at the processor 40 of the wavefront analyzer 26, described earlier with reference to FIG. 6.

By way of further example, the processor 90 can be used with preselected Zernike coefficients from the expansion of equation (19) to generate a standard sphero-cylindrical specification for a lens grinder 92 to produce a convectional optical lens, e.g., a lens for glasses, a contact lens, and the like.

As described earlier with reference to FIG. 12, the apparatus 300 of the present venture includes first and second afocal relays stages 358, 360. To retain the benefit of wavefront magnification, as a means of increasing the dynamic range of the wavefront sensor 356 to accommodate patients with large refractive errors, while at the same time allowing for incorporation of a small format, inexpensive camera to record the wavefront slope data, a modification 500 to the apparatus 300 as illustrated with reference to FIG. 26A is provided.

By way of example, a lens array may also be positioned and configured as illustrated with reference to FIG. 26B, wherein a portion of the apparatus 300 of FIG. 12 includes the first and second afocal stages 358, 360 within the optical axis 342, and the wavefront sensor 356 consist of the microlens array and CCD camera separated by a fixed distant, as earlier described with reference to FIG. 6. This optical path through the afocal relay stages results in an image of the corneal plane 502 at the lenslet array, i.e. at the entrance face of the actual wave front sensor 356. This can be accomplished by a single afocal stage. As earlier described with reference to FIG. 12, the apparatus 300 includes an intermediate image plane as insertion point, the holder 408, for a trial lens. Placing a spherical lens into the optical axis 342 at the first image plane, in theory, could be used to remove the defocus wavefront error. This would potentially expand the dynamic range of the apparatus 300. However, the trial lens approach s a moving mechanism that can position lenses at the first image plane with tremendous accuracy in repeatability. It is highly desirable that alternative means be developed to address dynamic range.

One way to accomplish this is to magnify the corneal plane image at the lenslet array with the afocal stage 360, earlier described. Magnification of the wavefront reduces the wavefront slope, so that the displacement of the focused lights spots on the CCD is decreased. The chosen magnification factor used with the apparatus 300 second afocal stage 360 is approximately 1.2 which is sufficient to cover the desired range in refractive errors. A magnification factor in excess of 1.5 is desirable for expanding the use of the apparatus 300. However, simply magnifying the corneal plane has a drawback in that it necessitate a large aperture wavefront sensor. That is, both the lens array and the CCD camera preferably have large cross-sectional areas to encompass the magnified image of the point of plane. This is not a significant issue for the lens array. However, a large format CCD camera is quite expensive and such cameras are only available from a limited number of vendors.

To resolve such concerns, the modification 500 illustrated with reference again to FIG. 26A is provided. The corneal plane 502 is imaged at a reference plane 504 by an afocal relay stage 506, which magnifies the corneal plane by a preselected amount. The lenslet array 412 is placed at the reference plane 504. Focused spots of light from the eye 120 are produced at the lenslet array focal plane 504. Rather than place the CCD detector face at the reference plane 504, an optical train 508 is inserted to image the array focal plane 413 at yet another plane, a final image plane 510, at which plane the CCD detector face is positioned. The afocal relay stages 358, 360 described earlier with reference to FIGS. 12 and 26B, may or may not be included, as desired. However, the magnification of the array focal plane at the final image plane 510 is provided. This allows a small, relatively inexpensive, active area camera to be used as the light recording element in the wavefront sensor. Details of optical design including magnification specifics can be adjusted to maximize performance for a given camera and lens array plate specification.

The advantages of the present invention are numerous. A totally objective approach is presented for measuring ocular aberrations. The approach is effective for a wide range of vision defects. Accordingly, the present invention will be of great utility in a wide variety of clinical applications. For example, the calculated Zernike coefficients can be used to develop a completely objective lens prescription. In addition, each of the wavefront sensor embodiments provides for a greater degree of accuracy over the prior art with respect to measuring wavefront deflections. Further, the present wavefront sensor can be adjusted in terms of gain simply by adjusting the separation distance between the imaging plane of the sensor and the planar array of light-sensitive cells.

The objective measurement of the present invention will also find great utility for a large variety of applications where the "patient" is unable to provide feedback as d by conventional eye diagnosis. For example, the present invention could be used to evaluate the eyes of any patient not possessed of demonstrative communicative skills, e.g., babies, animals, dead specimens, as well as any constructed optical system, since the present invention is an objective analysis not requiring any assessment from the "subject". All that is necessary is for the subject's eye to be properly positioned so that proper optical access to the eye can be obtained.

The present invention will also be used in the area of identification should it be determined that each eye's Zernike coefficients are unique. Then, the present invention would find great utility in the fields of law enforcement, credit card/bank security, or any other field where positive identification would be beneficial.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

TABLE 1

Sample Optical Component
(Refers to FIG. 12)

| Ref No. | Component | Parameter | Specification | Supplier |
| --- | --- | --- | --- | --- |
| 378 | Polarizing Beamsplitter | Physical dimensions<br>S-pol. transmittance<br>S-pol. reflectance<br>P-pol. transmittance<br>P-pol. reflectance | 38.1 mm (1.5") cube<br><6%<br>>94%<br>>94%<br>>6% | Tower Optical Corporation<br>Delray Beach, Florida |
| 358A | Lens Combination | Effective Focal Length<br>Clear Aperture | 149.5 mm<br>40 mm | Tower Optical Corporation<br>Delray Beach, Florida |
| 358B | Lens Combination | Effective Focal Length<br>Clear Aperture | 149.5 mm<br>40 mm | Tower Optical Corporation<br>Delray Beach, Florida |
| 376 | 50/50 Beamsplitter | Physical dimensions | 38.1 mm (1.5") cube | Tower Optical Corporation<br>Delray Beach, Florida |
| 374 | 50/50 Beamsplitter | Physical dimensions | 38.1 mm (1.5") cube | Tower Optical Corporation<br>Delray Beach, Florida |
| 380 | Lens | Focal length<br>Clear aperture | 40 mm<br>18 mm | Melles Griot<br>Irvine, California |
| 382A | Lens | Focal length<br>Clear aperture | 40 mm<br>18 mm | Melles Griot<br>Irvine, California |
| 382B | Lens | Focal length<br>Clear aperture | 120 mm<br>40 mm | Melles Griot<br>Irvine, California |
| 370 | 50/50 Beamsplitter | Physical dimensions | 38.1 mm (1.5") cube | Tower Optical Corporation<br>Delray Beach, Florida |

TABLE 1-continued

Sample Optical Component
(Refers to FIG. 12)

| Ref No. | Component | Parameter | Specification | Supplier |
|---|---|---|---|---|
| 366 | Fixation Target | Physical dimensions | 38.1 mm | Diversified Graphics |
| | | Material | Vellox | Orlando, Florida |
| 368 | Target Illumination Lamp | Type | Halogen/parabolic reflector | Welch Allyn |
| | | Reflector diameter | 51 mm (2") | Skaneateles Falls, New York |
| | | Voltage | 9 V maximum | |
| | | Current | 1 A | |
| | Short-Pass Filter | Wavelength Rejection Range | 620–790 nm (Part #03SWP410) | Melles Griot Irvine, California |
| 336 | Eye Illumination Lamps | Type | Gas/parabolic reflector | Welch Allyn |
| | | Reflector diameter | 25 mm (1") | Skaneateles Falls, New York |
| | | Voltage | 5 V maximum | |
| | | Current | 0.97 A | |
| | Short-λ attenuation filter | 1% transmission λ | ~455 nm (Schott Glass GG 455) | Melles Griot Irvine, California |
| | Short-Pass Filter | Wavelength Rejection Range | 620–790 nm (Part #03SWP410) | Melles Griot Irvine, California |
| | IR-λ attenuation filter | Half-max. transmission λ | ~920 nm (Schott Glass KG-3) | Florida High Tech Optics Palmetto, Florida |
| 386 | Mirror | Clear aperture | 50 mm | Melles Griot Irvine, California |
| 388 | Lens | Focal length | 40 mm | Melles Griot |
| | | Clear aperture | 18 mm | Irvine, California |
| 338 | Video Camera | CCD array dimensions | 6 mm × 8 mm | Industrial Vision Source |
| | | CCD pixel number | 494 × 768 | Carrollton, Texas |
| 398 | Mirror | Clear aperture | 25 mm | Melles Griot Irvine, California |
| 396 | Shutter | Clear aperture | 25.4 mm (1") diameter | Melles Griot Irvine, California |
| 394 | Lens | Focal length | 1000 mm | Melles Griot |
| | | Clear aperture | 50 mm | Irvine, California |
| 392 | Polarizer | Clear aperture | 16.9 mm diameter | Melles Griot |
| | | Extinction ratio | $10^{-4}$ | Irvine, California |
| | Attenuator | Clear Aperture | 25 mm diameter | Melles Griot |
| | | Transmission | 0.5/0.1 (interchangeable) | Irvine, California |
| 400 | Polarizer | Clear aperture | 16.9 mm diameter | Melles Griot |
| | | Extinction ratio | $10^{-4}$ | Irvine, California |
| 390 | Diode Laser | Wavelength | 670 nm | Power Technologies, Inc. |
| | | Output port diameter | 52 mm | Little Rock Arkansas |
| | | Beam divergence | 0.3 mrad | |
| 408 | Trial Lenses | Dioptric range | −16 to +8 diopters | Optimax |
| | | Dioptric step size | 2 diopters | Rochester, New York |
| | | Clear aperture | 12.7 mm (0.5") | |
| | Band-Pass Filter | Peak Transmission | 670 nm | Melles Griot |
| | | Wavelength Bandwidth (FWHM) | 10 nm | Irvine, California |
| 360A | Lens Combination | Effective Focal Length | 122.2 mm | Tower Optical Corporation |
| | | Clear Aperture | 40 mm | Delray Beach, Florida |
| 360B | Lens Combination | Effective Focal Length | 149.5 mm | Tower Optical Corporation |
| | | Clear Aperture | 40 mm | Delray Beach, Florida |
| 410 | Mirror | Clear Aperture | 50 mm | Melles Griot Irvine, California |
| 412 | Microlens Array | Array clear aperture | 25 mm diameter | Adaptive Optics Systems |
| | | Lenslet configuration | Square array | Cambridge, Massachusetts |
| | | lenslet dimensions | 768 μm square | |
| | | nominal focal length | 86 mm | |
| 406 | CCD Camera | CCD array dimensions | 12.3 mm square | Roper Scientific |
| | | CCD pixel dimensions | 24 mm square | Tucson, Arizona |
| | | CCD pixel number | 512 × 512 | |
| 414 | Diode Laser | Wavelength | 670 nm | Power Technologies, Inc. |
| | | Output port diameter | 5.2 mm | Little Rock, Arkansas |
| | | Beam divergence | 0.3 mrad | |
| 416 | Beam Expander | Magnification | 10 X | Edmund Scientific Company Barrington, New Jersey (Coherent) |
| 418 | Polarizers | Clear aperture | 16.9 mm diameter | Melles Griot |
| | | Extinction ratio | $10^{-4}$ | Irvine, California |
| | Attenuator | Clear Aperture | 25 mm diameter | Melles Griot |
| | | Transmission | 0.5/0.1 (interchangeable) | Irvine, California |
| 420A | Lens | Nominal focal length | −30 mm | Melles Griot |
| | | Diameter | 20 mm | Irvine, California |
| 420B | Aperture | Clear aperture | 12.7 mm | TechFab Mount Dora, Florida |

TABLE 1-continued

Sample Optical Component
(Refers to FIG. 12)

| Ref No. | Component | Parameter | Specification | Supplier |
|---|---|---|---|---|
| 422A | Aperture | Clear aperture | 127 mm | TechFab Mount Dora, Florida |
| 422B | Aperture | Clear aperture | 15 mm | TechFab Mount Dora, Florida |
|  | Lens | Nominal focal length Diameter | 400 mm 25 mm | Melles Griot Irvine, California |
| 424 | Mirror | Clear aperture | 25 mm | Melles Griot Irvine, California |
| 426 | Aperture | Clear aperture | 10 mm | TechFab Mount Dora Florida |

That which is claimed is:

1. A method for determining higher order aberrations of an eye requiring a correction of greater than −6 diopters, the method comprising:
   directing an optical beam onto a retina of an eye;
   reflecting the optical beam from the retina of the eye;
   determining characteristics of a wavefront in the reflected optical beam; and
   generating data based on the characteristics of the wavefront, which data quantifies at least one higher order aberration of the eye.

2. An apparatus for determining aberrations of an eye comprising:
   a patient head rest comprising an adjustment, the patient head rest associated with an optical table having a base, the base comprising:
   a) a probe beam generating apparatus for providing a probe beam;
   b) probe beam directing optics operable with the probe beam generating apparatus, the probe beam directing optics comprising a beam splitter, a mirror, and a lens operable within a beam path of the probe beam, the probe beam directing optics being capable of directing the probe beam toward an eye of a patient positioned on the patient head rest;
   c) video image components, the video image components comprising a light source for illuminating the eye of the patient, and a mirror and a video camera for viewing the eye, the video image components being capable of generating an image of the eye of a patient positioned on the patient head rest;
   d) eye fixation components, the eye fixation components comprising a fixation target for viewing by the eye of a patient, a light source for illuminating the target, and a lens and a mirror operable within a path of the target, the fixation components being capable of generating a target that the eye of a patient positioned on the patient head rest can view; and
   e) wavefront directing and analyzing components operable with the eye of a patient, the wavefront directing and analyzing components comprising a lens, a mirror, a microlens array, and a camera operable within an optical path of the eye, and a data processor operable with the camera, the wavefront directing and analyzing components being capable of measuring a wavefront emanating from the eye of a patient positioned on the patient head rest and determining aberrations of said eye that range from at least about + or −1 diopters to at least about + or −6 diopters.

3. A method for determining higher order aberrations of an eye requiring a correction of greater than −6 diopters of myopia, the method comprising the steps of:
   directing an optical beam onto a retina of an eye;
   reflecting the optical beam from the retina of the eye;
   determining characteristics of a wavefront in the reflected optical beam; and
   generating data based on the characteristics of the wavefront, which data quantifies at least one higher order aberration of the eye.

4. A method for determining higher order aberrations of an eye requiring a correction of greater than +6 diopters of hyperopia, the method comprising the steps of:
   directing an optical beam onto a retina of an eye;
   reflecting the optical beam from the retina of the eye;
   determining characteristics of a wavefront in the reflected optical beam; and
   generating data based on the characteristics of the wavefront, which data quantifies at least one higher order aberration of the eye.

5. An apparatus for determining aberrations of an eye, comprising:
   a patient head rest associated with an optical table having a base, the base having:
   i) a probe beam generating apparatus for providing a probe beam;
   ii) probe beam directing optics operable with the probe beam generating apparatus, the probe beam directing optics comprising a beam splitter, a mirror, and a lens operable within a beam path of the probe beam, the probe beam directing optics being capable of directing the probe beam toward an eye of a patient positioned on the patient head rest;
   iii) video image components, the video image components comprising a light source for illuminating the eye of the patient, and a mirror and a video camera for viewing the eye, the video image components being capable of generating an image of the eye of the patient positioned on the patient head rest;
   iv) eye fixation components, the eye fixation components comprising a fixation target for viewing by the eye of a patient, a light source for illuminating the target, and a lens and a mirror operable within a path of the target, the fixation components being capable of generating a target that the eye of the patient positioned on the patient head rest can view; and v) wavefront directing and analyzing components operable with the eye of a patient, the wavefront directing and analyzing components comprising a lens, a mirror, a microlens array, and a camera operable within an optical path of the eye, and a data processor operable with the camera, the wavefront directing and analyzing components being capable of measuring a wavefront emanating from the eye of the patient positioned on the patient head rest and determining higher order aberrations of the eye that range from at least about +1 diopter to at least about +6 diopters and from at least about −1 diopter to at least about −6 diopters.

6. A method for determining higher order aberrations of an eye requiring a correction of greater than +6 diopters, the method comprising:

directing an optical beam onto a retina of an eye;

reflecting the optical beam from the retina of the eye;

determining characteristics of a wavefront in the reflected optical beam; and generating data based on the characteristics of the wavefront, which data quantifies at least one higher order aberration of the eye.

* * * * *